US010351568B2

(12) United States Patent
Finley et al.

(10) Patent No.: US 10,351,568 B2
(45) Date of Patent: Jul. 16, 2019

(54) COMPOSITIONS AND METHODS FOR ENHANCING PROTEASOME ACTIVITY

(71) Applicant: President and Fellows of Harvard College, Cambridge, MA (US)

(72) Inventors: Daniel J. Finley, Jamaica Plain, MA (US); Randall W. King, Brookline, MA (US); Byung-Hoon Lee, Cambridge, MA (US); Min Jae Lee, Jamaica Plain, MA (US); Timothy C. Gahman, Encinitas, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/933,671

(22) Filed: Nov. 5, 2015

(65) Prior Publication Data
US 2016/0214989 A1    Jul. 28, 2016

Related U.S. Application Data

(62) Division of application No. 13/575,812, filed as application No. PCT/US2011/022929 on Jan. 28, 2011, now abandoned.

(60) Provisional application No. 61/373,404, filed on Aug. 13, 2010, provisional application No. 61/336,959, filed on Jan. 28, 2010.

(51) Int. Cl.
| C07D 487/04 | (2006.01) |
| C07D 207/333 | (2006.01) |
| C07D 207/335 | (2006.01) |
| C07D 209/44 | (2006.01) |
| C07D 233/64 | (2006.01) |
| C07D 401/06 | (2006.01) |
| C07D 401/10 | (2006.01) |
| C07D 401/12 | (2006.01) |
| C07D 403/04 | (2006.01) |
| C07D 403/06 | (2006.01) |
| C07D 471/04 | (2006.01) |
| C07D 209/08 | (2006.01) |
| C07D 401/04 | (2006.01) |
| G01N 33/573 | (2006.01) |

(52) U.S. Cl.
CPC ....... *C07D 487/04* (2013.01); *C07D 207/333* (2013.01); *C07D 207/335* (2013.01); *C07D 209/08* (2013.01); *C07D 209/44* (2013.01); *C07D 233/64* (2013.01); *C07D 401/04* (2013.01); *C07D 401/06* (2013.01); *C07D 401/10* (2013.01); *C07D 401/12* (2013.01); *C07D 403/04* (2013.01); *C07D 403/06* (2013.01); *C07D 471/04* (2013.01); *G01N 33/573* (2013.01); *G01N 2333/948* (2013.01); *G01N 2500/04* (2013.01)

(58) Field of Classification Search
CPC .................................................. C07D 487/04
USPC .......................................................... 546/184
See application file for complete search history.

(56) References Cited

U.S. PATENT DOCUMENTS

| 4,148,895 | A | 4/1979 | Lattrell et al. |
| 4,290,940 | A | 9/1981 | Wirth et al. |
| 5,561,149 | A | 10/1996 | Azria et al. |
| 5,852,046 | A | 12/1998 | Lang et al. |
| 5,859,035 | A | 1/1999 | Anthony et al. |
| 6,063,782 | A | 5/2000 | Kimura et al. |
| 6,201,129 | B1 | 3/2001 | Miller et al. |
| 6,310,217 | B1 | 10/2001 | Lehr |
| 6,469,171 | B1 | 10/2002 | Banwell et al. |
| 6,500,853 | B1 | 12/2002 | Seehra et al. |
| 6,589,954 | B1 | 7/2003 | Mavunkel et al. |
| 6,627,645 | B2 | 9/2003 | Andersson et al. |
| 6,828,344 | B1 | 12/2004 | Seehra et al. |
| 6,867,209 | B1 | 3/2005 | Mavunkel et al. |
| 7,238,713 | B2 | 7/2007 | Anderson et al. |
| 7,417,063 | B2 | 8/2008 | Smallheer et al. |
| 7,425,642 | B2 | 9/2008 | Watanabe et al. |
| 7,482,354 | B2 | 1/2009 | Traquandi et al. |
| 7,528,165 | B2 | 5/2009 | Hsieh et al. |
| 7,576,206 | B2 | 8/2009 | Bernardini et al. |
| 7,632,955 | B2 | 12/2009 | Hsieh et al. |
| 7,767,817 | B2 | 8/2010 | Wang et al. |
| 7,781,479 | B2 | 8/2010 | Takahashi et al. |
| 8,097,644 | B2 | 1/2012 | Beard et al. |
| 8,197,819 | B2 | 6/2012 | Srivastava et al. |
| 8,293,781 | B2 | 10/2012 | Tomoo et al. |

(Continued)

FOREIGN PATENT DOCUMENTS

| CN | 101016294 A | 8/2007 |
| DE | 4325204 A | 2/1995 |

(Continued)

OTHER PUBLICATIONS

Lee et al. Nature, vol. 467|Sep. 9, 2010| doi:10.1038/nature09299.*

(Continued)

*Primary Examiner* — Nizal S Chandrakumar
(74) *Attorney, Agent, or Firm* — Foley Hoag LLP; DeAnn F. Smith

(57) ABSTRACT

Proteinopathies result from the proteasome not acting efficiently enough to eliminate harmful proteins and prevent the formation of the pathogenic aggregates. As described herein, inhibition of proteasome-associated deubiquitinase Usp14 results in increased proteasome efficiency. The present invention therefore provides novel compositions and methods for inhibition of Usp14, enhancement of proteasome activity and treatment of proteinopathies.

8 Claims, 64 Drawing Sheets

(56) References Cited

U.S. PATENT DOCUMENTS

| | | | |
|---|---|---|---|
| 9,849,135 B2 | 12/2017 | Finley et al. | |
| 2002/0037887 A1 | 3/2002 | Pintor et al. | |
| 2004/0122096 A1 | 6/2004 | Lang et al. | |
| 2005/0075348 A1 | 4/2005 | Harriman et al. | |
| 2005/0113357 A1 | 5/2005 | Anderson et al. | |
| 2006/0135540 A1 | 6/2006 | Lin et al. | |
| 2007/0185184 A1 | 8/2007 | Hanson et al. | |
| 2007/0203121 A1 | 8/2007 | Merce Vidal et al. | |
| 2008/0171772 A1 | 7/2008 | Beard et al. | |
| 2008/0188453 A1 | 8/2008 | Adams et al. | |
| 2009/0047246 A1 | 2/2009 | Beigelman et al. | |
| 2009/0118503 A1 | 5/2009 | Sprott et al. | |
| 2009/0143371 A1 | 6/2009 | Buettelmann et al. | |
| 2009/0163545 A1* | 6/2009 | Goldfarb .............. | A61K 31/122 514/312 |
| 2009/0215750 A1 | 8/2009 | Bamberg et al. | |
| 2009/0227538 A1 | 9/2009 | Fruchtel et al. | |
| 2009/0264384 A1 | 10/2009 | Didsbury et al. | |
| 2009/0264457 A1 | 10/2009 | Codony-Soler et al. | |
| 2009/0318446 A1 | 12/2009 | Fischer et al. | |
| 2010/0074955 A1 | 3/2010 | Buschmann et al. | |
| 2010/0087415 A1 | 4/2010 | Whitten et al. | |
| 2010/0087446 A1 | 4/2010 | Chakravarty et al. | |
| 2010/0099726 A1 | 4/2010 | Cantley et al. | |
| 2010/0197708 A1 | 8/2010 | Talley et al. | |
| 2010/0204282 A1 | 8/2010 | Hutchinson et al. | |
| 2010/0249069 A1 | 9/2010 | Donello et al. | |
| 2010/0331297 A1 | 12/2010 | Bulawa et al. | |
| 2011/0009453 A1 | 1/2011 | Donello et al. | |
| 2011/0098483 A1 | 4/2011 | Petasis et al. | |
| 2011/0144090 A1 | 6/2011 | Elder et al. | |
| 2011/0319403 A1 | 12/2011 | Zhou et al. | |
| 2012/0006417 A1 | 1/2012 | Folk | |
| 2012/0022057 A1 | 1/2012 | Zhou et al. | |
| 2012/0064175 A1 | 3/2012 | Vukovic et al. | |
| 2012/0071448 A1 | 3/2012 | Donello et al. | |
| 2012/0245186 A1 | 9/2012 | Blackman et al. | |
| 2012/0316193 A1 | 12/2012 | Foley et al. | |
| 2013/0029948 A1 | 1/2013 | Roppe et al. | |
| 2013/0045992 A1 | 2/2013 | Finley et al. | |
| 2013/0150385 A1 | 6/2013 | Blackman et al. | |
| 2013/0156755 A1 | 6/2013 | Blackman et al. | |
| 2013/0171105 A1 | 7/2013 | Blackman et al. | |

FOREIGN PATENT DOCUMENTS

| | | |
|---|---|---|
| EP | 0 562 832 | 9/1993 |
| EP | 0 639 573 | 7/1994 |
| EP | 1837329 A1 | 9/2007 |
| EP | 2020230 A1 | 2/2009 |
| EP | 2141163 A1 | 1/2010 |
| JP | 07-133274 | 5/1995 |
| JP | 2000063354 A | 2/2000 |
| JP | 2001151771 A | 6/2001 |
| JP | 2009179589 A | 8/2009 |
| WO | WO-95/13266 | 5/1995 |
| WO | WO-97/36881 | 10/1997 |
| WO | WO-97/46226 | 12/1997 |
| WO | WO-98/27089 | 6/1998 |
| WO | WO-99/43672 | 9/1999 |
| WO | WO-2001/044182 | 6/2001 |
| WO | WO-2003/041644 | 5/2003 |
| WO | WO-2004/020409 | 3/2004 |
| WO | WO-2004/104007 | 12/2004 |
| WO | WO-2005/021558 | 3/2005 |
| WO | WO-2005/025515 | 3/2005 |
| WO | WO-2005/066126 | 7/2005 |
| WO | WO-2006/087355 | 8/2006 |
| WO | WO-2006/125324 | 11/2006 |
| WO | WO-2007/095561 | 8/2007 |
| WO | WO-2008/024978 | 2/2008 |
| WO | WO-2008/100867 | 8/2008 |
| WO | WO-2008/109702 | 9/2008 |
| WO | WO-2008/120818 A1 | 10/2008 |
| WO | WO-2008/147536 | 12/2008 |
| WO | WO-2009/013010 | 1/2009 |
| WO | WO-2009/062118 | 5/2009 |
| WO | WO-2009/071577 | 6/2009 |
| WO | WO-2009/073620 | 6/2009 |
| WO | WO-2009/097141 | 8/2009 |
| WO | WO-2009/108551 | 9/2009 |
| WO | WO-2009/117676 | 9/2009 |
| WO | WO-2009/118292 | 10/2009 |
| WO | WO-2009/127686 | 10/2009 |
| WO | WO-2009/130481 | 10/2009 |
| WO | WO-2009/136175 | 11/2009 |
| WO | WO-2009/158011 | 12/2009 |
| WO | WO-2009/158371 | 12/2009 |
| WO | WO-2010/015816 | 2/2010 |
| WO | WO-2010/019391 | 2/2010 |
| WO | WO-2010/067123 | 6/2010 |
| WO | WO-2011/038579 | 4/2011 |
| WO | WO-2011/094545 | 8/2011 |
| WO | WO-2011/127333 | 10/2011 |
| WO | WO-2012/012712 | 1/2012 |
| WO | WO-2012/078757 | 6/2012 |
| WO | WO-2012/096919 | 7/2012 |
| WO | WO-2012/106343 | 8/2012 |
| WO | WO-2012/116061 | 8/2012 |
| WO | WO-2012/116247 | 8/2012 |
| WO | WO-2012/141796 | 10/2012 |
| WO | WO-2012/162293 | 11/2012 |
| WO | WO-2012/162372 | 11/2012 |
| WO | WO-2012/162584 | 11/2012 |
| WO | WO-2013/006864 | 1/2013 |
| WO | WO-2013/014104 | 1/2013 |
| WO | WO-2013/067162 | 5/2013 |
| WO | WO-2013/067165 | 5/2013 |
| WO | WO-2013/074594 | 5/2013 |
| WO | WO-2014/116228 A1 | 7/2014 |

OTHER PUBLICATIONS

West (Solid-State Chemistry and Its Applications, 1984, John Wiley & Sons).*
Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000).*
Jorden, ZCommunications » World Alzheimer Day: Dec. 20, 2015.*
Golde (Alzheimer's Research & Therapy 2009, 1:5 Alzheimer's Research & Therapy. (2009), 1:5, pp. 1-12).*
Venkatesh, J. Pharm. Sci. 89, 145-54 (2000).*
Damia , European Journal of Cancer 2009, 45, 2768-2781.*
Johnson, British Journal of Cancer 2001, 84, 1424-1431.*
Abdel-Motaleb et al., "Studies with Azoles and Benzoazoles: A Novel Simple Approach for Synthesis of 3-Functionally Substituted 3-Acylindoles," J. Heterocyclic. Chem., 44(1):109-114 (2007).
Aparoy et al., "Pharmacophore modeling and virtual screening for designing potential 5-Lipoxygenase inhibitors," Bioorganic & Medicinal Chemistry Letters, 20(3):1013-1018 (2010).
CAS RN 133674-62-1, STN Entry Date May 10, 1991.
CAS RN 169501-21-7 STN Entry Date Nov. 1, 1995.
CAS RN 57248-18-7 STN Entry Date Nov. 16, 1984.
CAS RN 784194-52-1 STN Entry Date Nov. 19, 2004.
De Freitas et al., "Development of CoMFA and CoMSIA models of affinity and selectivity for indole ligands of cannabinoid CB1 and CB2 receptors," European Journal of Medicinal Chemistry, 44:2482-2496 (2009).
Gadaginamath et al., "Synthesis and Antimicrobial Activity of 4-Iso-Gramines, 4-Aryl-Thiomethyl and 3-Aminoacetyl Derivatives of 2-Methylindoles," Revue Roumaine de Chimie, 40(30):265-273 (1995).
Gadaginamath et al., "Synthesis and Antimicrobial Activity of Novel 3-Thiazolyl/Imidazo (2,1-b)-1,3,4-Thiadiazolyl/Anilinoacetyl/ Phenoxyacetyl Indole Derivatives," Indian Journal of Heterocyclic Chemistry, 9(1):33-38 (1999).
Gitto et al., "Development of 3-substituted-1H-indole derivatives as NR2B/NMDA receptor antagonists", Bioorganic & Medicinal Chemistry, 17(4): 1640-1647 (2009).

(56) References Cited

OTHER PUBLICATIONS

International Search Report dated Oct. 24, 2011, from PCT/US2011/022929.
Iwaki et al., "Water-Soluble Melatonins: Syntheses of Melatonins Carrying a Glycosyl Group at the 1-Position," Heterocyles, 60(6):1411-1418 (2003).
Kang et al., "Cell Cycle Arrest and Cytochrome c-mediated Apoptotic Induction in A549 Human Lung Cancer Cells by MCS-C2, an Analog of Sangivamycin," Journal of Microbiology and Biotechnology, 20(2):428-432 (2010).
Lee et al., "Enhancement of Proteasome Activity by a Small-Molecule Inhibitor of Usp14", Nature, 467:179-184 (2010).
Liu et al., "Discovery of a Peroxisome Proliferator Activated Receptor γ (PPARγ) Modulator with Balanced PPARαActivity for the Treatment of Type 2 Diabetes and Dyslipidemia," J. Med. Chem., 52(14): 4443-4453 (2009).
Marchand et al., "Synthesis and structure-activity relationships of N-aryl(indol-3-yl)glyoxamides as antitumor agents", Bioorganic & Medicinal Chemistry, 17(18): 6715-6727 (2009).
Office Action dated Dec. 31, 2014, from U.S. Appl. No. 13/468,757.
Office Action dated Jul. 14, 2014, from U.S. Appl. No. 13/468,757.
Preobrazhenskaya et al., "Synthesis and Study of the Pharmacological Activity of 1-(Indolyl-3')-2-Alkylaminoethanols", Pharmaceutical Chemistry Journal, pp. 532-536 (1970). Retrieved from the Internet: URL:http://rd.springer.com/content/pdf/10.1007/BF00763238.pdf [retrieved on Oct. 7, 2014].
Rao et al., "An efficient, mild, and selective Ullmann-type N-arylation of indoles catalyzed by copper(I) complex", Tetrahedron, 65(23): 4619-4624 (2009).
Registry (STN) CAS Registration No. 314261-13-7.
Registry (STN) CAS Registration No. 325742-01-6.
Registry (STN) CAS Registration No. 380907-35-7.
Registry (STN) CAS Registration No. 670268-20-9.
Stearns et al., "Synthesis and biological evaluation of 6-aryl-6H-pyrrolo[3,4-d]pyridazine derivatives: high-affinity ligands to the α2δ subunit of voltage gated calcium channels," Bioorganic & Medicinal Chemistry Letters, 14(5):1295-1298 (2004).
Supplementary European Search Report from EP 11 73 7731 dated Jul. 3, 2014.
Van Zandt et al., "Discovery of 3-[(4,5, 7-Trifluorobenzothiazol-2-yl)methyl]indole-N-acetic Acid (Lidorestat) and Congeners as Highly Potent and Selective Inhibitors of Aldose Reductase for Treatment of Chronic Diabetic Complications," J. Med. Chem., 48:3141-3152 (2005).
Vidovic et al., "A Combined Ligand- and Structure-Based Virtual Screening Protocol Identifies Submicromolar PPARγ Partial Agonists," Chem Med Chem, 6(1): 94-103 (2011).
West, Solid-State Chemistry and Its Applications, John Wiley & Sons (1984).
Wolff, Burger's Medicinal Chemistry and Drug Discovery, vol. 1, Principles and Practice, John Wiley & Sons, New York (1997).
CAS RN 1001821-94-8 STN Entry Date Feb. 6, 2008.
CAS RN 1002513-72-5 STN Entry Date Feb. 10, 2008.
CAS RN 1002540-87-5 STN Entry Date Feb. 10, 2008.
CAS RN 1002650-53-4 STN Entry Date Feb. 11, 2008.
CAS RN 1016398-38-1 STN Entry Date Apr. 22, 2008.
CAS RN 1016419-68-3 STN Entry Date Apr. 22, 2008.
CAS RN 1036150-97-6 STN Entry Date Jul. 27, 2008.
CAS RN 1051931-25-9 STN Entry Date Sep. 23, 2008.
CAS RN 1051931-30-6 STN Entry Date Sep. 23, 2008.
CAS RN 1061503-00-1 STN Entry Date Oct. 15, 2008.
CAS RN 1062588-84-4 STN Entry Date Oct. 17, 2008.
CAS RN 1111454-71-7 STN Entry Date Feb. 25, 2009.
CAS RN 1135019-03-2 STN Entry Date Apr. 15, 2009.
CAS RN 1197824-79-5 STN Entry Date Dec. 16, 2009.
CAS RN 315676-34-7 STN Entry Date Jan. 22, 2001.
CAS RN 315676-40-5 STN Entry Date Jan. 22, 2001.
CAS RN 315678-64-9 STN Entry Date Jan. 22, 2001.
CAS RN 315682-90-7 STN Entry Date Jan. 22, 2001.
CAS RN 315683-10-4 STN Entry Date Jan. 22, 2001.
CAS RN 315683-27-3 STN Entry Date Jan. 22, 2001.
CAS RN 315707-65-4 STN Entry Date Jan. 22, 2001.
CAS RN 352460-55-0 STN Entry Date Aug. 23, 2001.
CAS RN 352460-56-1 STN Entry Date Aug. 23, 2001.
CAS RN 378193-78-3 STN Entry Date Dec. 26, 2001.
CAS RN 378196-69-1 STN Entry Date Dec. 26, 2001.
CAS RN 378196-95-3 STN Entry Date Dec. 26, 2011.
CAS RN 378196-96-4 STN Entry Date Dec. 26, 2011.
CAS RN 379238-63-8 STN Entry Date Dec. 28, 2011.
CAS RN 379243-81-9 STN Entry Date Dec. 28, 2001.
CAS RN 379243-95-5 STN Entry Date Dec. 28, 2001.
CAS RN 379246-74-9 STN Entry Date Dec. 28, 2011.
CAS RN 380218-32-6 STN Entry Date Jan. 2, 2002.
CAS RN 380483-85-2 STN Entry Date Jan. 4, 2002.
CAS RN 380483-86-3 STN Entry Date Jan. 4, 2002.
CAS RN 380907-36-8 STN Entry Date Jan. 8, 2002.
CAS RN 381688-24-0 STN Entry Date Jan. 10, 2002.
CAS RN 381724-23-8 STN Entry Date Jan. 10, 2002.
CAS RN 381724-24-9 STN Entry Date Jan. 10, 2002.
CAS RN 381724-25-0 STN Entry Date Jan. 10, 2002.
CAS RN 474647-92-2 STN Entry Date Nov. 27, 2002.
CAS RN 477526-69-5 STN Entry Date Dec. 23, 2002.
CAS RN 500198-70-9 STN Entry Date Mar. 21, 2003.
CAS RN 670269-86-0 STN Entry Date Apr. 2, 2004.
CAS RN 670270-57-2 STN Entry Date Apr. 2, 2004.
CAS RN 670270-58-3 STN Entry Date Apr. 2, 2004.
CAS RN 690642-21-8 STN Entry Date Jun. 8, 2004.
CAS RN 748147-13-9 STN Entry Date Sep. 20, 2004.
CAS RN 879187-54-9 STN Entry Date Apr. 4, 2006.
CAS RN 930453-30-8 STN Entry Date Apr. 17, 2007.
CAS RN 948437-44-3 STN Entry Date Sep. 28, 2007.
CAS RN 948437-48-7 STN Entry Date Sep. 28, 2007.
Jaung et al., "Synthesis and keto—enol isomerism of 1-alkyl-2-methyl-5, 6-dicyano-3-[2-(5-alkylamino-2, 3-dicyanopyrazin-6-yl)-1-hydroxyethenyl]-pyrrolo [2,3-b] pyrazine," Dyes Pigments, 48(2):133-141 (2001).
Trader et al., "Establishment of a suite of assays that support the discovery of proteasome stimulators," Biochim Biophys Acta, 1861(4):892-899 (2017).
Chen, X., et al, "Thiopurine analogue inhibitors of severe acute respiratory syndrome-coronavirus papain-like protease, a deubiquitinating and delSGylating enzyme," Antiviral Chemistry & Chemotherapy 19:151-156 (2009).
Database Registry Chemical Abstracts, Ethanone, 1-[1-(2-fluorophenyl)-2, 5-dimethyl-1H-pyrrol-3-yl]-2-(4-methyl-1-piperidinyl)-, Database Accession No. 380907-35-7, CAS Registry No. 380907-35-7 (Jan. 8, 2002).
Database Registry Chemical Abstracts, Ethanone, 1-[1-(4-fluorophenyl)-2, 5-dimethyl-1H-pyrrol-3-yl]-2-(1-piperidinyl)-, Database Accession No. 670268-20-9, CAS Registry No. 670268-20-9 (Apr. 2, 2004).
Database Registry Chemical Abstracts, Ethanone, 1-[1-(4-fluorophenyl)-2, 5-dimethyl-1H-pyrrol-3-yl]-2-(1-pyrrolidinyl)-, Database Accession No. 314245-33-5, CAS Registry No. 314245-33-5 (Jan. 17, 2001).
Database Registry Chemical Abstracts, Ethanone, 1-[1-(4-fluorophenyl)-2, 5-dimethyl-1H-pyrrol-3-yl]-2-(4-methyl-1-piperidinyl)-, Database Accession No. 325742-01-6, CAS Registry No. 325742-01-6 (Mar. 5, 2001).
Database Registry Chemical Abstracts, Ethanone, 1-[2, 5-dimethyl-1-(4-methylphenyl)-1H-pyrrol-3-yl]-2-(1-piperidinyl)-, Database Accession No. 301683-66-9, CAS Registry No. 301683-66-9 (Nov. 8, 2000).
Database Registry Chemical Abstracts, Ethanone, 2-(2, 6-dimethyl-4-morpholinyl)-1-(2, 5-dimethyl-1-phenyl-1H-pyrrol-3-yl)-, Database Accession No. 314261-13-7, CAS Registry No. 314261-13-7 (Jan. 17, 2001).
International Search Report dated Apr. 10, 2013, from PCT/US13/23147.
Nag et al., "A small-molecule inhibitor of deubiquitinating enzyme USP14 Inhibits Dengue virus replication," Virus Research, 165:103-106 (2012).

(56) References Cited

OTHER PUBLICATIONS

Perry, J.W. et al, "Antiviral Activity of a Small Molecule Deubiquitinase Inhibitor Occurs via Induction of the Unfolded Protein Response," PLoS Pathogens, Jul. 2012, vol. 8, Issue 7, pp. 1-15.
Wang, D. et al, "The Leader Proteinase of Foot-and-Mouth Disease Virus Negatively Regulates the Type I Interferon Pathway by Acting as a Viral Deubiquitinase," Journal of Virology, Apr. 2011, Fol. 85, No. 8, pp. 3758-3766.
Examiner's Notification of Defects from related application, dated Dec. 22, 2015.
Notification receipt from foreign associate, from related application, dated Dec. 24, 2015.

* cited by examiner native gel &
LLVY-AMC staining

CBB staining

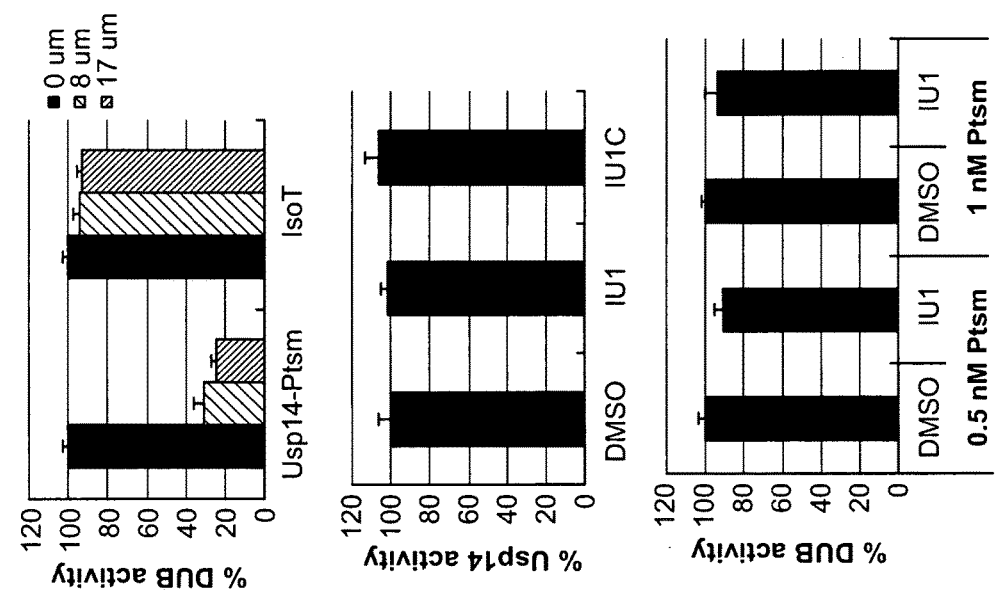
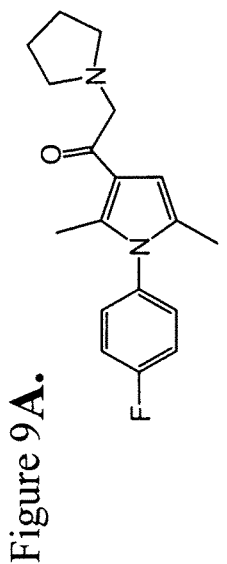
Figure 9A. Figure 9B. Figure 9C. Figure 9D. Figure 9E.

IU1C

| Name | Compound | Percent inhibition* | | IC$_{50}$** | |
|---|---|---|---|---|---|
| | | Usp14/26S | IsoT | Usp14/26S | IsoT |
| IU1 |  | 70 (at 8 μM) | 10 (at 8 μM) | 4 | 80 |
| | | 58 (at 4 μM) | 3 (at 4 μM) | 5.5 | 100 |
| IU1-1 |  | 36 | 0 | | |
| IU1-2 |  | 82 | 7 | 1.7 | 55 |
| IU1-3 |  | 53 | 0 | | |
| IU1-4 |  | 55 | 0 | | |
| IU1-5 |  | 0 | 0 | | |
| IU1-6 |  | 0 | 0 | | |

| | | | | | |
|---|---|---|---|---|---|
| IU1-7 |  | 52 | 2 | | |
| IU1-8 |  | 19 | 0 | | |
| IU1-13 |  | 74 | 6 | 3.9 | 80 |
| IU1-14 |  | 20 | 11 | | |
| IU1-15 |  | 44 | 10 | | |
| IU1-16 |  | 0 | 2 | | |
| IU1-17 |  | 21 | 11 | | |
| IU1-18 |  | 41 | 8 | | |

| | | | | | |
|---|---|---|---|---|---|
| IU1-24 |  | 1 | 6 | | |
| IU1-25 |  | 0 | 13 | | |
| IU1-26 |  | 0 | 7 | | |
| IU1-27 |  | 0 | 8 | | |
| IU1-28 |  | 20 | 10 | | |
| IU1-29 |  | 7 | 7 | | |
| IU1-30 |  | 3 | 8 | | |

Figure 31 (continued)

| ID | Structure | | | | |
|---|---|---|---|---|---|
| IU1-31 | (2-methoxyphenyl pyrrole pyrrolidine ketone) | 4 | 7 | | |
| IU1-32 | (3-fluorophenyl pyrrole pyrrolidine ketone) | 24 | 6 | | |
| IU1-33 | (4-chlorophenyl pyrrole pyrrolidine ketone) | 92 | 27 | 1.1 | 33 |
| IU1-34 | (phenyl pyrrole pyrrolidine ketone) | 29 | 6 | | |
| IU1-35 | (4-methylphenyl pyrrole pyrrolidine ketone) | 29 | 4 | | |
| IU1-36 | (4-dimethylaminophenyl pyrrole pyrrolidine ketone) | 0 | 4 | | |
| IU1-37 | (2-chlorophenyl pyrrole pyrrolidine ketone) | 0 | 1 | | |
| IU1-38 | (4-methoxyphenyl pyrrole pyrrolidine ketone) | 45 | 2 | | |

| | | | | | |
|---|---|---|---|---|---|
| IU1-39 |  | 3 | 1 | | |
| IU1-40 |  | 46 | 8 | | |
| IU1-41 |  | 0 | 0 | | |
| IU1-42 |  | 5 | 0 | | |
| IU1-43 |  | 84 | 22 | 1.9 | 34 |
| IU1-44 |  | 93 | 25 | 0.7 | 25 |
| IU1-45 |  | 5 | 0 | | |
| IU1-46 |  | 70 | 5 | 9.7 | 93 |

Figure 31 (continued)

| IU1-47 | (structure) | 92 | 18 | 0.6 | 20 |
|---|---|---|---|---|---|
| IU1-48 | (structure) | 31 | 0 | | |
| IU1-49 | (structure) | 49 | 0 | | |
| IU1-50 | (structure) | 61 | 0 | | |
| IU1-51 | (structure) | 69 | 5 | | |
| IU1-52 | (structure) | 57 | 12 | | |
| IU1-53 | (structure) | 63 | 11 | | |
| IU1-54 | (structure) | 85 | 11 | 1 | 29 |

| | | | | | |
|---|---|---|---|---|---|
| IU1-55 |  | 60 | 8 | | |
| IU1-56 |  | 78 | 11 | | |
| IU1-57 |  | 36 | 8 | | |
| IU1-58 |  | 36 | 7 | | |
| IU1-59 |  | 60 | 10 | | |
| IU1-60 |  | 89 | 9 | 0.8 | 31 |
| IU1-61 |  | 87 | 16 | 0.8 | 18 |

Figure 31 (continued)

| | | | |
|---|---|---|---|
| IU1-62 | O₂N-phenyl-dimethylpyrrole-C(O)CH₂-N(4-methylpiperidine) | 53 | 2 |
| IU1-63 | O₂N-phenyl-dimethylpyrrole-C(O)CH₂-N(methyl)(ethyl) | 55 | 6 |
| IU1-64 | MeO-phenyl-dimethylpyrrole-C(O)CH₂-N(piperidine) | 48 | 0 |
| IU1-65 | MeO-phenyl-dimethylpyrrole-C(O)CH₂-N(4-methylpiperidine) | 16 | 0 |
| IU1-66 | MeO-phenyl-dimethylpyrrole-C(O)CH₂-N(methyl)(ethyl) | 20 | 0 |
| IU1-67 | biphenyl-dimethylpyrrole-C(O)CH₂-N(piperidine) | 4 | 3 |
| IU1-68 | tBu-phenyl-dimethylpyrrole-C(O)CH₂-N(piperidine) | 7 | 2 |

| | | | | | |
|---|---|---|---|---|---|
| IU1-69 |  | 86 | 18 | 3.2 | 53 |
| IU1-70 |  | 4 | 5 | | |
| IU1-71 |  | 9 | 8 | | |
| IU1-72 |  | 17 | 5 | | |
| IU1-73 |  | 0 | 0 | | |
| IU1-74 |  | 50 | 2 | | |
| IU1-75 |  | 77 | 16 | 0.9 | 24 |

| | | | |
|---|---|---|---|
| IU1-76 |  | 4 | 1 |
| IU1-77 |  | 8 | 1 |
| IU1-78 |  | 69 | 0 |
| IU1-79 |  | 49 | 0 |
| IU1-80 |  | 71 | 0 |
| IU1-81 |  | 52 | 3 |
| IU1-82 |  | 68 | 15 |

| | | | |
|---|---|---|---|
| IU1-83 |  | 52 | 6 |
| IU1-84 |  | 34 | 0 |
| IU1-85 |  | 5 | 6 |
| IU1-86 |  | 4 | 0 |
| IU1-87 |  | 63 | 11 |
| IU1-88 |  | 73 | 7 |
| IU1-89 |  | 82 | 8 |

| | | | |
|---|---|---|---|
| IU1-90 |  | 73 | 7 |
| IU1-91 |  | 24 | 0 |
| IU1-92 |  | 9 | 0 |
| IU1-93 |  | 13 | 2 |
| IU1-94 |  | 86 | 18 |
| IU1-95 |  | 74 | 15 |
| IU1-96 |  | 40 | 16 |

| | | | | | |
|---|---|---|---|---|---|
| C'1 (C12) |  | 30 | 0 | | |
| C'2 (C31) |  | 14 | 0 | | |
| C'3 (C73) |  | 30 | 7 | | |
| C'4 (C100) |  | 14 | 0 | | |
| C'5 (C106) |  | 12 | 3 | | |
| C'6 (C118) |  | 11 | 0 | | |
| C'7 (C121) |  | 33 | 2 | | |
| C'8 (C133) |  | 27 | 0 | | |

| | | | | | |
|---|---|---|---|---|---|
| C'9 (C139) |  | 10 | 1 | | |

| Enzyme | $K_M$ (μM) | Substrates | References for $K_M$ |
|---|---|---|---|
| USP14-26S | 11 | Ub-AMC | This study |
| BAP1 | 7.0 | Ub-AMC | Personal communication, K. Wilkinson |
| IsoT | 1.4 | Ub-AMC | Dang et al (1998) Biochemistry, 37: 1868 |
| UCH37 | 13 | Ub-AMC | Yao et al (2006) Nat Cell Biol, 8: 994 |
| UCH-L1 | 0.041 | Ub-AMC | Liu et al (2003) Chem Biol, 10: 837 |
| UCH-L3 | 0.039 | Ub-AMC | Dang et al (1998) Biochemistry, 37: 1868 |
| USP2 CD | 0.55 | Ub-AMC | Hassiepen et al (2007) Anal Biochem, 371: 201 |
| USP7 CD | 44 | Ub-AMC | Fernandez-Montalvan et al (2007) FEBS J, 274: 4256 |
| USP15 | 3.0 | Ub-AMC | This study |

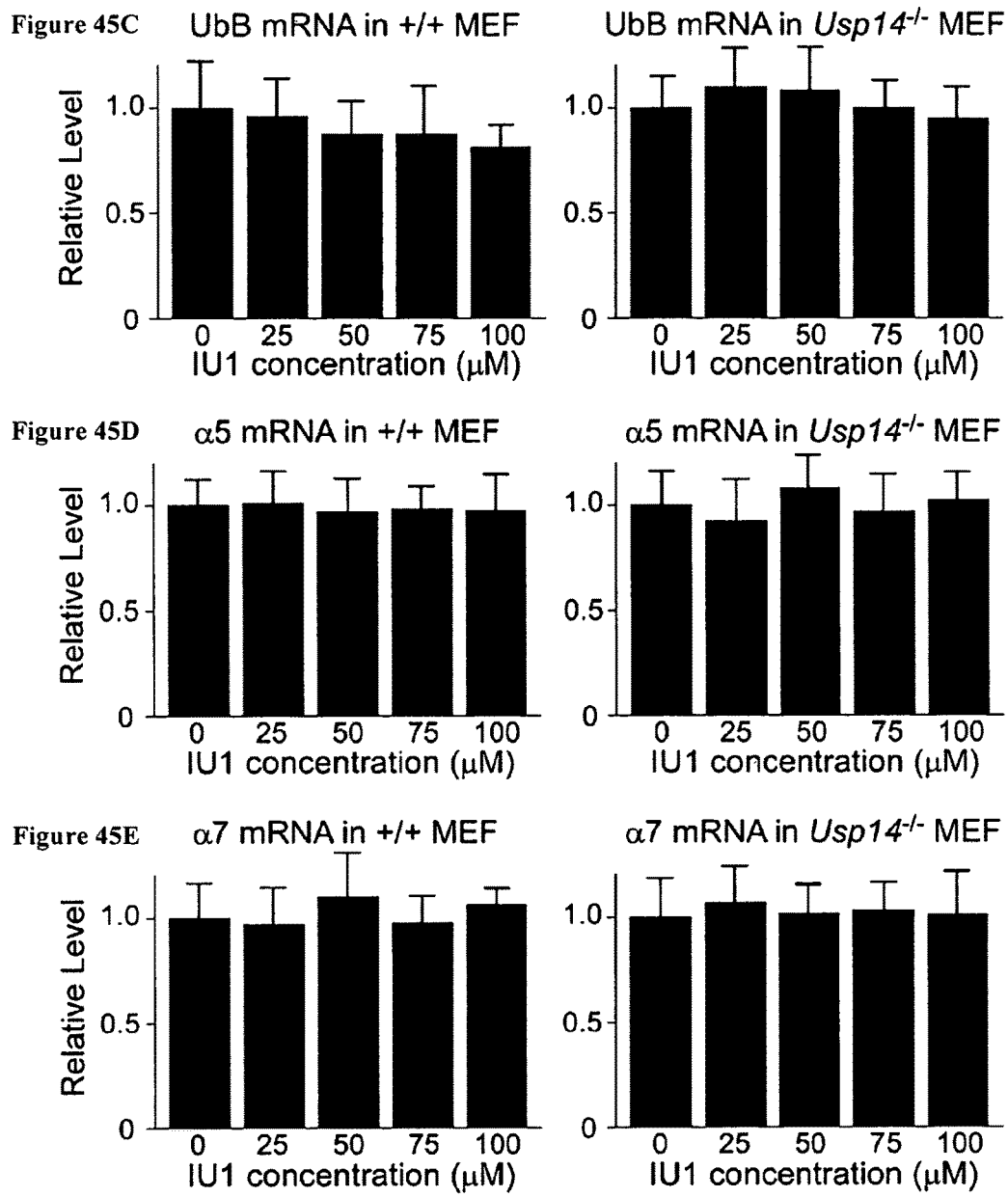

COMPOSITIONS AND METHODS FOR ENHANCING PROTEASOME ACTIVITY

RELATED APPLICATIONS

This application is a divisional application of U.S. patent application Ser. No. 13/575,812, which is the National Stage application under 35 U.S.C. § 371 of PCT/US2011/022929, filed Jan. 28, 2011, which claims the benefit of priority to U.S. Provisional Patent Application Ser. No. 61/373,404, filed Aug. 13, 2010, and U.S. Provisional Patent Application Ser. No. 61/336,959, filed Jan. 28, 2010; the contents of all of which are hereby incorporated by reference.

GOVERNMENT SUPPORT

This invention was made with U.S. Government support under National Institutes of Health Grant Nos. GM065592, GM66492, and DK082906. The government has certain rights in the invention.

BACKGROUND

The proteasome is a large protein complex that contains 33 distinct subunits. Proteasome complexes function as proteases in part to degrade unneeded or misfolded proteins. Proteasomes regulate many aspects of cell physiology, and proteasome dysfunction has been implicated in a variety of diseases, including cancer and neurodegenerative diseases (Finley D., (2009), Annu Rev. Biochem., 78, 477-513; Hoeller and Dikic, (2009), Nature, 458, 438-444; Demarto and Gillette, (2007), Cell, 129, 659-662); Dahlmann, B. (2007) BCB Biochem 8, Suppl 1, S3; Schartz A L and Ciechanover A (2009) Ann Rev Pharmacol Toxicol 49, 73-96).

Most, but not all, proteasome substrates are targeted for degradation via the covalent attachment of multimeric chains of a small, highly-conserved protein called ubiquitin. Because longer ubiquitin chains interact more strongly with the proteasome than shorter chains (Thrower et al. (2000), EMBO J. 19, 94-102), processes that alter ubiquitin chain length frequently also affect substrate degradation rates. The length of ubiquitin chains attached to substrates tagged for proteasome degradation can be modulated by certain proteasome-associated deubiquitinating enzymes and ubiquitin ligases. These deubiquitinating enzymes and ligases appear to regulate proteasome activity by disassembling or extending proteasome-bound ubiquitin chains.

Mammalian proteasomes contain three major deubiquitinating enzymes: Rpn11, Uch37, and Usp14 (Finley D., (2009), Annu Rev. Biochem., 78, 477-513). Rpn11 removes ubiquitin from the tagged substrate by cutting at the junction between the ubiquitin chain and the substrate. Because the Rpn11-mediated cleavage occurs following a substrate's commitment to proteolysis, but prior to substrate degradation, Rpn11 helps to prevent ubiquitin from being degraded along with the substrate, thus minimizing fluctuations in cellular ubiquitin levels. Additionally, because the proteasome substrate must pass through a narrow translocation channel before encountering the proteasome's sequestered proteolytic sites, removal of a bulky ubiquitin chain may also facilitate substrate translocation. Thus, removal of the ubiquitin chain by Rpn11 promotes substrate degradation through en bloc removal of the ubiquitin chain at a relatively late step in the proteasome pathway (Verma et al., (2002) Science, 298, 611-615; Yao and Cohen, (2002), Nature, 419, 403-407).

In contrast to Rpn11, Uch37 functions prior to the commitment of a substrate to proteasome degradation. Uch37 disassembles ubiquitin chains at the substrate-distal tip (Lam et al., (1997), Nature, 385, 737-740), and its enzymatic activity shortens chains rather than remove them entirely. It has been proposed that chain trimming by Uch37 increases the ability of the proteasome to discriminate between long and short multiubiquitin chains (Lam et al., (1997), Nature, 385, 737-740). Little is known about how Uch37 may regulate proteasome function in cells.

Very little is known about the function of Usp14. However, the yeast ortholog of Usp14, Ubp6, has been suggested to disassemble ubiquitin chains at the substrate-distal tip and to function prior to the commitment of a substrate to proteasome degradation. (Hanna et al., (2006), Cell, 127(7), 1401-1413). Ubp6 is thought to act as a proteasome inhibitor, and prior work on Ubp6 has indicated a noncatalytic mode of proteasome inhibition (Hanna et al., (2006), Cell, 127(7), 1401-1413).

SUMMARY

The present invention provides novel compositions and methods for the inhibition of Usp14, the enhancement of proteasome activity and the treatment of proteinopathies and other diseases for which enhanced protein breakdown may be therapeutic. Aside from proteinopathies, the enhancement of proteasome activity may be therapeutic for any disease characterized by deficient proteasome activity, or deficient activity of other components of the ubiquitin-proteasome pathway, such as in von Hippel-Lindau disease, spinocerebellar ataxia 1, Angelman syndrome, giant axon neuropathy, inclusion body myopathy with Paget disease of bone and frontotemporal dementia (IBMPFD), and others (Lehman, N. L., (2009), Acta Neuropathologica, 118(3), 329-347; Weihl et al., (2007), Neuromuscular Disorders, 17, 87-87). Enhancing proteasome activity could also be therapeutic for diseases in which proteasome substrates are involved and contribute to pathology, but which do not satisfy a strict definition of proteopathies. For example, numerous oncoproteins are proteasome substrates and their ability to promote cancer could potentially be attenuated by enhancing proteasome activity.

One aspect of the invention relates to a compound represented by formula I, II, III, IV, V, VI, VII, or VIII, or pharmaceutically acceptable salt, solvate, hydrate, prodrug, chemically-protected form, enantiomer or stereoisomer thereof; wherein the formula are as defined below.

Another aspect of the invention relates to a method of inhibiting the deubiquitination activity of a Usp14 protein comprising contacting the Usp14 protein with IU1 or a compound of formula I, II, III, IV, V, VI, VII, or VIII, or a pharmaceutically acceptable salt, solvate, hydrate, prodrug, chemically-protected form, enantiomer or stereoisomer thereof.

Another aspect of the invention relates to a method of enhancing protein degradation by a proteasome in a cell comprising contacting the cell with IU1 or a compound of formula I, II, III, IV, V, VI, VII, or VIII, or a pharmaceutically acceptable salt, solvate, hydrate, prodrug, chemically-protected form, enantiomer or stereoisomer thereof.

Another aspect of the invention relates to a method of treating or preventing a proteinopathy in a subject comprising administering to the subject IU1 or a compound of formula I, II, III, IV, V, VI, VII, or VIII, or a pharmaceutically acceptable salt, solvate, hydrate, prodrug, chemically-protected form, enantiomer or stereoisomer thereof, or a pharmaceutical composition comprising the same.

Another aspect of the invention relates to a method of enhancing proteasome function in a subject comprising administering to the subject IU1 or a compound of formula I, II, III, IV, V, VI, VII, or VIII, or a pharmaceutically acceptable salt, solvate, hydrate, prodrug, chemically-protected form, enantiomer or stereoisomer thereof, or a pharmaceutical composition comprising the same.

Another aspect of the invention relates to a method of increasing degradation of Tau, TDP-43 or ataxin-3 in a subject comprising administering to the subject IU1 or a compound of formula I, II, III, IV, V, VI, VII, or VIII, or a pharmaceutically acceptable salt, solvate, hydrate, prodrug, chemically-protected form, enantiomer or stereoisomer thereof, or a pharmaceutical composition comprising the same.

Another aspect of the invention relates to an isolated proteasome lacking enzymatically active Uch37 and comprising enzymatically active Usp14. In certain embodiments the proteasome comprises enzymatically inactive Uch37 and/or vinylsulfone-Uch37 adducts. In some embodiments the enzymatically active Usp14 is a recombinant protein. In certain embodiments the proteasome is a human proteasome or a murine proteasome.

Another aspect of the invention relates to a method of generating a proteasome comprising enzymatically inactive Uch37 and further comprising enzymatically active Usp14 comprising purifying a proteasome lacking Usp14 but comprising Uch37, treating the purified proteasome with a deubiquitinase inhibitor, and reconstituting the purified proteasome with enzymatically active Usp14. In certain embodiments the proteasome is a human proteasome or a murine proteasome. In some embodiments the proteasome is purified from HEK293 cells. In some embodiments the deubiquitinase inhibitor is ubiquitin-vinylsulfone. In certain embodiments the active Usp14 is recombinantly produced.

Another aspect of the invention relates to a method of screening for an inhibitor of Usp14 comprising providing a proteasome comprising enzymatically inactive Uch37 and further comprising enzymatically active Usp14, contacting the proteasome with a test compound and a Usp14 substrate, and determining whether the test compound inhibits the deubiquitination of the substrate. In certain embodiments, the substrate is coupled to a reporter that is detectable after cleavage by a deubiquitinase and/or is an ubiquitin-dependent proteasome substrate. In some embodiments the substrate is Ub-AMC or polyubiquitinated cyclin B. In certain embodiments, deubiquitination of the substrate is demonstrated by inhibition of substrate degradation. In some embodiments the proteasome comprises vinylsulfone-Uch37 adducts. In certain embodiments the Usp14 is a recombinant protein. In some embodiments the proteasome is a human proteasome or a murine proteasome.

Another aspect of the invention relates to a kit comprising an isolated proteasome lacking enzymatically active Uch37 and comprising enzymatically active Usp14, and instructions of use. In certain embodiments, the kit can comprise a Usp14 substrate. In some embodiments the Usp14 substrate is Ub-AMC and/or polyubiquitinated cyclin B.

Additional aspects, embodiments, and advantages of the invention are discussed below in detail. Moreover, the foregoing information and the following detailed description are merely illustrative examples of various aspects and embodiments of the invention, and are intended to provide an overview or framework for understanding the nature and character of the claimed aspects and embodiments.

or UBL domain deficient Usp14 (Usp14-ΔUBL) and stained using antibodies specific for Tau, Usp14 or Actin, as indicated.

Figure 7:
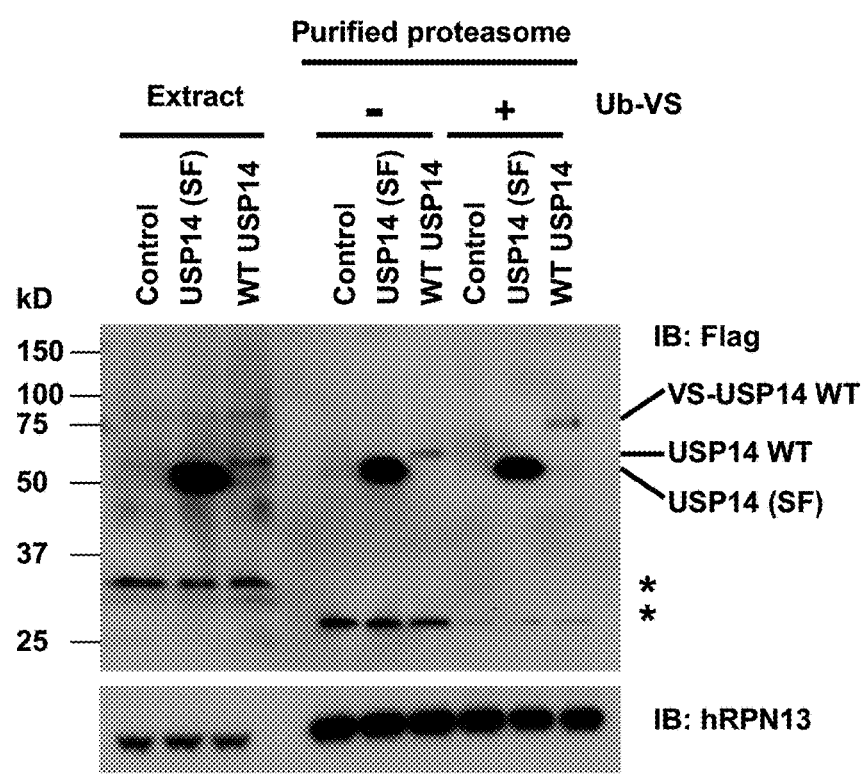

FIG. 7 shows immunoblots that were performed on cellular lysates from 293 cells that co-expressed the indicated forms of flag-tagged Usp14 along with tagged hRpn11 either before (Extract) or after (Purified proteasome) proteasome affinity purification and stained using anti-Flag antibody. Where indicated, Ub-VS was incubated with lysate prior to proteasome purification. Extract samples represent 5% of total. Asterisks, nonspecific signals. Proteasome subunit Rpn13, load control. Control samples, empty vector.

Figure 8A:
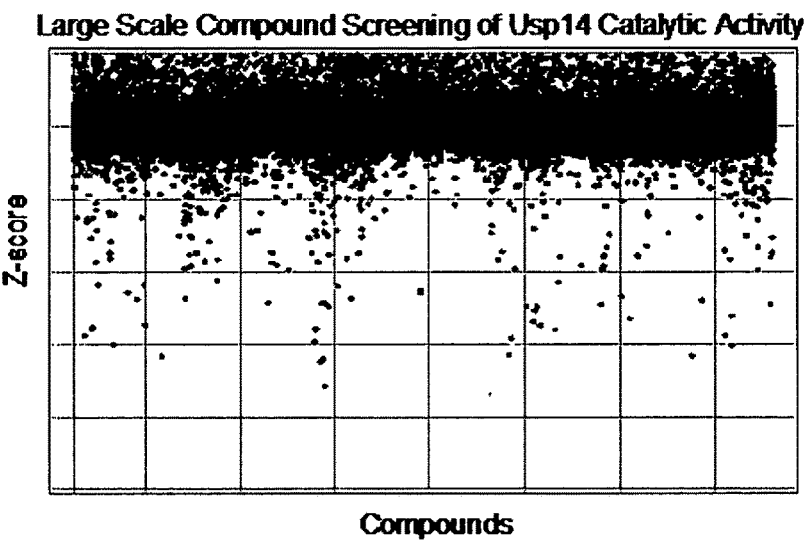

FIG. 8A shows a statistical plot of the high-throughput large scale compound screening for inhibitors of Usp14 catalytic inhibitors.

Figure 8B:
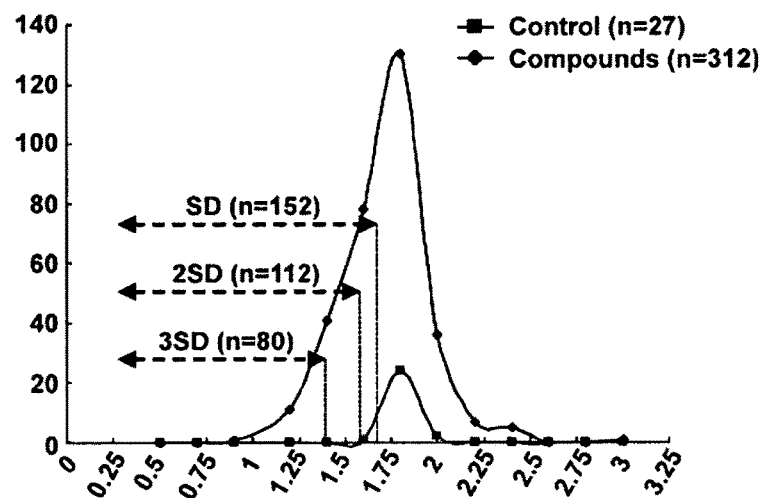

FIG. 8B shows a frequency distribution curve used to determine AMC quenching compounds (control=bottom curve).

FIG. 9A shows the chemical structure of Usp14 inhibitor IU1.

FIG. 9B shows a graph depicting (left) the inhibition of Usp14 loaded proteasome (Usp14-Ptsm) deubiquitinase activity by IU1 (left bar=0 μM, second to left bar=4 μM, third bar=8 μM, right bar=17 μM) and (right) the lack of quenching of AMC fluorescence by IU1 (left bar=0 μM, right bar=17 μM).

FIG. 9C shows a graph depicting (left) the inhibition of Usp14 loaded proteasome (Usp14-Ptsm) deubiquitinase activity by IU1 (left bar=0 μM, middle bar=8 μM, right bar=17 μM) and (right) the lack of inhibition of Isopeptidase T (IsoT) by IU1 (left bar=0 μM, middle bar=8 μM, right bar=17 μM).

FIG. 9D shows a graph depicting the lack of inhibition of Usp14 that has not been complexed to the proteasome by either vehicle (DMSO), IU1 or IU1C.

FIG. 9E shows a graph depicting the lack of inhibition of 26S human proteasomes (Ptsm) that had not been treated with Ub-VS by either vehicle (DMSO) or IU1 (i.e, proteasomes which lack Usp14).

Figure 10A:
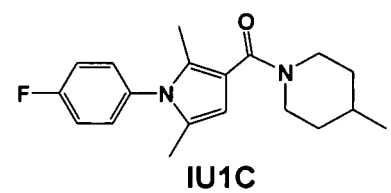

FIG. 10A shows the chemical structure of IU1C, an inactive control compound for IU1.

Figure 10B:
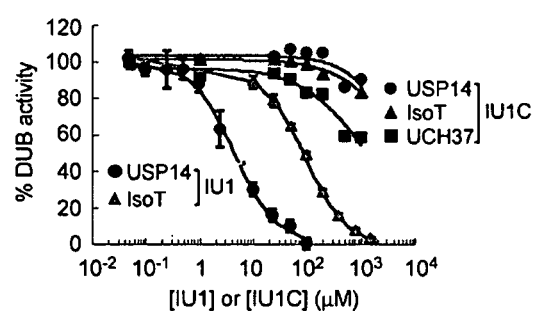

FIG. 10B shows a plot comparing the deubiquitinase inhibition activity of IU1 (bottom circles, bottom triangles) with the deubiquitinase inhibition activity of IU1C (top circles, top triangles, squares).

Figure 10C:
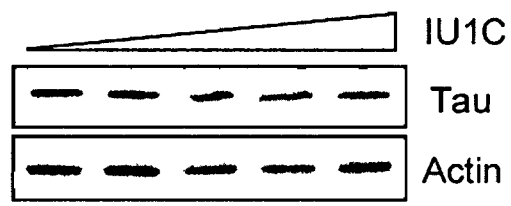

FIG. 10C shows the ineffectiveness of IU1C in promoting Tau degradation. Immunoblots were performed using lysates of MEF cells that co-expressed Tau and Usp14 and that were treated with 0, 25, 50, 75 or 100 μM IU1C and stained with antibodies specific for either Tau or Actin.

Figure 10D:
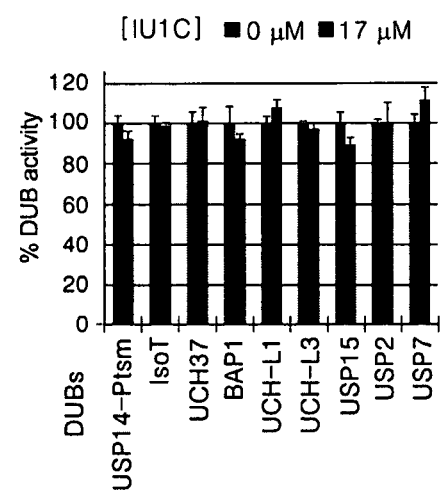

FIG. 10D shows a graph depicting inhibition of the deubiquitinase activity of the indicated deubiquitinases by IU1C (left bars=0 μM, right bars=17 μM).

Figure 11A:
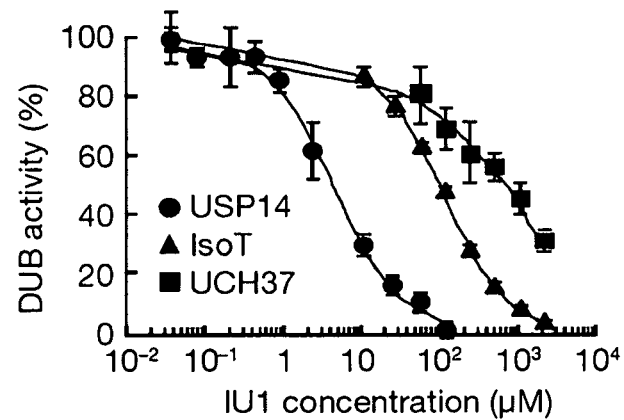

FIG. 11A shows a plot depicting the deubiquitinase activity of proteasome bound Usp14, IsoT or Uch37 that had been treated with the indicated concentration of IU1.

Figure 11B:
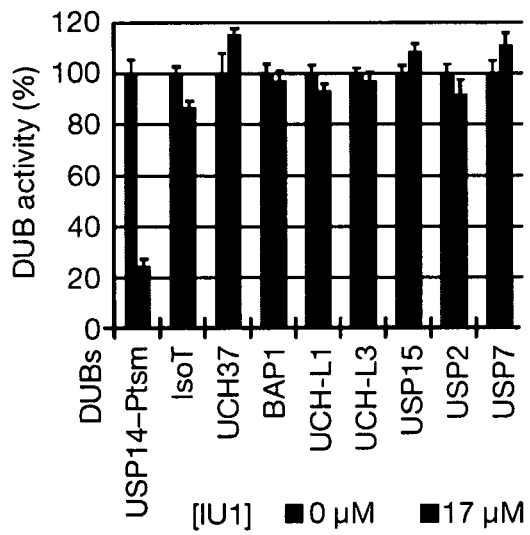

FIG. 11B shows a graph depicting the inhibition of the deubiquitinase activity of the indicated deubiquitinases by IU1 (left bars=0 μM, right bars=17 μM).

Figure 12A:
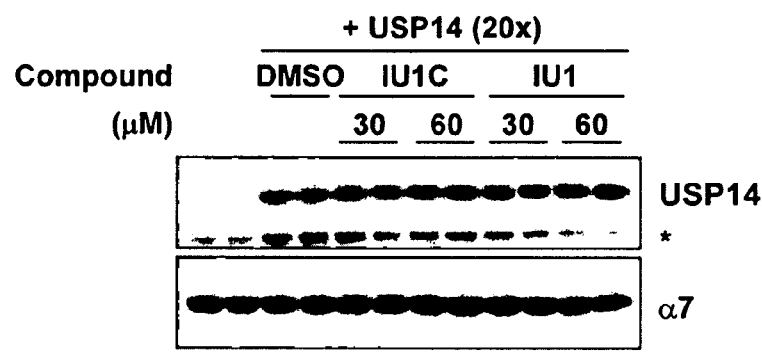

FIG. 12A shows immunoblots of purified 26S human proteasomes (~4 nM) that had been incubated with or without Usp14 (80 nM) and treated either with vehicle (DMSO), IU1C or IU1 at the indicated concentrations and stained with antibodies specific for either Usp14 or Alpha7. The asterisk (*) denotes a nonspecific signal generated by the anti-Usp14 antibody.

Figure 12B:
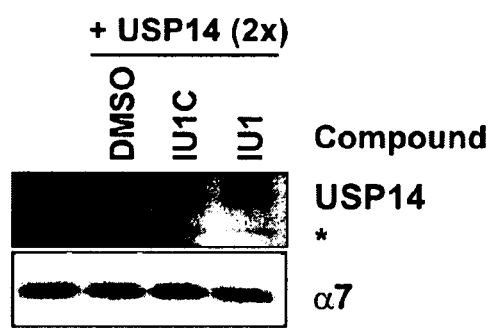

FIG. 12B shows immunoblots as in FIG. 12A, except ~2-fold molar excess of Usp14 was incubated with the proteasome in the absence or presence of the indicated compound (30 μM).

Figure 13:
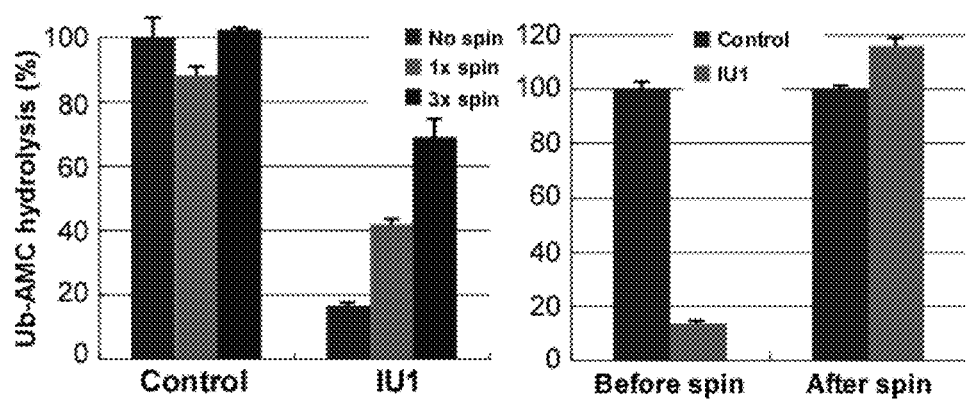

FIG. 13 shows graphs depicting the deubiquitination activity of proteasome bound Usp14 that had been treated with vehicle (control) or IU1 and subjected to the indicated number of rounds of ultrafiltration (spins, left panel; no spin=left bar, 1×spin=middle bar, 3×spin=right bar), or spin-column gel filtration (right panel; control=left bar, IU1=right bar).

Figure 14A:
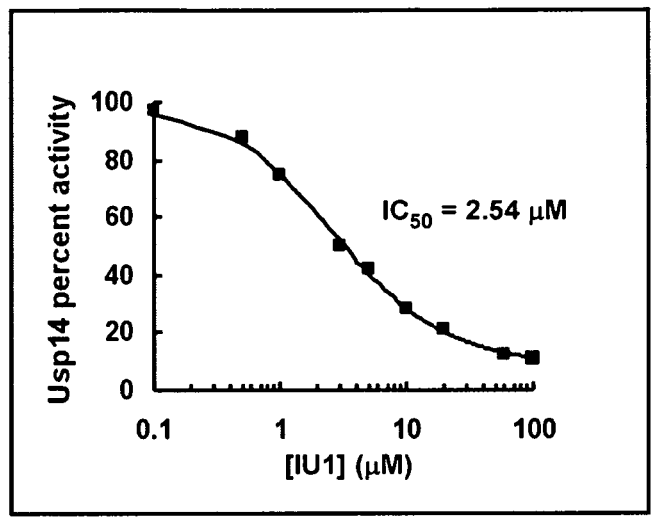

FIG. 14A shows a plot depicting an $IC_{50}$ curve of proteasome bound Usp14 treated with the indicated concentration of IU1 for 45 minutes.

Figure 14B:
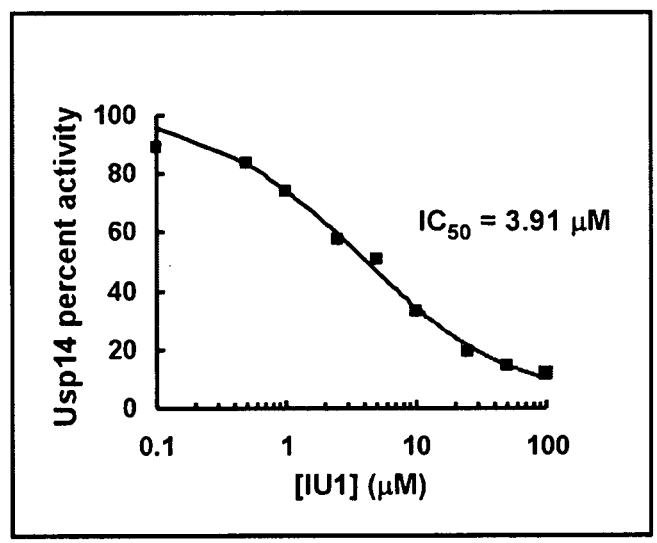

FIG. 14B shows a plot depicting an $IC_{50}$ curve of proteasome bound Usp14 treated with the indicated concentration of IU1 for 30 minutes.

Figure 15:
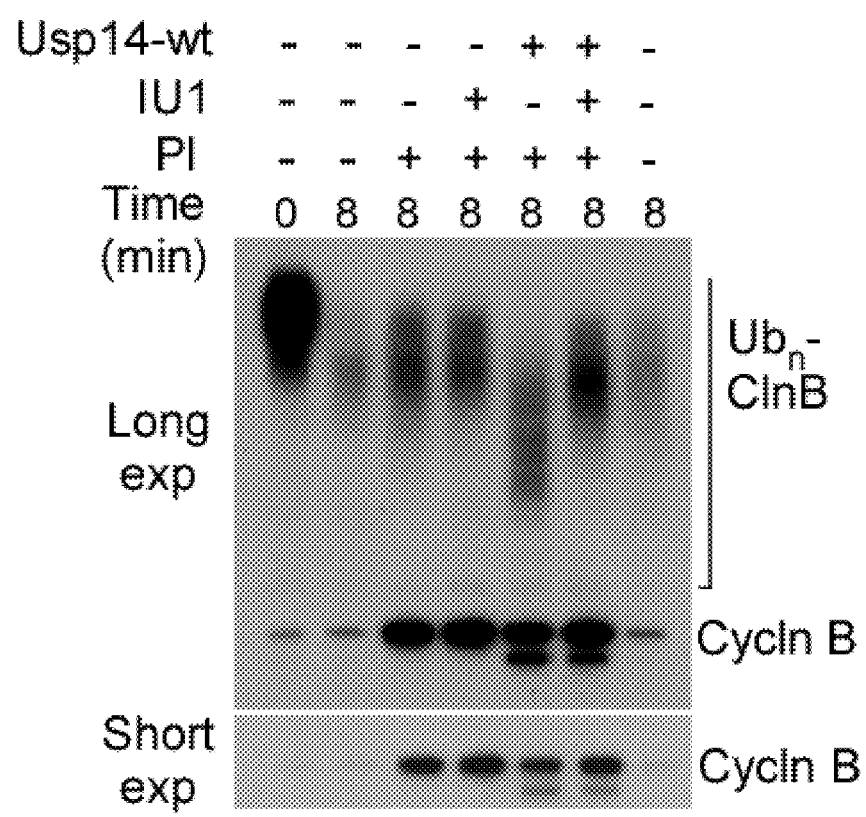

FIG. 15 shows an immunoblot that was performed using an antibody specific for Cyclin B and polyubiquitinated Cyclin B ($Ub_n$-ClbB) that had been treated with 4 nM of 26S human proteasome, either alone, with wild-type Usp14 (Usp14-wt), with IU1, and/or with proteasome inhibitor as indicated. The immunoblot was either subject to a long exposure (Long exp) or a short exposure (Short exp).

Figure 16A:
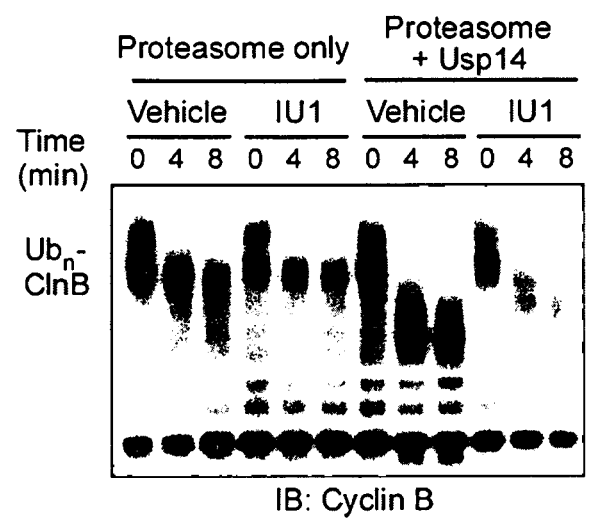

FIG. 16A shows an immunoblot that was performed using an antibody specific for Cyclin B and polyubiquitinated Cyclin B ($Ub_n$-ClbB) that had been treated with 4 nM of 26S human proteasome, either alone or in combination with wild-type Usp14 (60 nM) along with either vehicle or IU1 (34 μM).

Figure 16B:
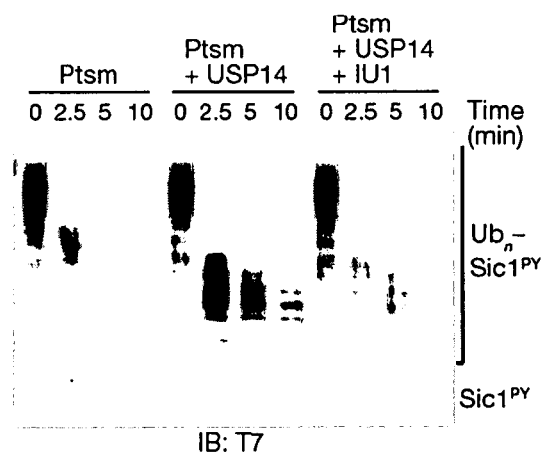

FIG. 16B shows an immunoblot that was performed using an antibody specific for T7-tagged $Sic1^{PY}$ and polyubiquitinated $Sic1^{PY}$ ($Ub_n$-$Sic1^{PY}$) that had been treated with 5 nM of 26S human proteasome, either alone or in combination with wild-type Usp14 (75 nM) along with either vehicle or IU1 (75 μM).

Figure 17:
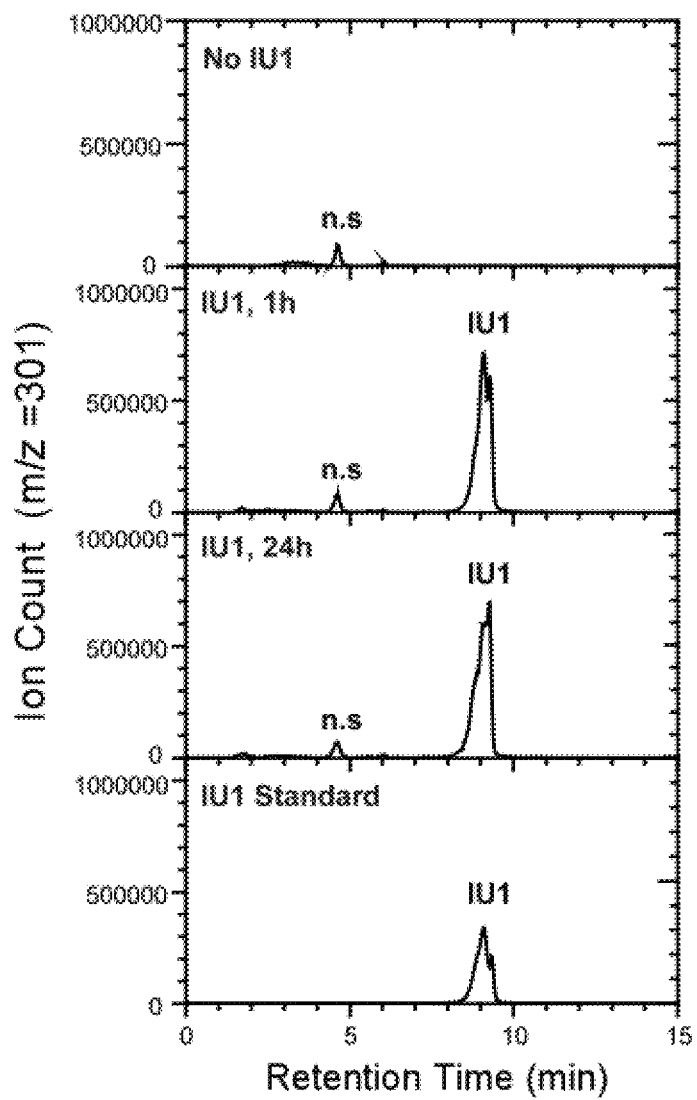

FIG. 17 shows plots depicting the ion counts of Liquid Chromatography/Mass Spectrometry (LC/MS) traces of lysates from MEF cells that had not been treated with IU1 (No IU1), or been treated with IU1 for 1 or 24 hours. The bottom panel depicts the ion count for an IU1 standard solution at 1 μg/mL.

Figure 18:
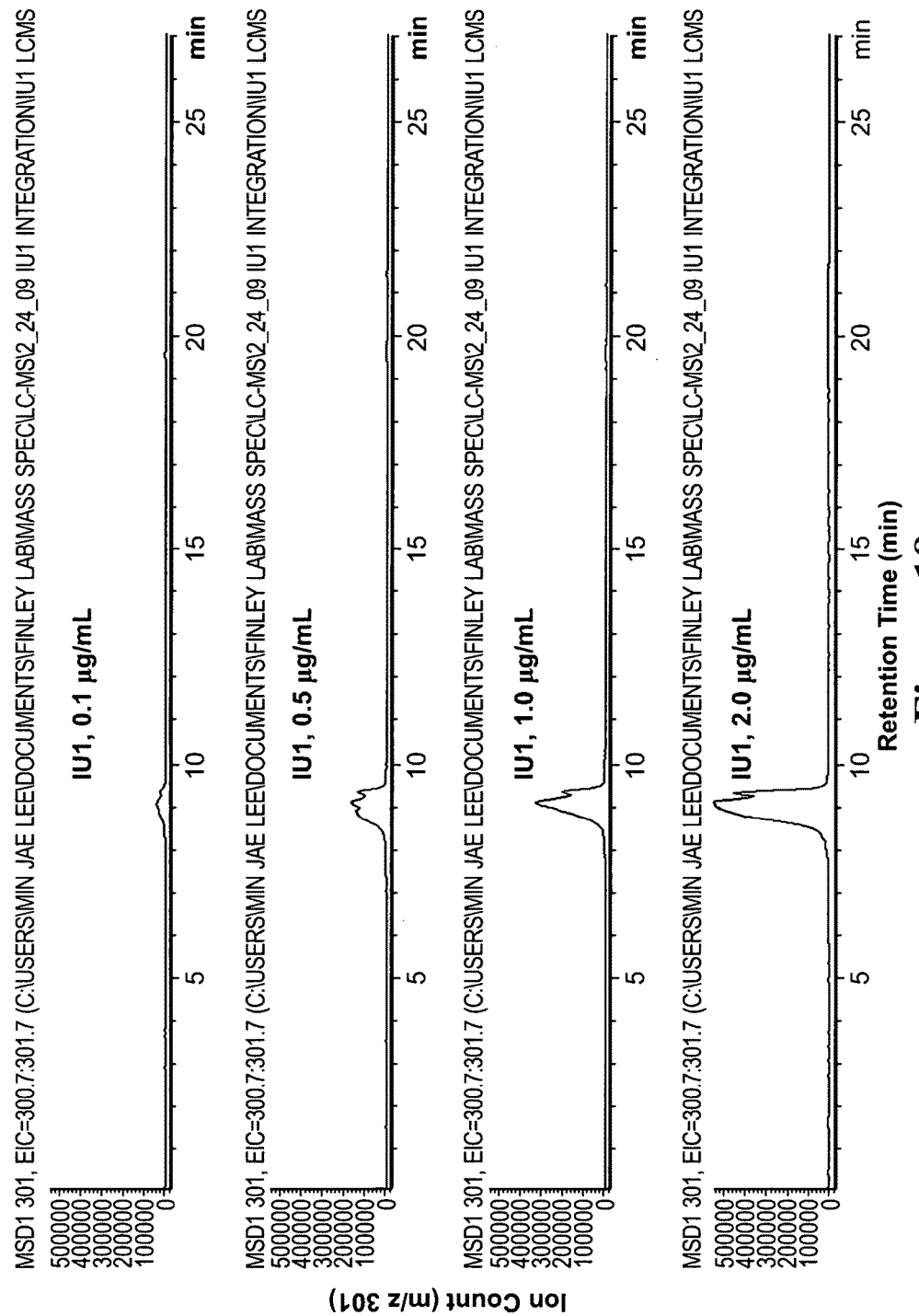

FIG. 18 shows plots depicting the ion counts of LC/MS traces of various concentrations of IU1 standard.

Figure 19:
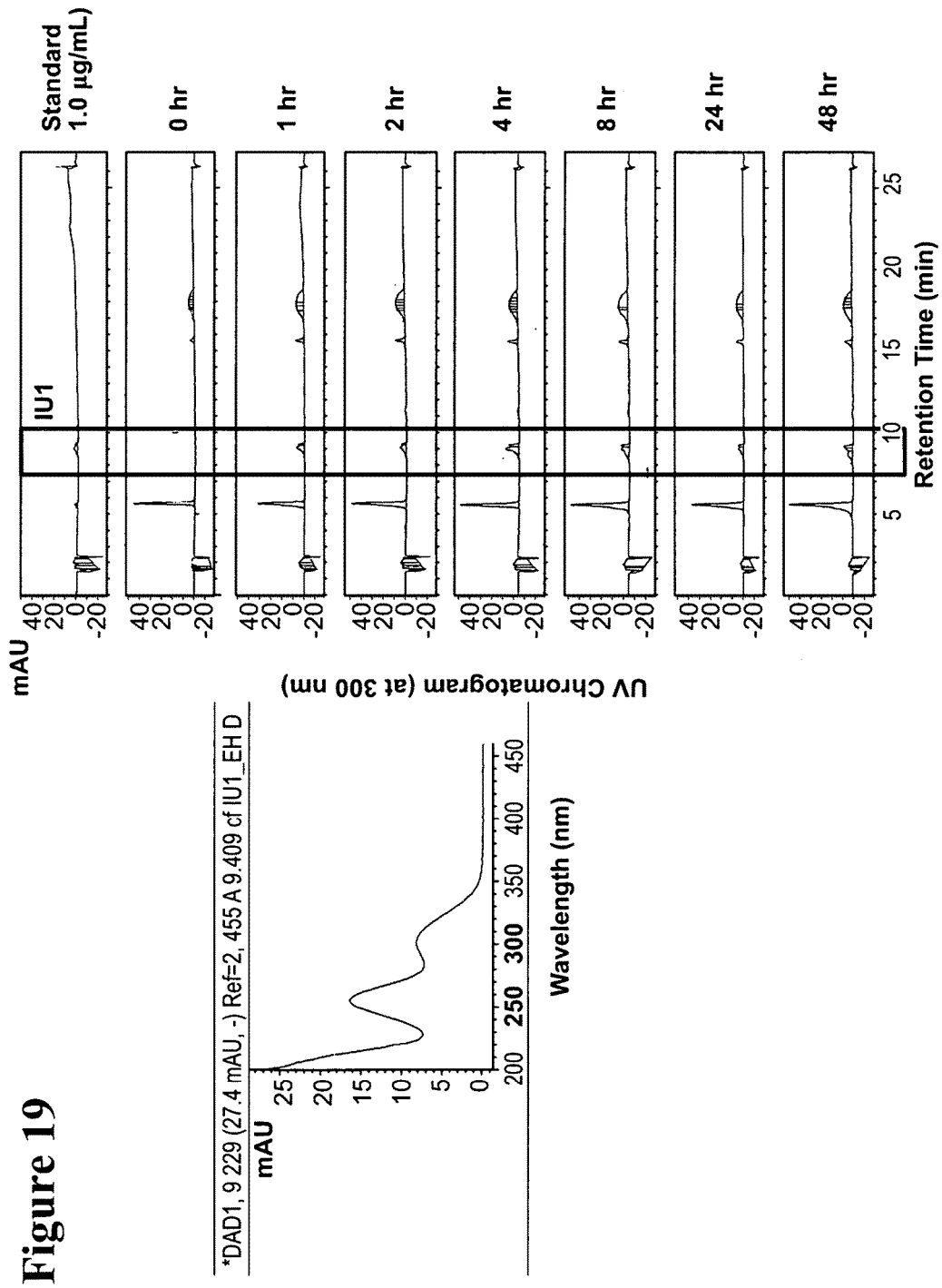

FIG. 19 shows the UV spectrum of IU1, depicting absorption maxima at 255 nm and 305 nm (left) and HPLC chromatograms showing the time-dependence of IU1 internalization into cells, followed at 300 nm (right).

Figure 20A:
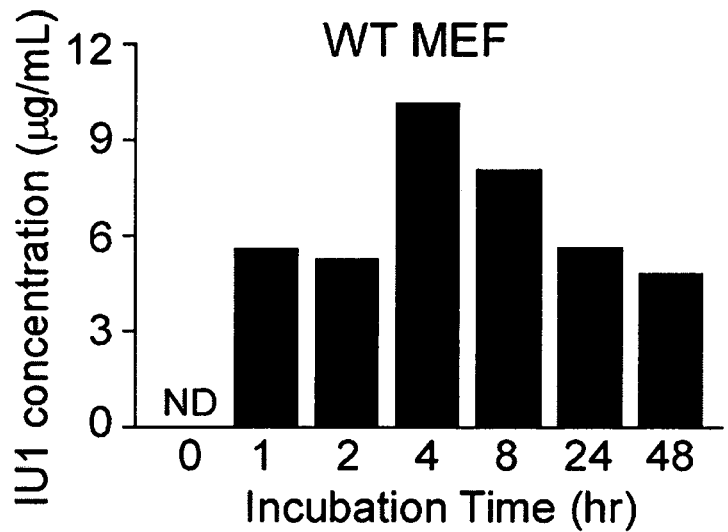

FIG. 20A shows a graph depicting the IU1 concentration in MEF cells after normalization by cell number as detected by UV absorption assay.

Figure 20B:
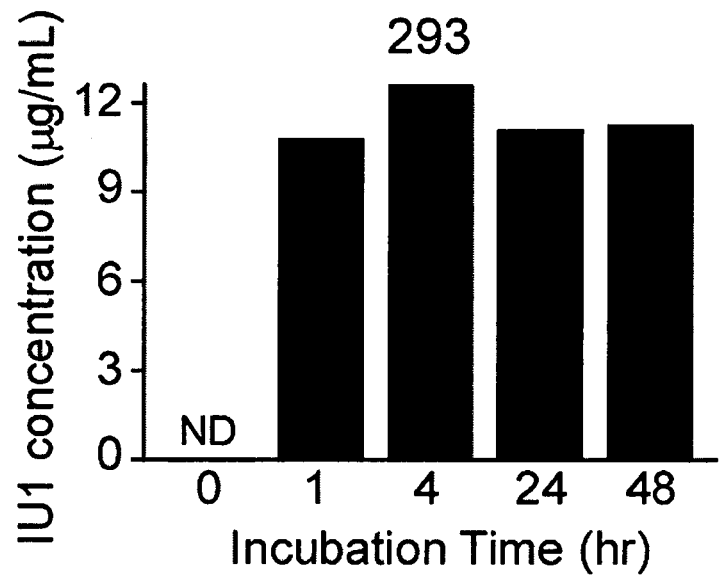

FIG. 20B shows a graph depicting the IU1 concentration in 293 cells after normalization by cell number as detected by UV absorption assay.

Figure 21A:
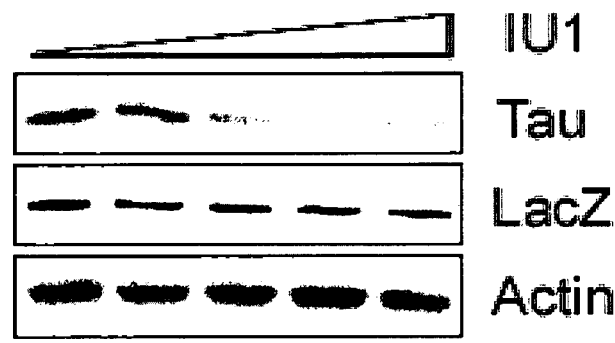

FIG. 21A shows immunoblots that were performed using lysates of MEF cells that co-expressed Tau and Usp14 and that were treated with 0, 25, 50, 75 or 100 μM IU1 and stained with antibodies specific for Tau, LacZ or Actin.

Figure 21B:
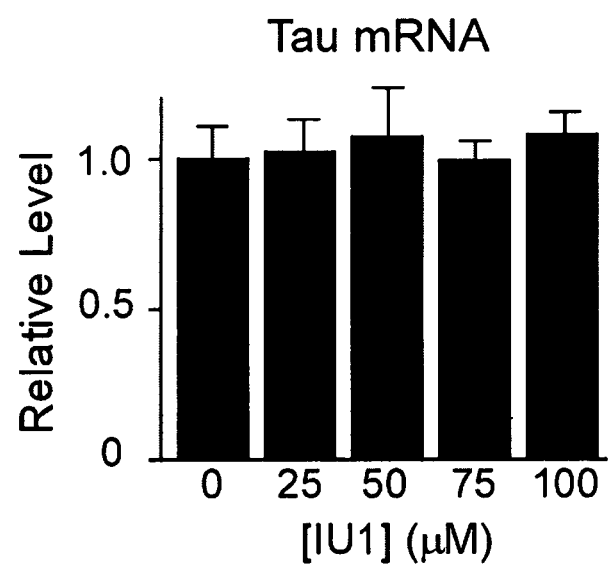

FIG. 21B shows the result of quantitative RT-PCR analysis of Tau RNA levels in MEF cells that co-expressed Tau and Usp14 and that were treated with 0, 25, 50, 75 or 100 μM IU1.

Figure 22A:
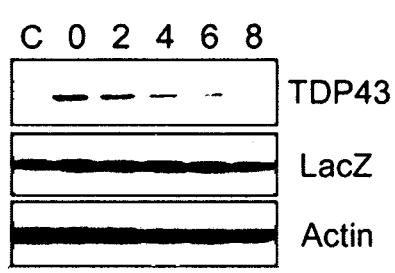

FIG. 22A shows immunoblots that were performed using lysates of MEF cells that co-expressed $TDP43^{flag}$ and Usp14 and that were treated with 75 μM IU1 for the indicated number of hours and stained with antibodies specific for $TDP43^{flag}$, LacZ or Actin.

Figure 22C:
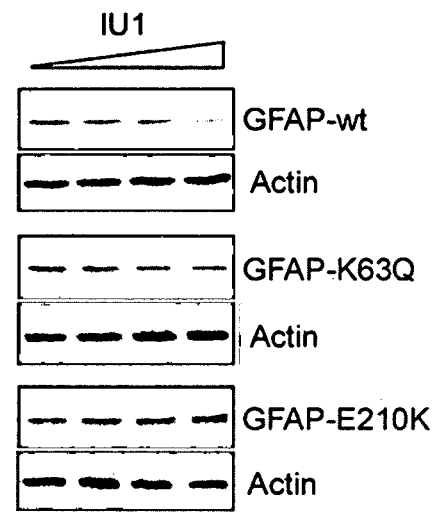
Figure 22B:
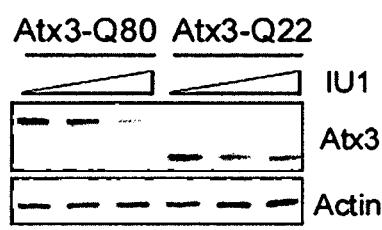

FIG. 22B shows immunoblots that were performed using lysates of MEF cells that co-expressed either Atx3-Q80 or Atx3-Q22 along with Usp14 and that were treated with 0, 50 or 100 μM IU1 and stained with antibodies specific for Atx3 or Actin.

FIG. 22C shows immunoblots that were performed using lysates of MEF cells that co-expressed either wild-type GFAP (GFAP-wt), K63Q mutant GFAP (GFAP-K63Q) or E210K GFAP (GFAP-E210K) along with Usp14 and that were treated with 0, 25, 50 or 100 μM IU1 and stained with antibodies specific for GFAP or Actin.

Figure 22D:
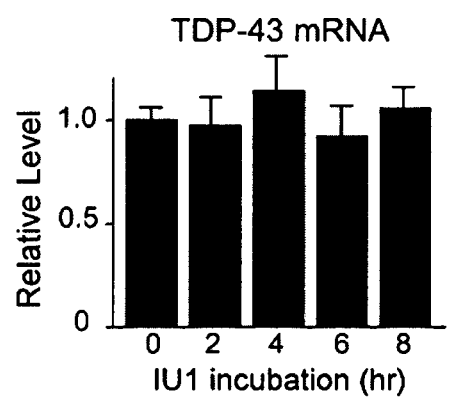

FIG. 22D shows the result of quantitative RT-PCR analysis of TDP-43 RNA levels in MEF cells that co-expressed TDP-43 and Usp-14 and that was treated with 75 μM IU1 for each indicated time.

Figure 23A:
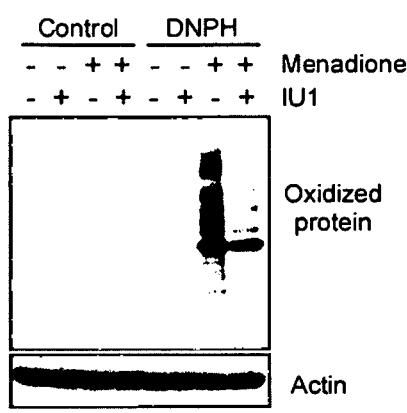

FIG. 23A shows immunoblots stained with anti-DNPH or anti-Actin antibodies that were performed on DNPH-treated lysates of MEF cells that were preincubated with vehicle or 75 μM IU1 and treated with 63 μM menadione, as indicated.

Figure 23B:
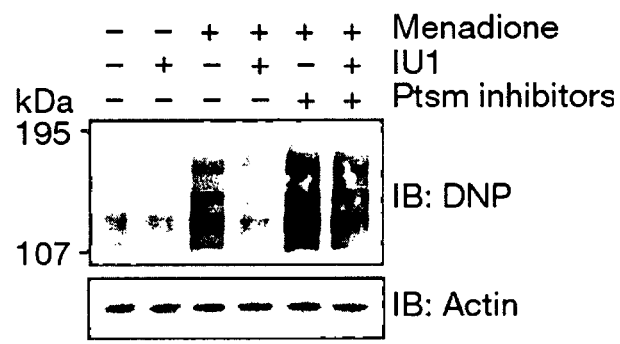

FIG. 23B shows immunoblots stained with anti-DNPH or anti-Actin antibodies that were performed on DNPH-treated lysates of HEK293 cells that were preincubated with IU1 (75 μM) or proteasome inhibitors (20 μM MG132, 10 μM PS-341) for 4 h, then treated with menadione (300 μM) for 60 min.

Figure 24:
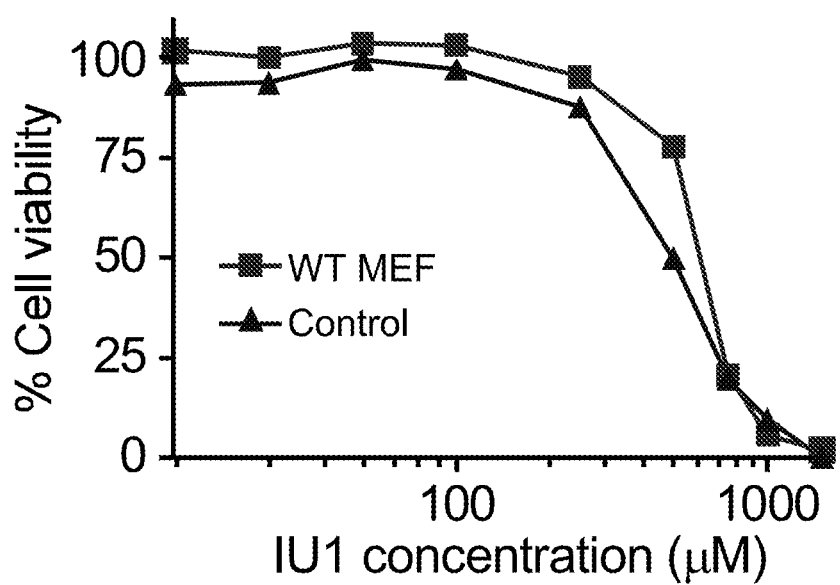

FIG. 24 shows a plot depicting MEF cell viability as assessed by MTT assay upon treatment with the indicated concentration of IU1 for 48 hours.

Figure 25A:
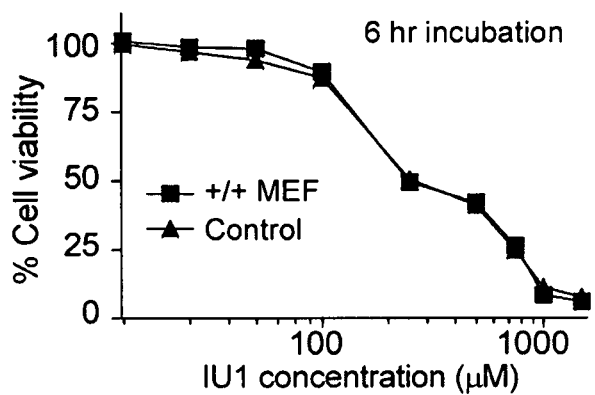

FIG. 25A shows a plot depicting MEF cell viability as assessed by MTT assay upon treatment with the indicated concentration of IU1 for 6 hours.

Figure 25B:
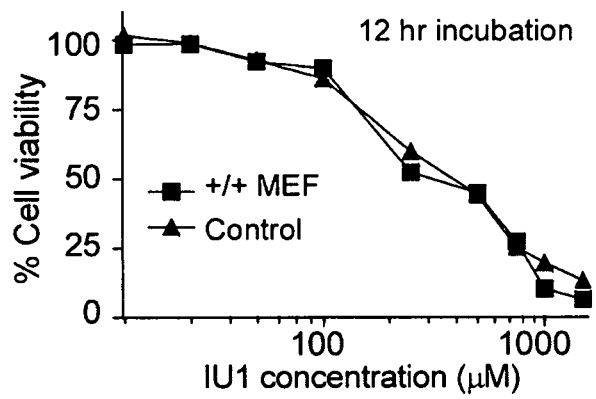

FIG. 25B shows a plot depicting MEF cell viability as assessed by MTT assay upon treatment with the indicated concentration of IU1 for 12 hours.

Figure 25C:
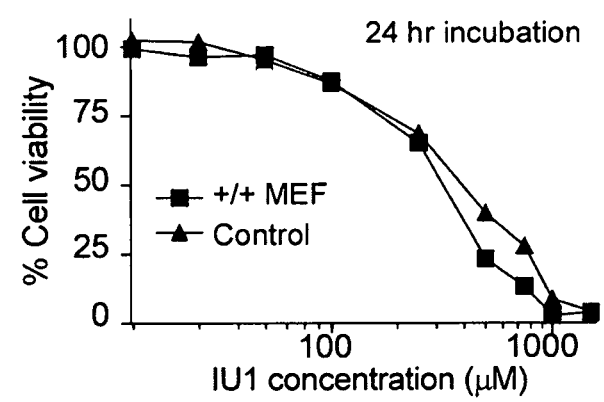

FIG. 25C shows a plot depicting MEF cell viability as assessed by MTT assay upon treatment with the indicated concentration of IU1 for 24 hours.

Figure 26A:
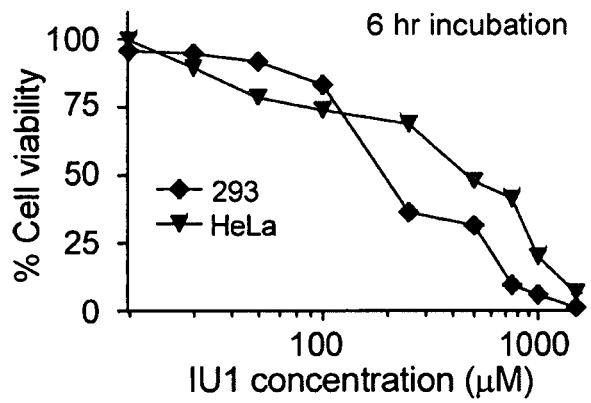

FIG. 26A shows a plot depicting 293 and HeLa cell viability as assessed by MTT assay upon treatment with the indicated concentration of IU1 for 6 hours.

Figure 26B:
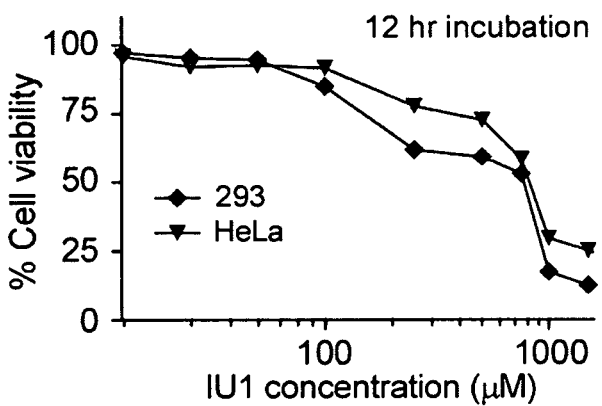

FIG. 26B shows a plot depicting 293 and HeLa cell viability as assessed by MTT assay upon treatment with the indicated concentration of IU1 for 12 hours.

Figure 26C:
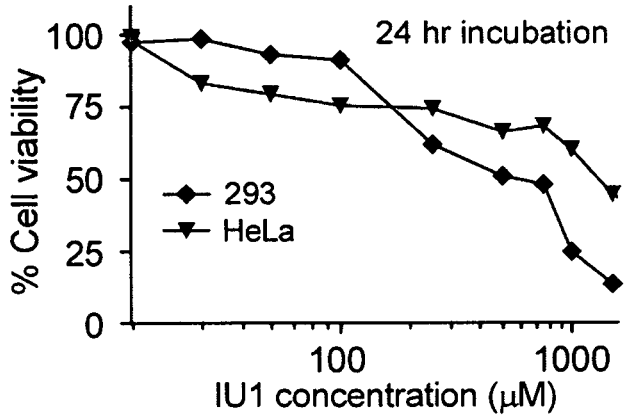

FIG. 26C shows a plot depicting 293 and HeLa cell viability as assessed by MTT assay upon treatment with the indicated concentration of IU1 for 24 hours.

Figure 27A:
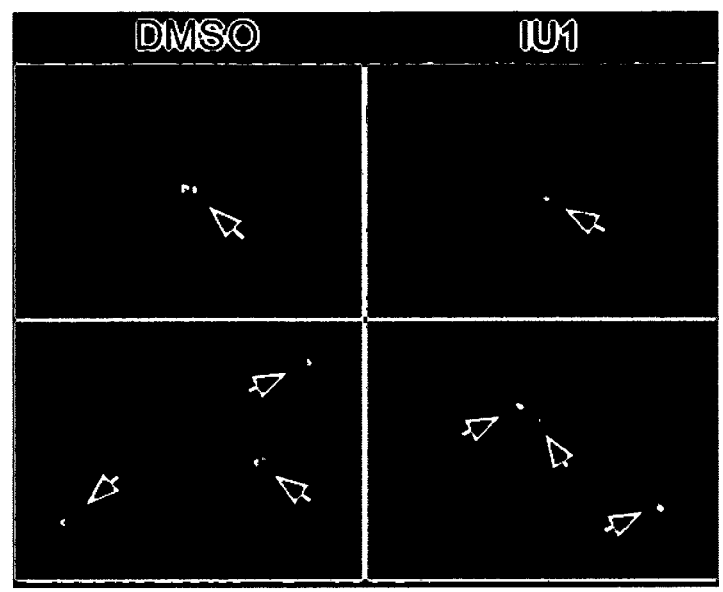

FIG. 27A shows fluorescent microscopy images of TUNEL stained MEF cells that had been treated with 100 μM IU1 or control for 6 hr.

Figure 27B:
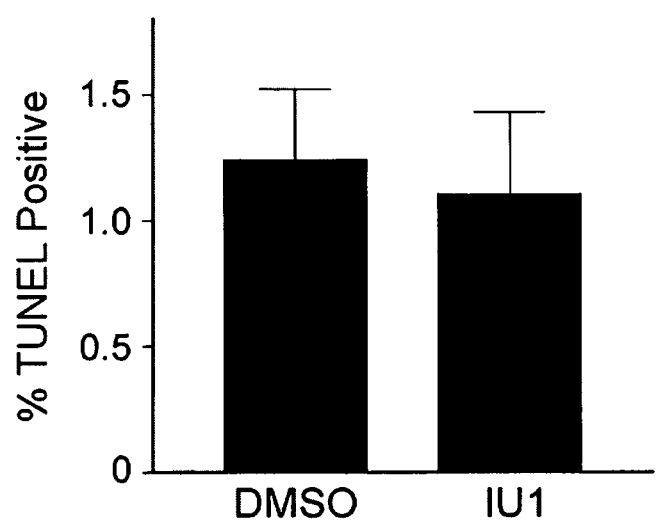
Figure 31:
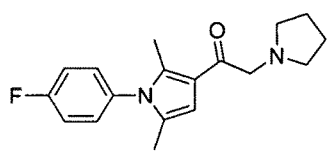
Figure 31:
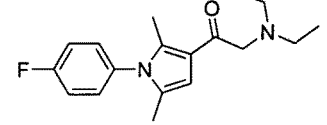
Figure 31:
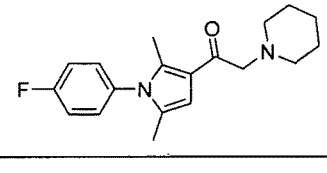
Figure 31:
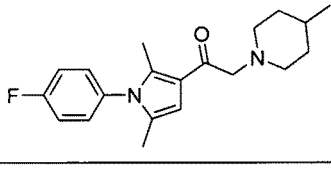
Figure 31:
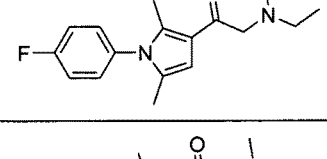
Figure 31:
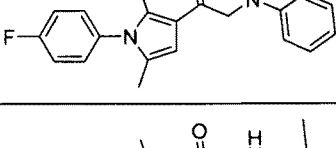
Figure 31:
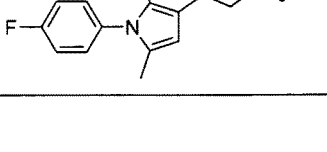
Figure 31:
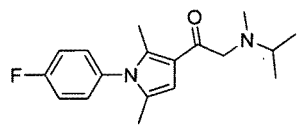
Figure 31:
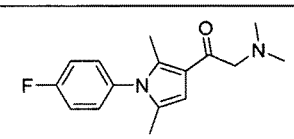
Figure 31:
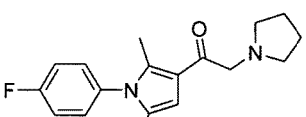
Figure 31:
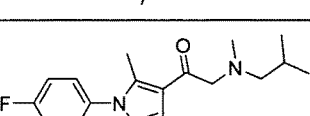
Figure 31:
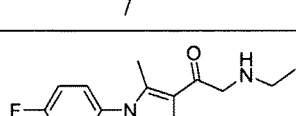
Figure 31:
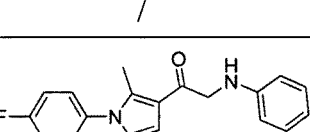
Figure 31:
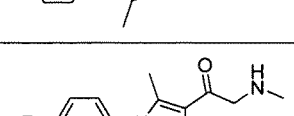
Figure 31:
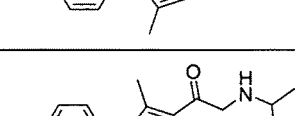
Figure 31:
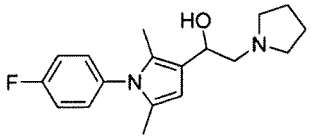
Figure 31:
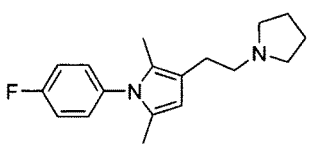
Figure 31:
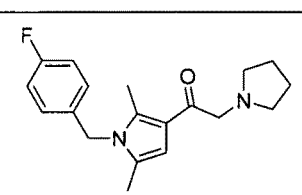
Figure 31:
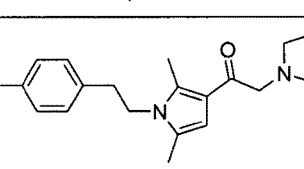
Figure 31:
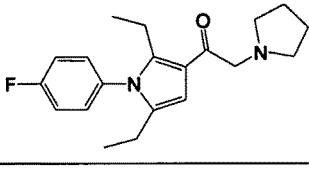
Figure 31:
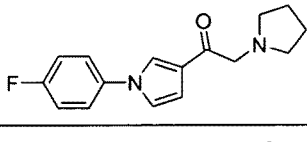
Figure 31:
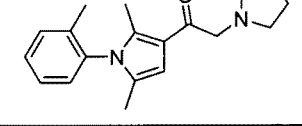
Figure 31:
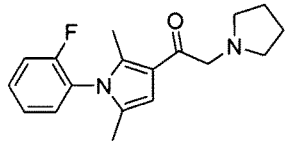
Figure 31:
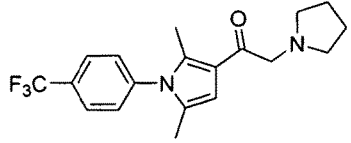
Figure 31:
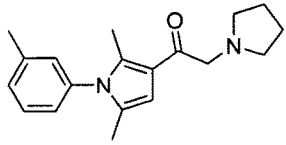
Figure 31:
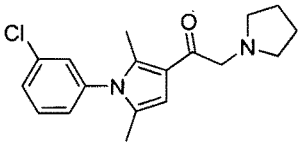
Figure 31:
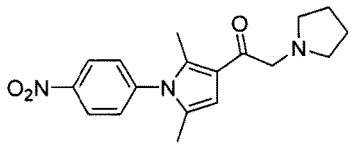
Figure 31:
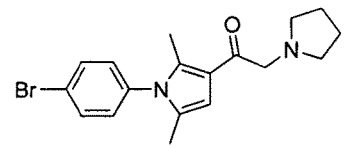
Figure 31:
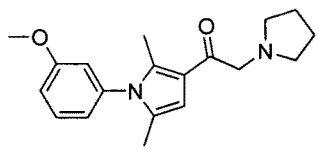
Figure 31:
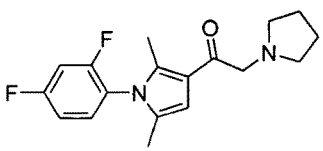
Figure 31:
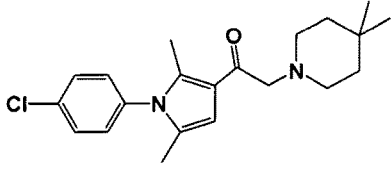
Figure 31:
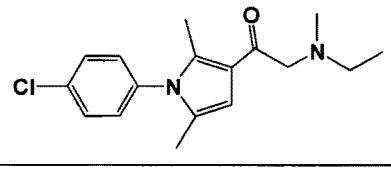
Figure 31:
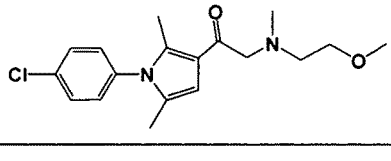
Figure 31:
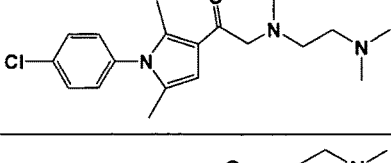
Figure 31:
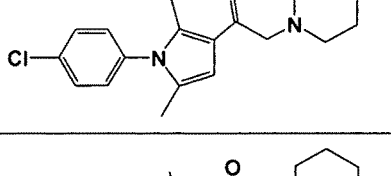
Figure 31:
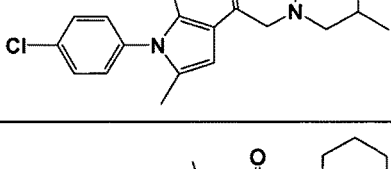
Figure 31:
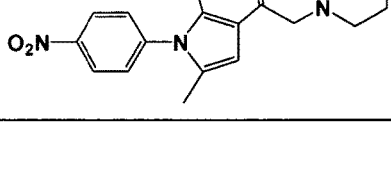
Figure 31:
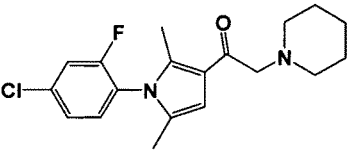
Figure 31:
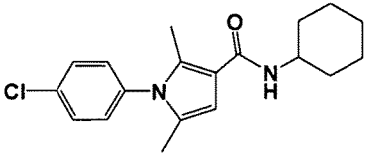
Figure 31:
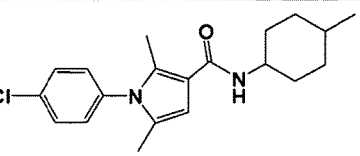
Figure 31:
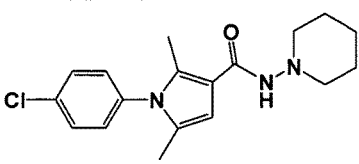
Figure 31:
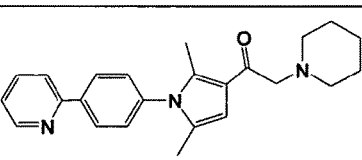
Figure 31:
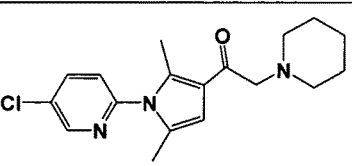
Figure 31:
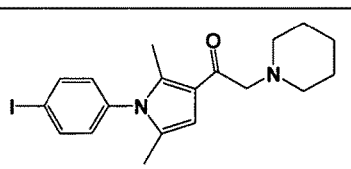
Figure 31:
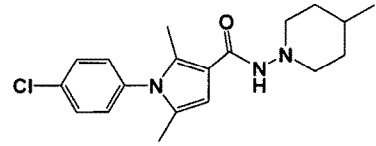
Figure 31:
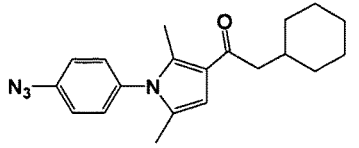
Figure 31:
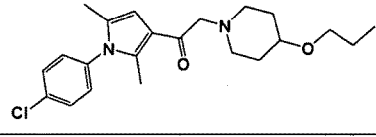
Figure 31:
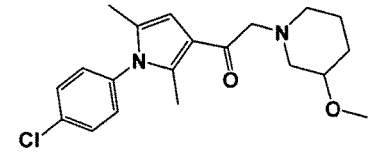
Figure 31:
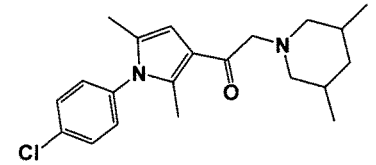
Figure 31:
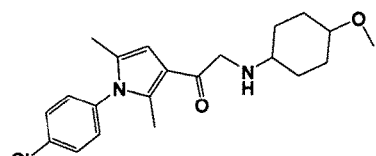
Figure 31:
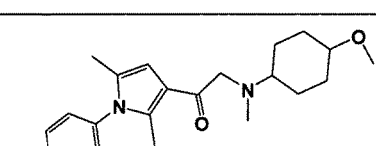
Figure 31:
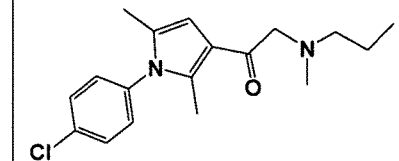
Figure 31:
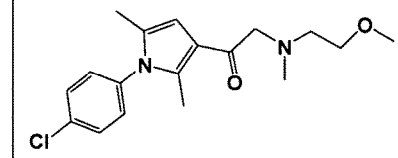
Figure 31:
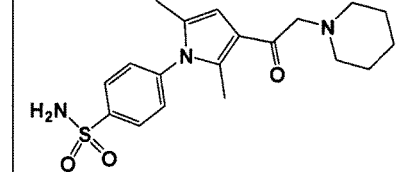
Figure 31:
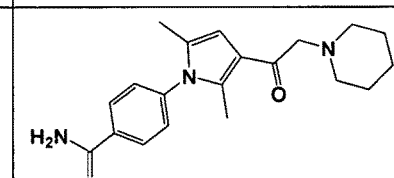
Figure 31:
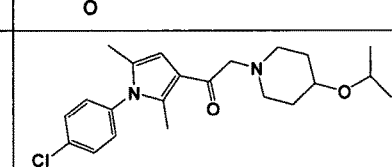
Figure 31:
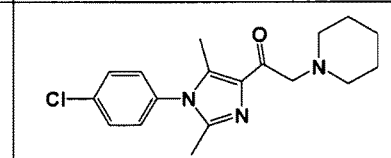
Figure 31:
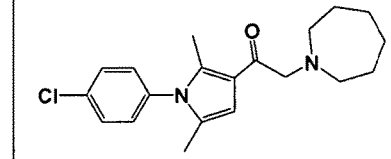
Figure 31:
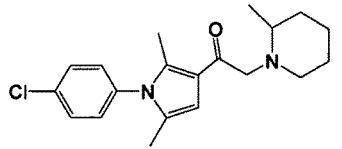
Figure 31:
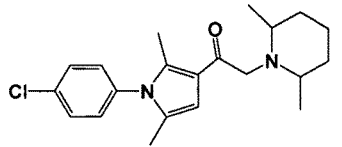
Figure 31:
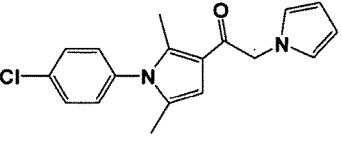
Figure 31:
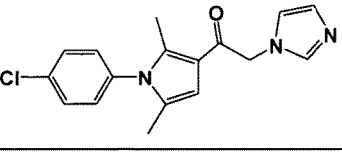
Figure 31:
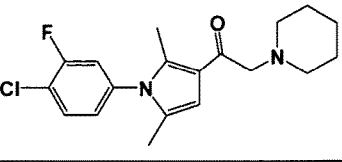
Figure 31:
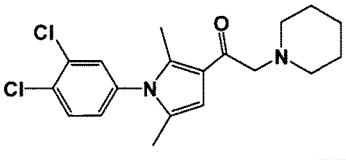
Figure 31:
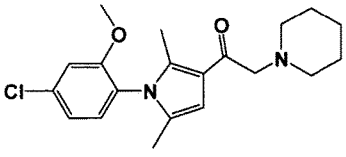
Figure 31:
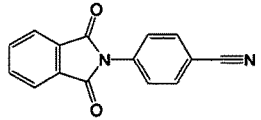
Figure 31:
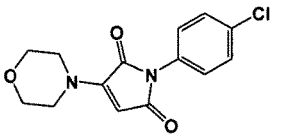
Figure 31:
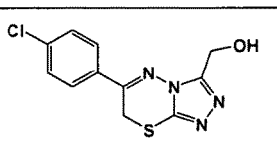
Figure 31:
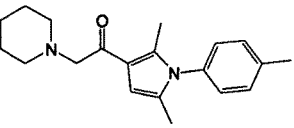
Figure 31:
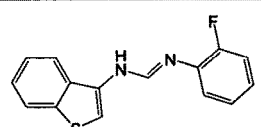
Figure 31:
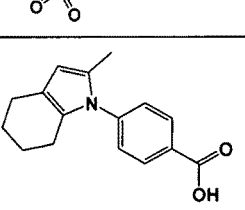
Figure 31:
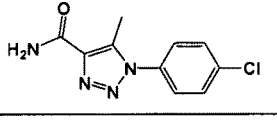
Figure 31:
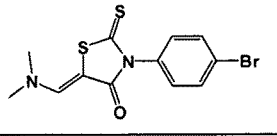
Figure 31:
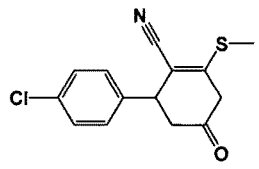
Figure 31A:
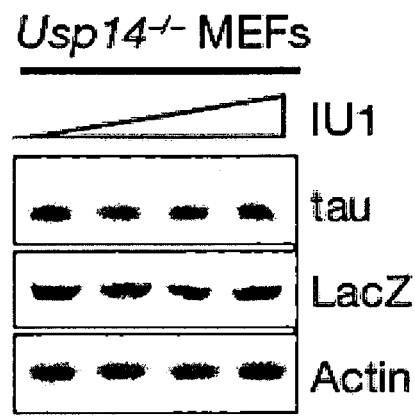

FIG. 27B shows a graph depicting the quantification of the TUNEL staining analysis depicted in FIG. 31A.

Figure 28:
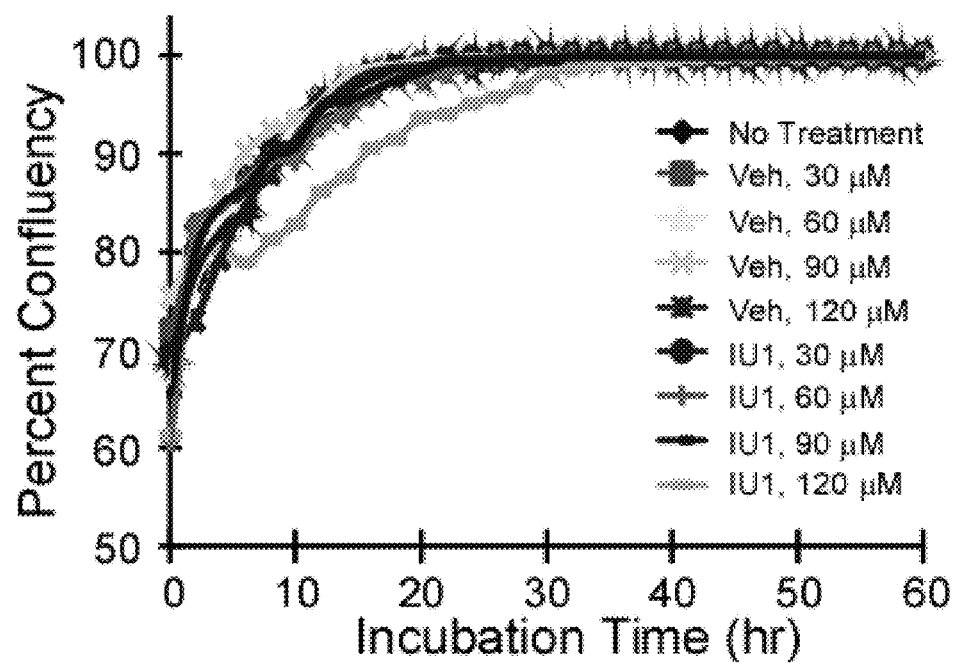

FIG. 28 shows a plot depicting the percent confluency of MEF cells that had been treated with the indicated concentration of vehicle or IU1 for the indicated period of time.

Figure 29:
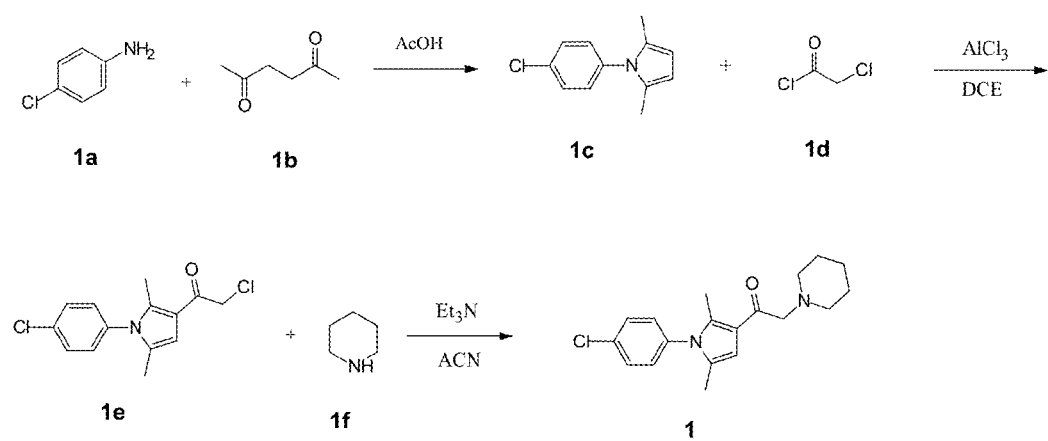

FIG. 29 depicts one approach to compounds of the invention.

Figure 30:
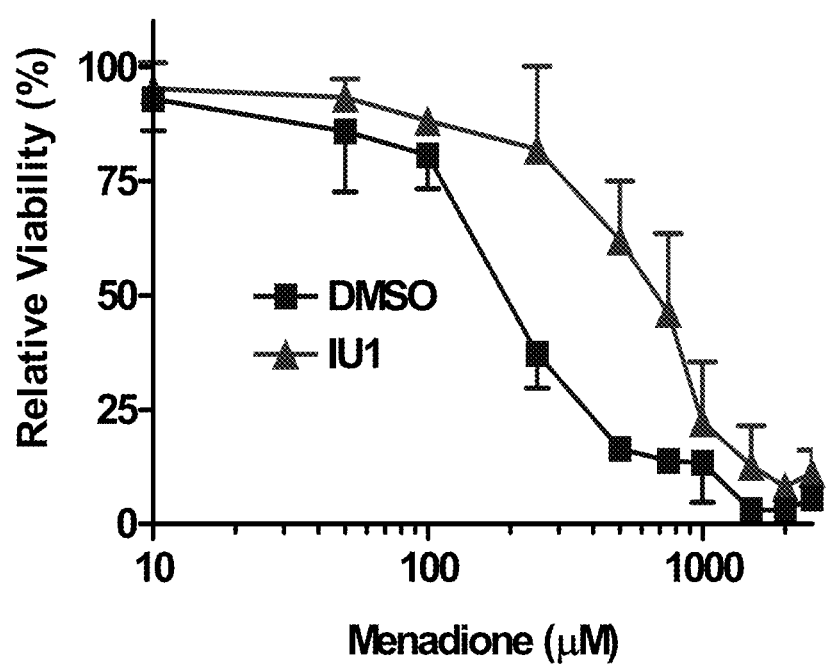

FIG. 30 depicts a graph showing MTT assay for cell viability; specifically, IU1 effects on cell survival upon oxidative stress. Experiment performed in HEK293 cells with Menadione (dose-dependent, 4 hr) and IU1 (50 uM, 6 hr). MEF cells show this effect as well. The effect on the $IC_{50}$ for menadione is almost 4-fold.

FIG. 31 depicts a table of selected compounds of the invention, including some percent inhibition and $IC_{50}$ values. Percent inhibition was measured at 8 μM from IU1-1 to IU-46, at 4 μM from IU1-47 to IU1-96, and at 17 μM for C'1 to C'9.

FIG. 31A shows immunoblots that were performed using lysates of Usp14−/− MEF cells that co-expressed tau and LacZ and that were treated with 0, 25, 50, 75 or 100 μM IU1 and stained with antibodies specific for tau, LacZ or Actin.

Figure 31B:
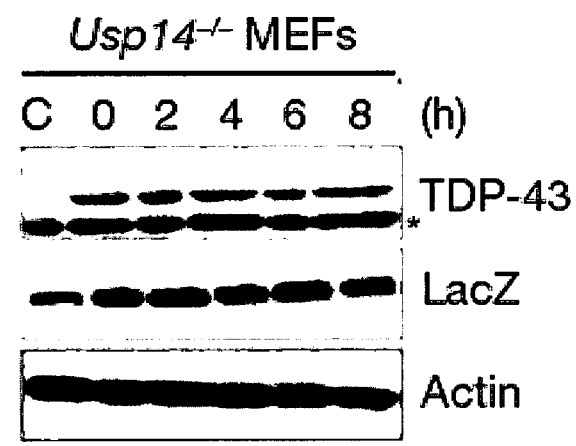

FIG. 31B shows immunoblots that were performed using lysates of Usp14−/− MEF cells that co-expressed TDP-43$^{flag}$ and LacZ and that were treated with 75 μM IU1 for the indicated number of hours and stained with antibodies specific for TDP-43$^{flag}$, LacZ or Actin.

Figure 32:
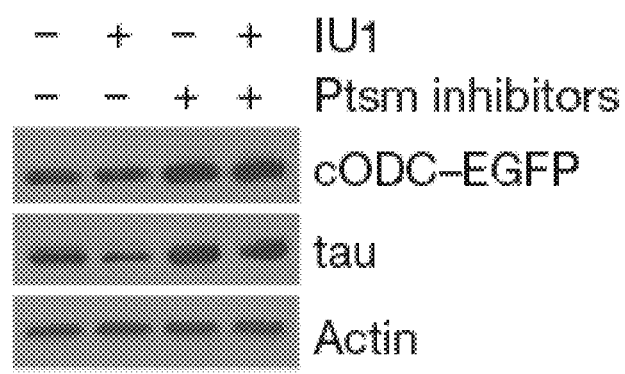

FIG. 32 shows immunoblots that were performed using lysates of wild-type MEF cells that co-expressed tau and Ub-independent proteasome substrate cODC-EGFP and that were incubated with 50 μM IU1 for 6 h and stained with antibodies specific for tau, cODC-EGFP or Actin. Proteasome inhibitors (30 μM MG132, 10 μM PS-341) were treated 4 hr before lysis.

Figure 33:
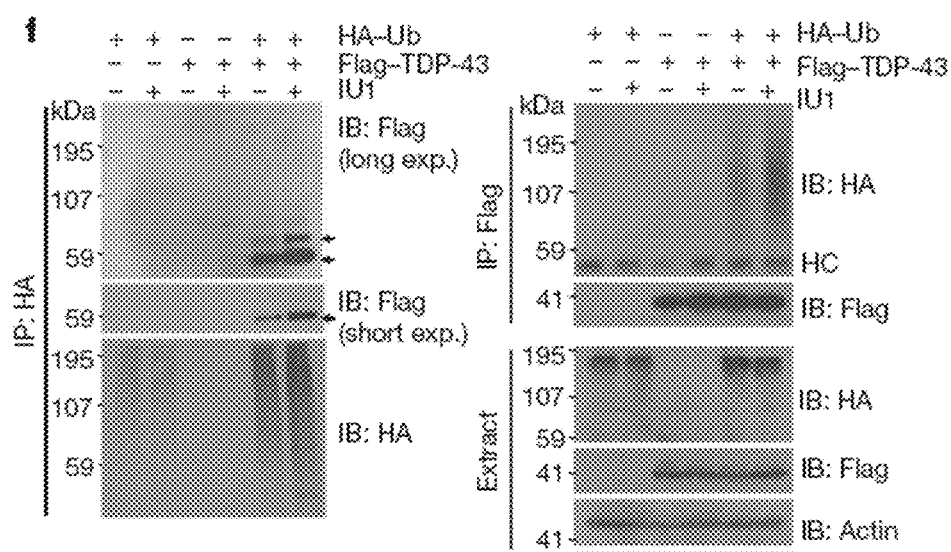

FIG. 33 shows immunoblots that were performed using lysates of wild-type MEF cells that co-expressed HA-tagged Ub and/or Flag-tagged TDP-43 and that were incubated with 50 μM IU1 for 6 hr and stained with antibodies specific for Flag-TDP-43, HA-Ub, or Actin. Proteasome inhibitors (20 μM MG132, 10 μM PS-341) were added 4 hr before lysis. Arrows indicate likely ubiquitinated TDP-43 species. HC, heavy chain of antibody.

Figure 34A:
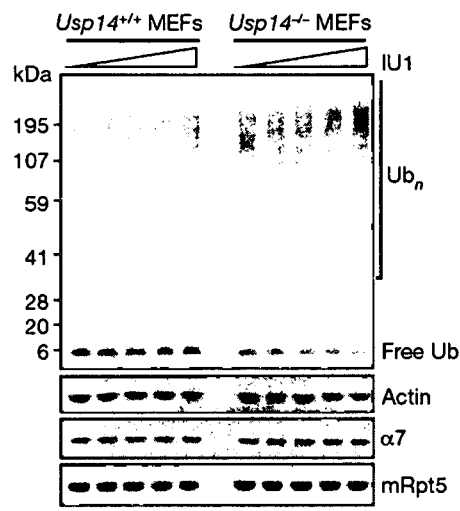

FIG. 34A shows immunoblots that were performed using lysates of wild-type or Usp14$^{-/-}$ MEF cells that were treated with IU1 (0, 25, 50, 75, or 100 μM) for 6 hr and stained with antibodies specific for Ub, Actin, CP subunit α7, or RP subunit mRPT5.

Figure 34B:
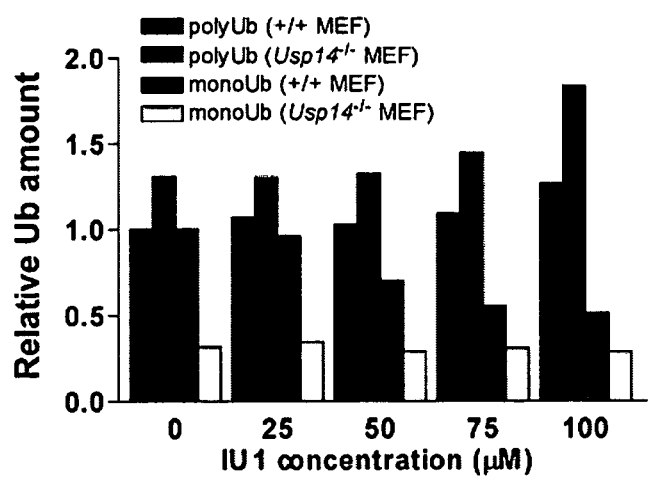

FIG. 34B shows quantification of ubiquitin levels in FIG. 34A. Polyubiquitin and monoubiquitin levels from wild-type and Usp14$^{-/-}$MEF cells were quantified after treatment of various concentration of IU1. Ub signals were normalized to that of endogenous actin. Quantification was achieved by densitometry of a film image (left bar=poly UB (+/+MEF); second bar to the left=poly Ub (Usp14$^{-/-}$MEF); third bar=mono Ub (+/+MEF); right bar=mono Ub (Usp14$^{-/-}$ MEF)).

Figures 35A, 35B:
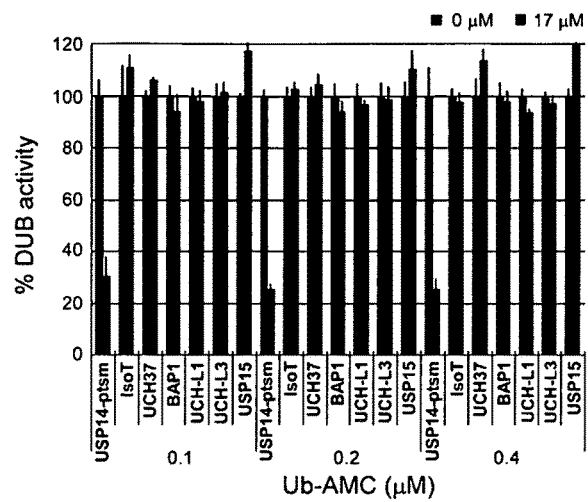

FIG. 35A shows the specificity of IU1 for USP14 which is observed independently of Ub-AMC concentration. Assays of Ub-AMC hydrolysis were done as in FIG. 11B, except lower concentrations of Ub-AMC were used (left bar=0 μM; right bar=17 μM).

FIG. 35B shows the summary of $K_M$ values for Ub-AMC of deubiquitinating enzymes in this study. $K_M$ values of DUBs used in the selectivity assays were obtained from the literature. Unknown $K_M$ values were determined in this study, as indicated. These values are significant because the DUB assays should be most sensitive to inhibition when substrate is at a low concentration as compared to the $K_M$ of the enzyme in question. CD, catalytic domain.

Figure 36:
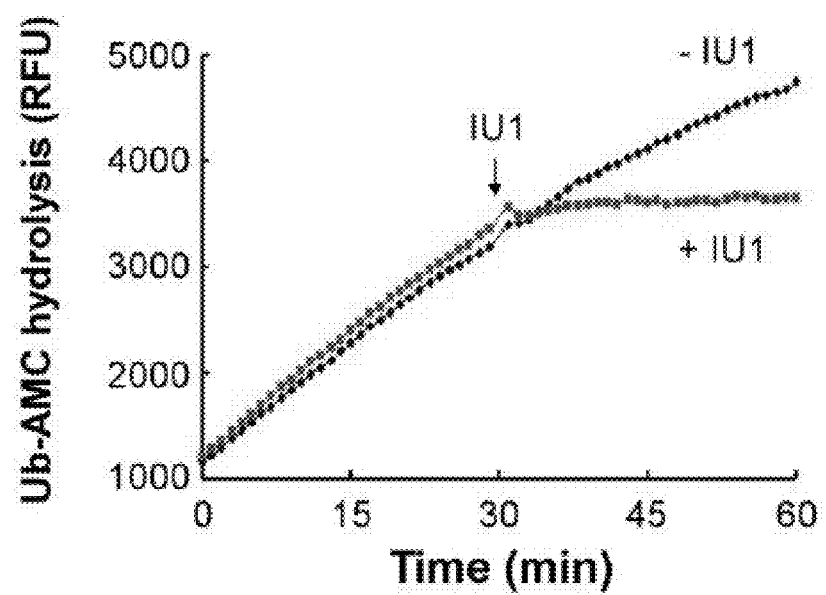

FIG. 36 shows that IU1 inhibits proteasome-associated USP14 activity without a detectable lag period. 2.5 nM of human proteasome was mixed with 30 nM of recombinant USP14 protein. The reaction was then initiated by adding 1 μM Ub-AMC. After 30 min, IU1 (100 μM) or vehicle (DMSO) was added to the sample.

Figure 37:
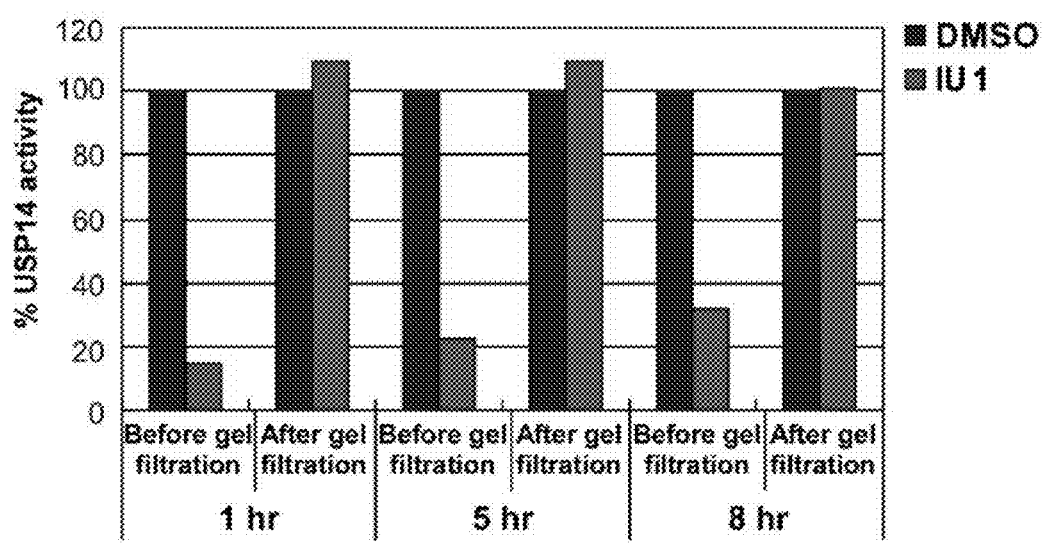

FIG. 37 confirms FIG. 13, except prolonged incubation (5 and 8 hr) was tested. The percent USP14 activity was normalized to 26S peptidase activity (i.e. LLVY-AMC hydrolysis). IU1 was added to 100 μM (left bar=DMSO; right bar=IU1).

Figure 38:
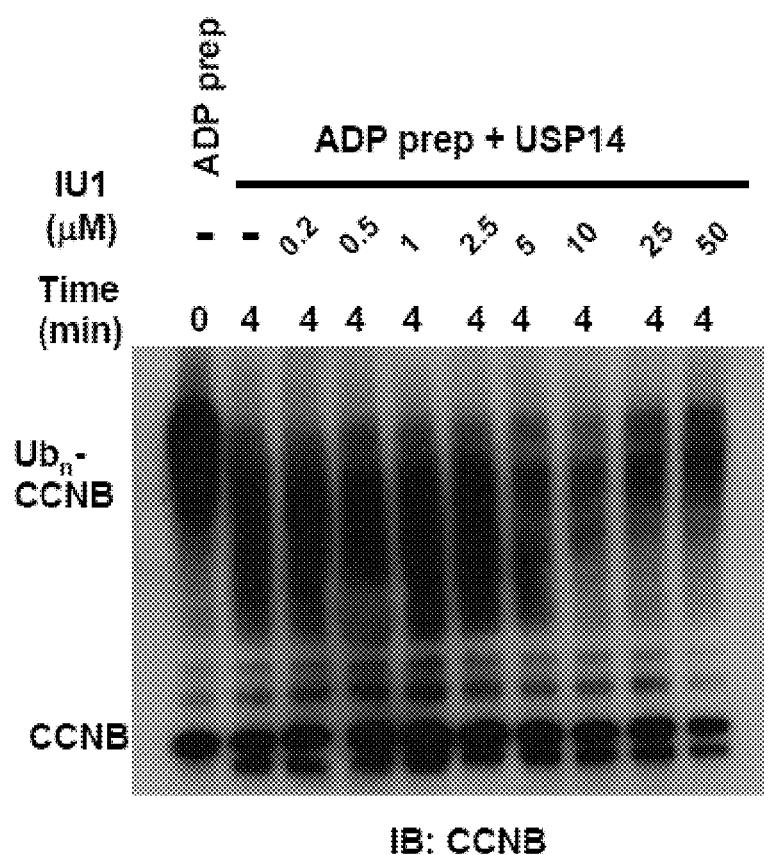

FIG. 38 shows in vitro chain trimming assays that were performed with human proteasome purified in the presence of ADP (ADP prep) and assayed in the presence of ADP. Immunoblot was performed using an antibody specific for human cyclin B (CCNB). IU1 is effective at inhibition of chain trimming at approximately 5 µM, as expected from Ub-AMC hydrolysis data.

Figure 39:
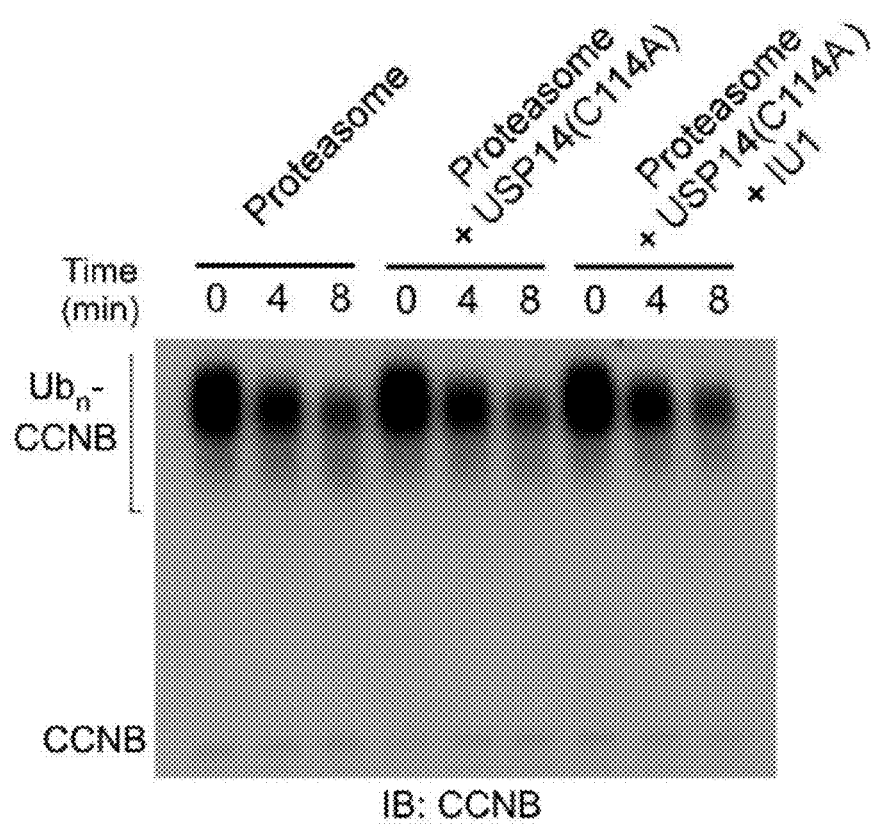

FIG. 39 shows that IU1 does not affect cyclin B degradation in the presence of USP14-CA. Assays were done as in FIG. 5.

Figure 40A:
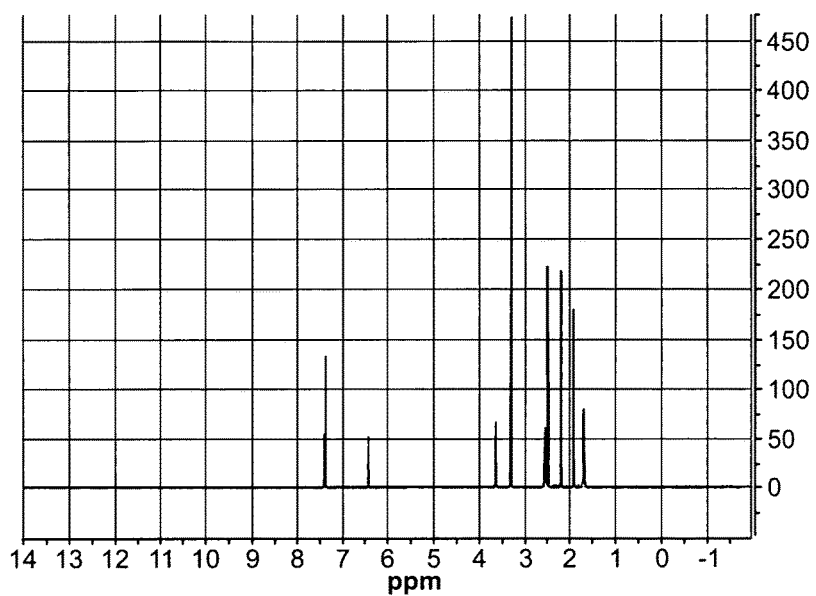

FIG. 40A shows $^1$H-NMR spectroscopic data of IU1.

Figure 40B:
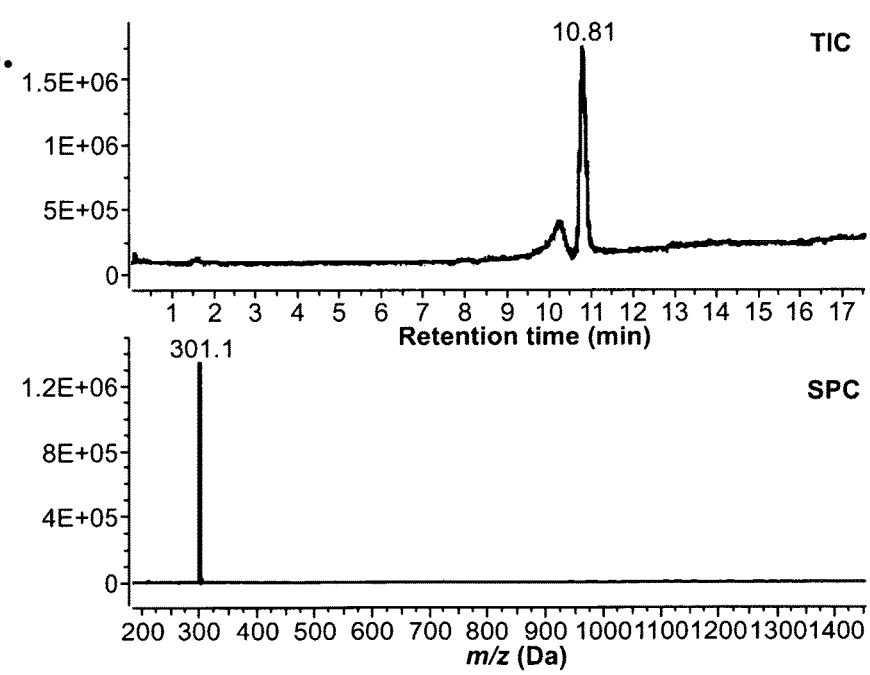

FIG. 40B shows LC/MS analysis of IU1. TIC, total ion count. SPC, shared peak count extracted from the peak with the indicated retention time.

Figure 41A:
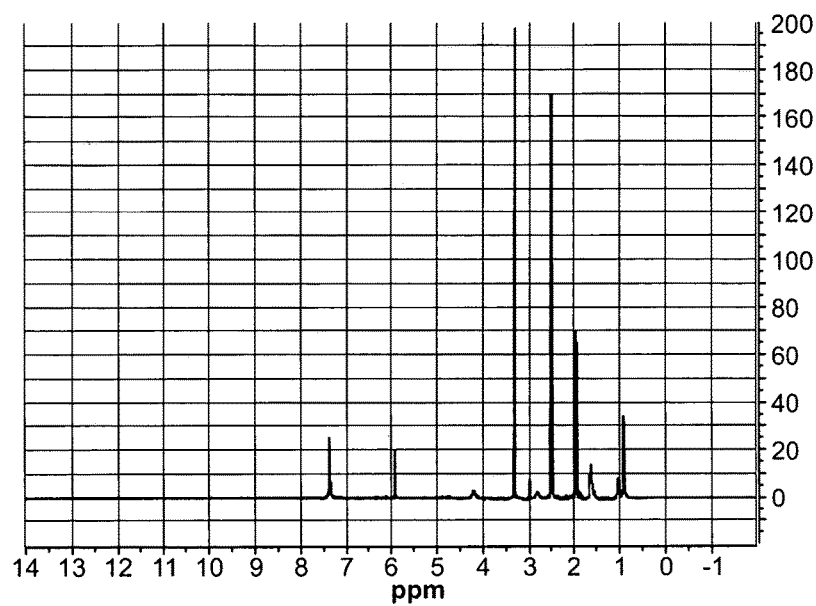

FIG. 41A shows $^1$H-NMR spectroscopic data of IU1C.

Figure 41B:
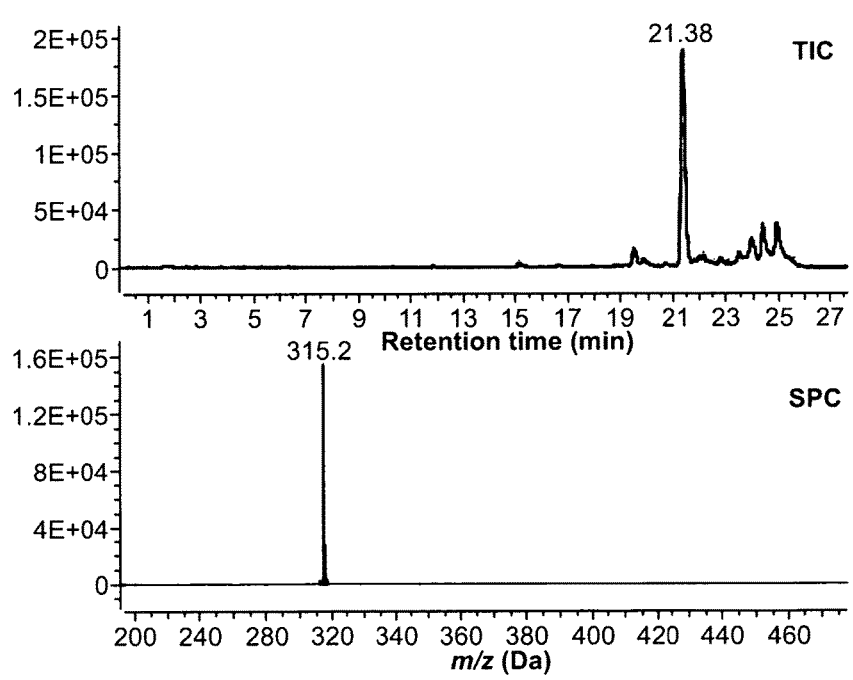

FIG. 41B shows LC/MS analysis of IU1C. TIC, total ion count. SPC, shared peak count extracted from the peak with the indicated retention time.

Figure 42A:
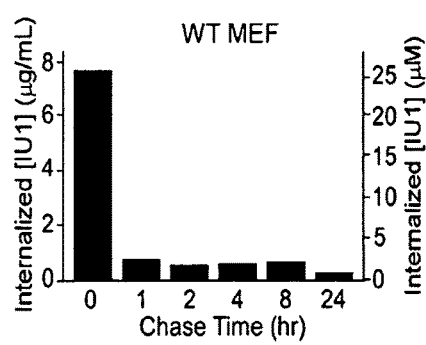

FIG. 42A shows a graph depicting rapid release of the internalized IU1 from wild-type MEF cells. After wild-type MEFs were incubated with 50 µM of IU1 for one hour, the culture media were replaced with fresh media without IU1. Internalized IU1 was monitored at the indicated times and its concentration was normalization by cell number as detected by UV absorption assay.

Figure 42B:
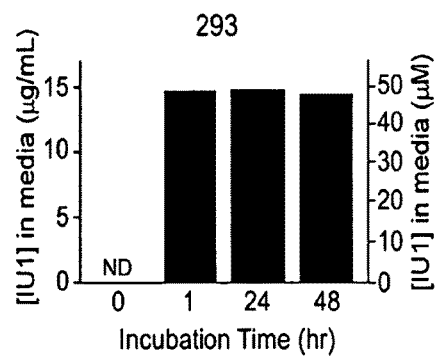

FIG. 42B shows the comparable concentration of IU1 from 1 hr to 48 hr in the serum-containing media of HEK293 cells.

Figure 42C:
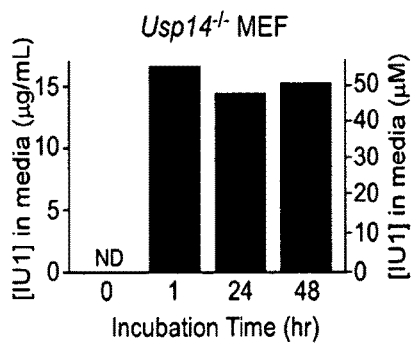

FIG. 42C shows the comparable concentration of IU1 from 1 hr to 48 hr in the serum-containing media of Usp14$^{-/-}$MEF cells.

Figure 43A:
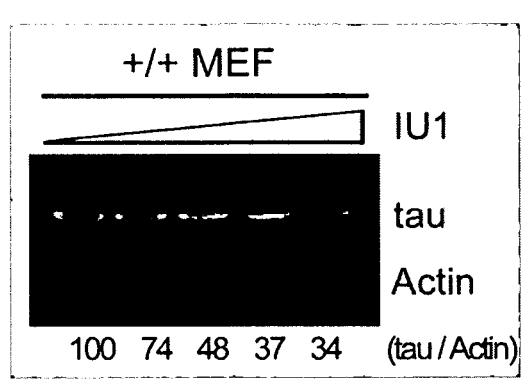

FIG. 43A shows the quantitative analysis of tau levels after IU1 treatment in wild-type MEFs. Quantification was performed with infrared dye-conjugated secondary antibodies using Odyssey imaging system. Tau signal intensities were normalized to that of endogenous actin and relative amounts are shown.

Figure 43B:
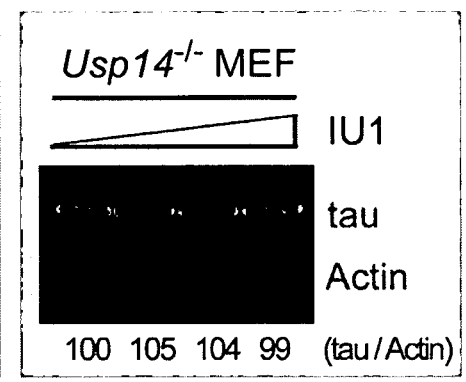

FIG. 43B shows the quantitative analysis of tau levels after IU1 treatment in Usp14$^{-/-}$ MEFs. Quantification was performed as in FIG. 43A.

Figure 44A:
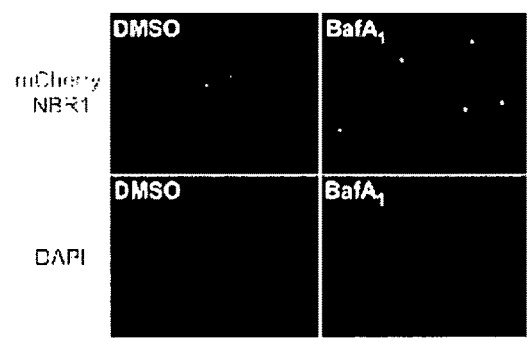

FIG. 44A shows that the immunofluorescence signal of transiently expressed mCherry-NBR1 (top row) was significantly increased after treatment with 200 µM of bafilomycin A$_1$ (BafA$_1$), an autolysosome formation inhibitor, for 6 hr in wild-type MEFs.

Figure 44B:
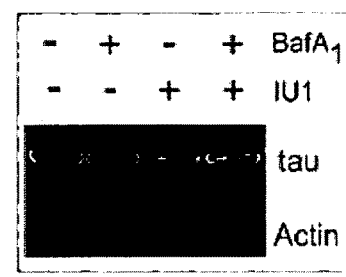

FIG. 44B shows that the stimulation of tau degradation by IU1 is not mediated by autophagy. Wild-type MEF cells were transfected with a plasmid expressing tau and then treated with 200 µM of BafA$_1$ and/or 75 µM of IU1 for 6 hrs, and analyzed by SDS-PAGE/immunoblot using the Odyssey infrared imaging system.

Figure 44C:
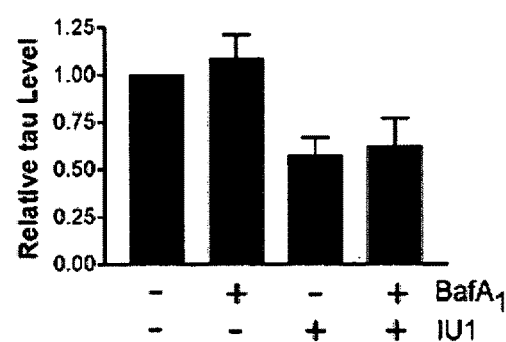

FIG. 44C shows the quantification of normalized tau protein level from three independent experiments (mean±SD) as performed in FIG. 44B using Odyssey software.

Figure 45A:
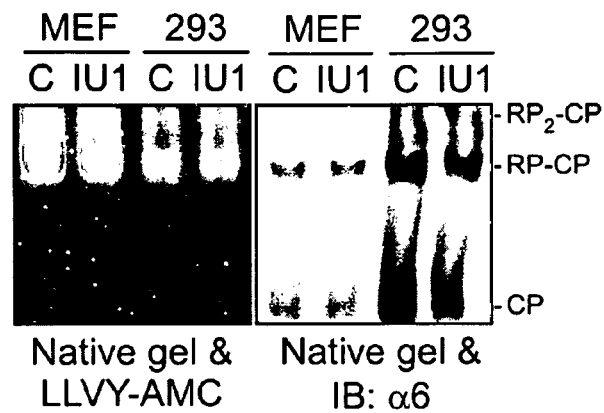

FIG. 45A shows that IU1 treatment does not affect the integrity of proteasome. Total cell extracts (50 µg/lane) before and after a 6-hr IU1 treatment (100 µM) were resolved by native PAGE, and the proteasome was visualized using either an in-gel activity stain with a fluorogenic peptide substrate (LLVY-AMC), or immunoblotting with antibodies specific to subunit α6. RP$_2$-CP and RP-CP indicate distinct forms of the 26S proteasome.

Figure 45B:
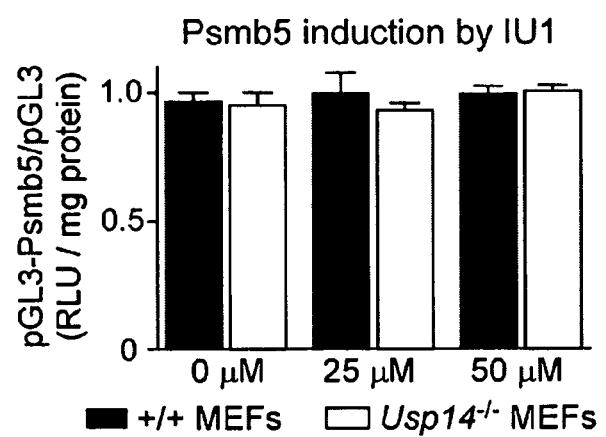

FIG. 45B shows that IU1 treatment does not induce the transcription of Psmb5 gene, a proteasome subunit. A luciferase reporter gene containing the murine Psmb5 promoter (−1 kb to 0 kb) was transiently expressed in wild-type and Usp14$^{-/-}$ MEFs and promoter activity was assessed following incubation of 25 or 50 µM of IU1 for 8 hr. For normalization of luciferase activity, a control experiment using the promoter-less pGL3 plasmid was performed. Values are mean±SD from three independent experiments. RLU, relative light units.

FIG. 45C shows that IU1 treatment does not induce the transcription of UbB, a ubiquitin gene. Quantitative RT-PCR was performed using total mRNA from +/+(left panels) and Usp14$^{-/-}$ MEFs (right) after incubation with a graded doses of IU1 for 6 hr.

FIG. 45D shows that IU1 treatment does not induce the transcription of α6, a proteasome subunit. Quantitative RT-PCR was performed using total mRNA from +/+(left panels) and Usp14$^{-/-}$ MEFs (right) after incubation with a graded doses of IU1 for 6 hr.

FIG. 45E shows that IU1 treatment does not induce the transcription of α7, a proteasome subunit. Quantitative RT-PCR was performed using total mRNA from +/+(left panels) and Usp14$^{-/-}$ MEFs (right) after incubation with a graded doses of IU1 for 6 hr.

Figure 46A:
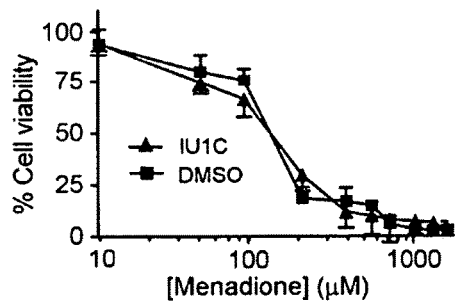

FIG. 46A depicts a graph showing MTT assay for cell viability; specifically, IU1C effects on cell survival upon oxidative stress. Experiment performed in HEK293 cells with Menadione (dose-dependent, 4 hr) and IU1C (50 uM, 6 hr).

Figure 46B:
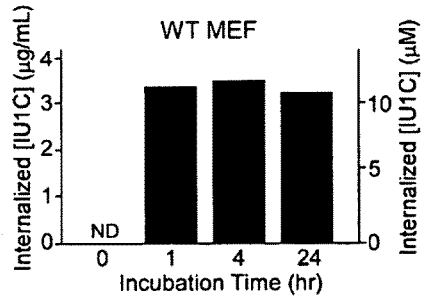

FIG. 46B shows a graph depicting the internalized IU1C concentration in wild-type MEF cells. After the indicated time-course treatment of 50 uM of IU1C, IU1C levels were measured by LC/MS. The concentration shown was normalized by cell number as detected by UV absorption assay.

Figure 46C:
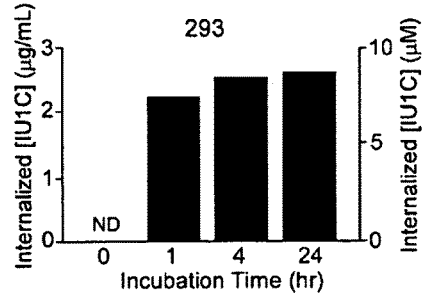

FIG. 46C shows a graph depicting the internalized IU1C concentration in 293 cells. After the indicated time-course treatment of 50 uM of IU1C, IU1C levels were measured by LC/MS. The concentration shown was normalized by cell number as detected by UV absorption assay.

Figure 46D:
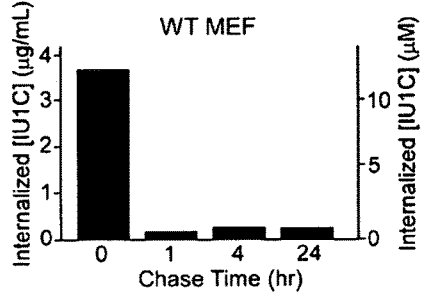

FIG. 46D shows a graph depicting rapid release of the internalized IU1C from wild-type MEF cells. The experiment was performed as in FIG. 42A.

Figure 46E:
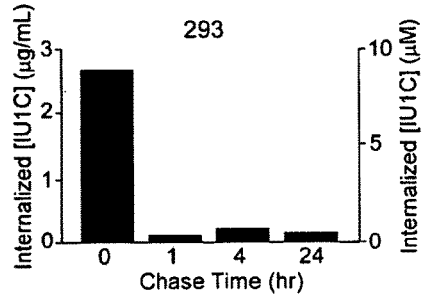

FIG. 46E shows a graph depicting rapid release of the internalized IU1C from 293 cells. The experiment was performed as in FIG. 42A.

Figure 47:
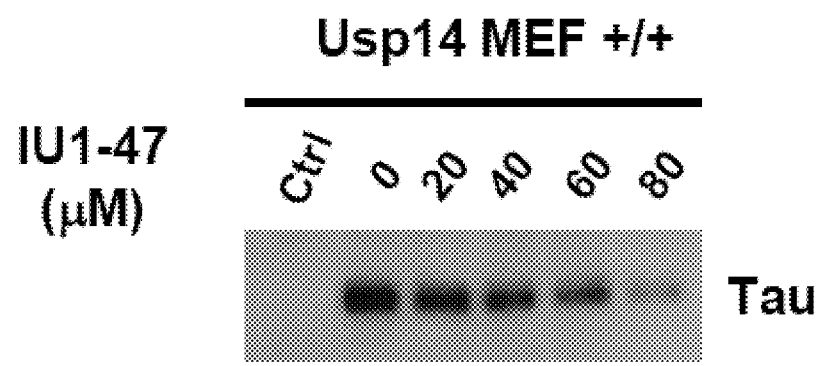

FIG. 47 shows an immunoblot that were performed using lysates of wild-type MEF cells that transiently expressed Tau and that were treated with 0, 20, 40, 60 or 80 µM of IU1-47, a more potent IU1 derivative, and stained with an antibody specific for Tau.

DETAILED DESCRIPTION

Proteinopathies are a class of diseases and disorders that result from the aggregation of abnormal or misfolded proteins. Often, and perhaps typically, such proteins are eliminated from cells through proteasome-mediated degradation. However, in the case of proteinopathies, the proteasome does not act efficiently enough to eliminate all of the harmful proteins and prevent the formation of the pathogenic aggregates.

As is demonstrated herein, under normal growth conditions, the proteasome is subject to tonic inhibition brought about by the trimming of substrate-bound ubiquitin chains by Usp14. Ubiquitin chain trimming inhibits the proteasome because it removes from proteasome substrates the signal (a ubiquitin chain) that allows recognition by the proteasome; the proteasome-bound substrate can therefore escape without being degraded. Consequently, an inhibitor of chain trimming by Usp14 promotes protein degradation by the proteasome. Thus, as a result of this inhibitory mechanism, the mammalian proteasome pathway does not ordinarily operate at full efficiency because the pathway is partially inhibited by Usp14.

The methods and compositions of the present invention enhance proteasome activity by inhibiting the deubiquitinase activity of Usp14. As demonstrated herein, this enhanced proteasome activity increases the ability of a cell to eliminate abnormal or misfolded proteins, including those associated with human disease. The methods and compositions of the present invention are therefore useful for the enhancement of proteasome function and the treatment of proteinopathies.

Definitions

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "substituted alkyl" means an aliphatic or cyclic hydrocarbon radical containing from 1 to 12 carbon atoms, substituted with 1, 2, 3, 4, or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl and silyloxy.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic (e.g. fused and spirocyclic) and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "N-heterocyclyl" as used herein is a subset of heterocyclyl, as defined herein, which have at least one nitrogen atom through which the N-heterocyclyl moiety is bound to the parent moiety. Representative examples include pyrrolidin-1-yl, piperidin-1-yl, piperazin-1-yl, hexahydropyrimidin-1-yl, morpholin-1-yl, 1,3-oxazinan-3-yl and 6-azaspiro[2.5]oct-6-yl. As with the heterocyclyl groups, the N-heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the N-heterocyclyl group through an alkylene moiety (e.g. methylene).

The term "aryl," as used herein means a phenyl group, naphthyl or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-fluorophenyl) pyridinyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to $—NH_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl and the sufonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a $—C{\equiv}N$ group.
The term "nitro" as used herein means a $—NO_2$ group.
The term "azido" as used herein means a $—N_3$ group.
The term "phosphinyl" as used herein includes $—PH_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to $—P(=O)OH_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes $H_3Si—$ and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

As used herein, the term "administering" means providing a pharmaceutical agent or composition to a subject, and includes, but is not limited to, administering by a medical professional and self-administering.

As used herein, the phrases "neurodegenerative disorder" and "neurodegenerative disease" refers to a wide range of diseases and/or disorders of the central and peripheral nervous system, such as neuropathologies, and includes but is not limited to, Parkinson's disease, Alzheimer's disease (AD), amyotrophic lateral sclerosis (ALS), denervation atrophy, otosclerosis, stroke, dementia, multiple sclerosis, Huntington's disease, encephalopathy associated with acquired immunodeficiency disease (AIDS), and other diseases associated with neuronal cell toxicity and cell death.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "pharmaceutically-acceptable salts" refers to the relatively non-toxic, inorganic and organic salts of compounds.

As used herein, the phrase "proteinopathy" refers to any disease associated with the accumulation and/or aggregation of abnormal or misfolded proteins. Though proteinopathies are frequently neurodegenerative diseases, proteinopathies also include diseases of other tissues, including the liver, muscle and heart, and include some cancers.

As used herein, the term "subject" means a human or non-human animal selected for treatment or therapy.

As used herein, the phrase "subject suspected of having" means a subject exhibiting one or more clinical indicators of a disease or condition. In certain embodiments, the disease or condition is cancer, a neurodegenerative disorder or pancreatitis.

As used herein, the phrase "subject in need thereof" means a subject identified as in need of a therapy or treatment of the invention.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some desired effect in at least a sub-population of cells. A therapeutically effective amount includes an amount of an agent that produces some desired local or systemic effect at a reasonable benefit/risk ratio applicable to any treatment. For example, certain agents used in the methods of the present invention may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of an agent, such that at least one symptom of the disease is decreased or prevented from worsening.

As used herein, "any of the aforementioned compounds" is any compound of formula I, II, III, IV, V, VI, VII, and VIII. Inhibitors of Usp14

One aspect of the invention relates to a compound represented by formula I:

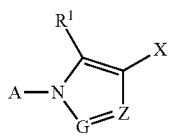

I or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl;

$R^1$ is hydrogen, alkyl, haloalkyl, fluoroalkyl, lower alkoxy, halo or trifluoromethyl;

G is —N= or —C($R^2$)=;

Z is =C($R^8$)—, =C($R^2$)— or =N—;

$R^2$ is hydrogen, alkyl, haloalkyl, fluoroalkyl, lower alkoxy, halo or trifluoromethyl; or, when G is —C($R^2$)= and Z is =C($R^2$)—, the two $R^2$ taken together are

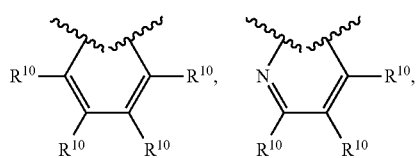

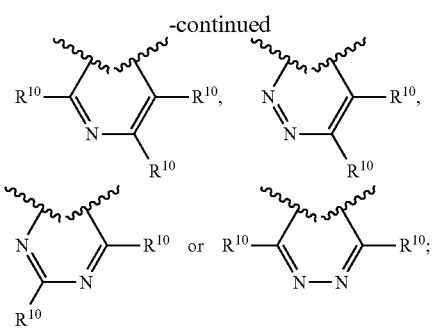

X is

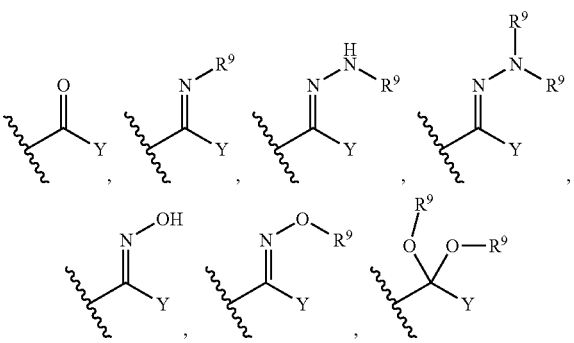

or heteroaryl;

Y is —CH$_2$NR$^3$R$^4$, —CH$_2$(N-heterocyclyl), —CH$_2$NH(CH$_2$)$_n$NH(alkyl), —CH$_2$NH(CH$_2$)$_n$N(alkyl)$_2$, —CH$_2$NH(CH$_2$)$_n$(N-heterocyclyl), —CH$_2$N(alkyl)(CH$_2$)$_n$NH(alkyl), —CH$_2$N(alkyl)(CH$_2$)$_n$N(alkyl)$_2$, —CH$_2$N(alkyl)(CH$_2$)$_n$(N-heterocyclyl), —CH$_2$NH(CH$_2$)$_n$O(alkyl), —CH$_2$N(alkyl)(CH$_2$)$_n$O(alkyl), —NR$^3$R$^4$, —NR$^5$NR$^6$R$^7$, —NR$^5$(N-heterocyclyl), or —N-heterocyclyl;

n is 1, 2, 3 or 4;

$R^3$ is hydrogen, alkyl, substituted alkyl, alkoxyalkyl, haloalkyl, fluoroalkyl, aryl, aralkyl, heteroaryl, or heteroaralkyl;

$R^4$ is hydrogen, alkyl, substituted alkyl, alkoxyalkyl, haloalkyl, fluoroalkyl, aryl, aralkyl, heteroaryl, or heteroaralkyl;

$R^5$ is hydrogen, alkyl, substituted alkyl, alkoxyalkyl, haloalkyl, fluoroalkyl, aryl, aralkyl, heteroaryl, or heteroaralkyl;

$R^6$ is hydrogen, alkyl, substituted alkyl, alkoxyalkyl, haloalkyl, fluoroalkyl, aryl, aralkyl, heteroaryl, or heteroaralkyl;

$R^7$ is hydrogen, alkyl, substituted alkyl, alkoxyalkyl, haloalkyl, fluoroalkyl, aryl, aralkyl, heteroaryl, or heteroaralkyl;

$R^8$ is hydrogen, alkyl, substituted alkyl, alkoxyalkyl, haloalkyl, fluoroalkyl, aryl, aralkyl, heteroaryl, or heteroaralkyl;

$R^9$ is alkyl; or two $R^9$ taken together with the nitrogen to which they are bound are an N-heterocyclyl group; and $R^{16}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

In certain embodiments, the present invention relates to any of the aforementioned compounds, provided that when A is 4-fluorophenyl, $R^1$ is methyl, G is —C($R^2$)=, $R^2$ is methyl, X is

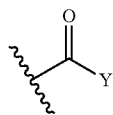

and Y is —CH$_2$(piperidin-1-yl), Z is not =C(H)—.

In certain embodiments, the present invention relates to any of the aforementioned compounds, provided that when A is 4-methylphenyl, R$^1$ is methyl, G is —C(R$^2$)=, R$^2$ is methyl, X is

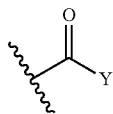

and Y is —CH$_2$(4-methylpiperidin-1-yl), Z is not =C(H)— (i.e., C100).

In certain embodiments, the present invention relates to any of the aforementioned compounds, provided that when A is 4-chlorophenyl, R$^1$ is methyl, G is —N=, X is

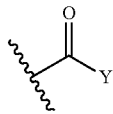

and Y is —NH$_2$, Z is not =N— (i.e., C121).

In certain embodiments, the present invention relates to any of the aforementioned compounds, wherein G is —N=.

In certain embodiments, the present invention relates to any of the aforementioned compounds, wherein G is —C(R$^2$)=.

In certain embodiments, the present invention relates to any of the aforementioned compounds, wherein the compound is represented by formula II:

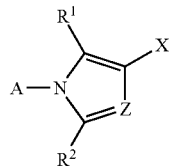

or is a pharmaceutically acceptable salt, solvate, hydrate, prodrug, chemically-protected form, enantiomer or stereoisomer thereof.

Another aspect of the invention relates to a compound represented by formula III:

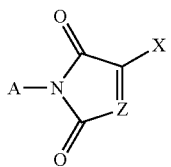

or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl;

Z is =C(R$^2$)— or =N—;

R$^2$ is hydrogen, alkyl, haloalkyl, fluoroalkyl, lower alkoxy, halo or trifluoromethyl; or, R$^2$ and X taken together are

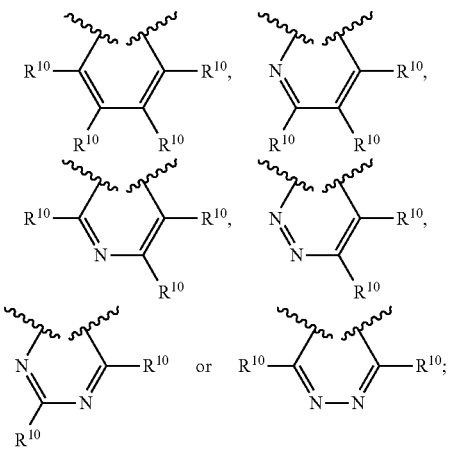

X is

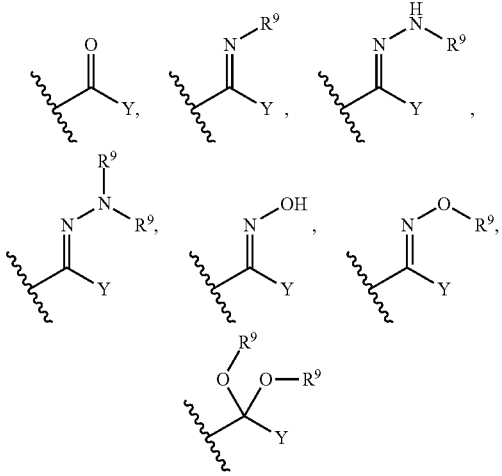

or heteroaryl;

Y is —CH$_2$NR$^3$R$^4$, —CH$_2$(N-heterocyclyl), —CH$_2$NH(CH$_2$)$_n$NH(alkyl), —CH$_2$NH(CH$_2$)$_n$N(alkyl)$_2$, —CH$_2$NH(CH$_2$)$_n$(N-heterocyclyl), —CH$_2$N(alkyl)(CH$_2$)$_n$NH(alkyl), —CH$_2$N(alkyl)(CH$_2$)$_n$N(alkyl)$_2$, —CH$_2$N(alkyl)(CH$_2$)$_n$(N-heterocyclyl), —CH$_2$NH(CH$_2$)$_n$O(alkyl), —CH$_2$N(alkyl)(CH$_2$)$_n$O(alkyl), —NR$^3$R$^4$, —NR$^5$NR$^6$R$^7$, —NR$^5$(N-heterocyclyl), or —N-heterocyclyl;

n is 1, 2, 3 or 4;

R$^3$ is hydrogen, alkyl, substituted alkyl, alkoxyalkyl, haloalkyl, fluoroalkyl, aryl, aralkyl, heteroaryl, or heteroaralkyl;

R$^4$ is hydrogen, alkyl, substituted alkyl, alkoxyalkyl, haloalkyl, fluoroalkyl, aryl, aralkyl, heteroaryl, or heteroaralkyl;

$R^5$ is hydrogen, alkyl, substituted alkyl, alkoxyalkyl, haloalkyl, fluoroalkyl, aryl, aralkyl, heteroaryl, or heteroaralkyl;

$R^6$ is hydrogen, alkyl, substituted alkyl, alkoxyalkyl, haloalkyl, fluoroalkyl, aryl, aralkyl, heteroaryl, or heteroaralkyl;

$R^7$ is hydrogen, alkyl, substituted alkyl, alkoxyalkyl, haloalkyl, fluoroalkyl, aryl, aralkyl, heteroaryl, or heteroaralkyl;

$R^9$ is alkyl; or two $R^9$ taken together with the nitrogen to which they are bound are an N-heterocyclyl group; and $R^{10}$ is hydrogen, alkyl, haloalkyl, fluoroalkyl, alkoxy, alkoxyalkyl, halo, trifluoromethyl, sulfoxymethyl, sulfonamido, amino, amido, N-heterocyclyl, aminoalkyl, amidoalkyl, or N-heterocyclylalkyl.

In certain embodiments, the present invention relates to any of the aforementioned compounds, provided that the compound is not C12.

In certain embodiments, the present invention relates to any of the aforementioned compounds, provided that the compound is not C31.

Another aspect of the invention relates to a compound represented by formula IV:

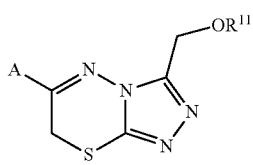

IV or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl; and $R^{11}$ is hydrogen, alkyl, alkylcarbonyl, aralkyl, haloalkyl, fluoroalkyl, alkoxyalkyl, trifluoromethyl, or silyl.

In certain embodiments, the present invention relates to any of the aforementioned compounds, provided that the compound is not C73.

Another aspect of the invention relates to a compound represented by formula V:

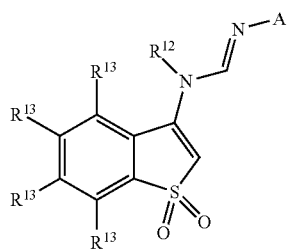

V or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl;

$R^{12}$ is hydrogen or alkyl; and $R^{13}$ is hydrogen, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, sulfoxymethyl, sulfonamido, amino, amido, azido, aminosulfonyl, aminosulfinyl, cyano, nitro, phosphinyl, phosphoryl, silyl, silyloxy, and any of said substituents bound through a methylene or ethylene moiety; or one or two instances of $R^{13}$, and the carbon to which it is bound, taken together are —N=.

In certain embodiments, the present invention relates to any of the aforementioned compounds, provided that the compound is not C106.

Another aspect of the invention relates to a compound represented by formula VI:

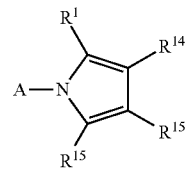

VI or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl;

$R^1$ is hydrogen, alkyl, haloalkyl, fluoroalkyl, lower alkoxy, halo or trifluoromethyl;

$R^{14}$ is hydrogen or X;

both $R^{15}$, taken together, are

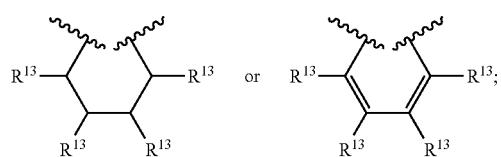

and $R^{13}$ is hydrogen, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, sulfoxymethyl, sulfonamido, amino, amido, azido, aminosulfonyl, aminosulfinyl, cyano, nitro, phosphinyl, phosphoryl, silyl, silyloxy, and any of said substituents bound through a methylene or ethylene moiety; or one or two instances of $R^{13}$, and the carbon to which it is bound, taken together are N.

In certain embodiments, the present invention relates to any of the aforementioned compounds, provided that the compound is not C118.

Another aspect of the invention relates to a compound represented by formula VII:

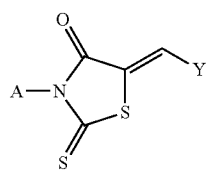

VII or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl; and Y is —CH$_2$NR$^3$R$^4$, —CH$_2$(N-heterocyclyl), —CH$_2$NH(CH$_2$)$_n$NH(alkyl), —CH$_2$NH(CH$_2$)$_n$N(alkyl)$_2$, —CH$_2$NH(CH$_2$)$_n$(N-heterocyclyl), —CH$_2$N(alkyl)(CH$_2$)$_n$NH(alkyl), —CH$_2$N(alkyl)(CH$_2$)$_n$N(alkyl)$_2$, —CH$_2$N(alkyl)(CH$_2$)$_n$(N-heterocyclyl), —CH$_2$NH(CH$_2$)$_n$O(alkyl), —CH$_2$N(alkyl)(CH$_2$)$_n$O(alkyl), —NR$^3$R$^4$, —NR$^5$NR$^6$R$^7$ or —NR$^5$(N-heterocyclyl).

In certain embodiments, the present invention relates to any of the aforementioned compounds, provided that the compound is not C133.

Another aspect of the invention relates to a compound represented by formula VIII:

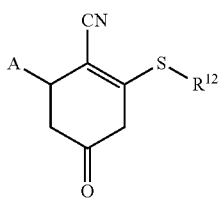

VIII or a pharmaceutically acceptable salt, solvate, hydrate, prodrug, chemically-protected form, enantiomer or stereoisomer thereof; wherein, independently for each occurrence, A is aryl, heteroaryl, carbocyclyl, heterocyclyl, or biaryl; and R$^{12}$ is hydrogen or alkyl.

In certain embodiments, the present invention relates to any of the aforementioned compounds, provided that the compound is not C139.

In certain embodiments, the present invention relates to any of the aforementioned compounds, wherein A is aryl or heteroaryl.

In certain embodiments, the present invention relates to any of the aforementioned compounds, wherein A is phenyl, pyridin-2-yl, pyridin-3-yl or pyrimidin-2-yl, optionally substituted with 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, sulfoxymethyl, sulfonamido, amino, amido, azido, aminosulfonyl, aminosulfinyl, cyano, nitro, phosphinyl, phosphoryl, silyl, silyloxy, and any of said substituents bound to the phenyl, pyridin-2yl, pyridin-3-yl or pyrimidin-2-yl through a methylene or ethylene moiety.

In certain embodiments, the present invention relates to any of the aforementioned compounds, wherein A is phenyl, optionally substituted with 1, 2, 3, 4 or 5 substituents independently selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

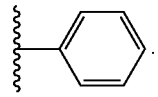

In certain embodiments, the present invention relates to any of the aforementioned compounds, wherein A is phenyl substituted in the two position (ortho substituted) with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

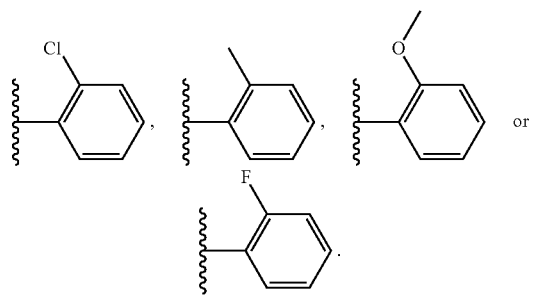

In certain embodiments, the present invention relates to any of the aforementioned compounds, wherein A is phenyl substituted in the three position (meta substituted) with a substituent selected from the group consisting of alkyl, halo, haloalkyl, fluoroalkyl, hydroxy, alkoxy, haloalkoxy, fluoroalkyloxy, amino, azido cyano, and nitro.

In certain embodiments, the present invention relates to any of the aforementioned compounds, wherein A is

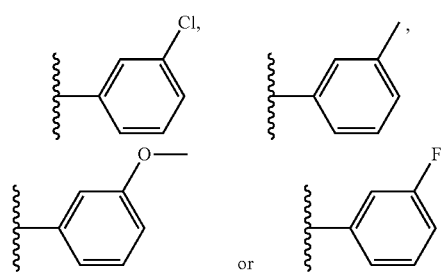

In certain embodiments, the present invention relates to any of the aforementioned compounds, wherein A is phenyl substituted in the four position (para substituted) with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

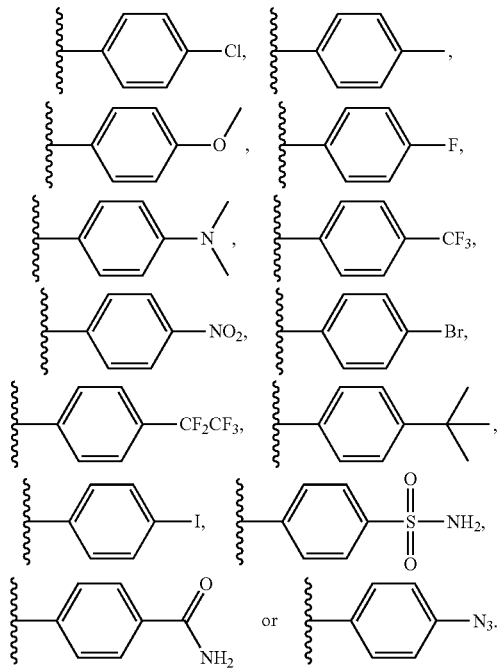

In certain embodiments, the present invention relates to any of the aforementioned compounds, wherein A is phenyl substituted in the two and four positions with substituents independently selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

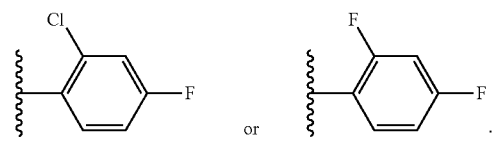

In certain embodiments, the present invention relates to any of the aforementioned compounds, wherein A is pyridin-2-yl, optionally substituted in the four position with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

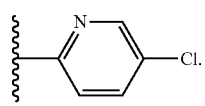

In certain embodiments, the present invention relates to any of the aforementioned compounds, wherein A is pyrimidin-2-yl, optionally substituted in the four position with a substituent selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

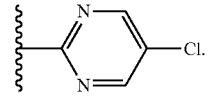 [SMILES: *c1ncc(Cl)cn1]

In certain embodiments, the present invention relates to any of the aforementioned compounds, wherein A is biaryl.

In certain embodiments, the present invention relates to any of the aforementioned compounds, wherein A is 4-(phenyl)phen-1-yl or 4-(2-pyridinyl)phen-1-yl, optionally substituted with 1, 2, 3, 4 or 5 substituents independently selected from the group consisting of alkyl, halo, haloalkyl, fluoroalkyl, hydroxy, alkoxy, haloalkoxy, fluoroalkyloxy, amino, azido, cyano, and nitro.

In certain embodiments, the present invention relates to any of the aforementioned compounds, wherein A is

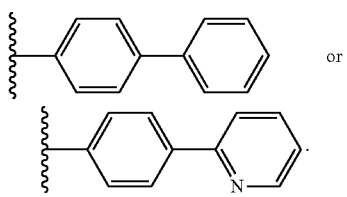

In certain embodiments, the present invention relates to any of the aforementioned compounds, wherein $R^1$ is hydrogen.

In certain embodiments, the present invention relates to any of the aforementioned compounds, wherein $R^1$ is alkyl.

In certain embodiments, the present invention relates to any of the aforementioned compounds, wherein $R^1$ is haloalkyl.

In certain embodiments, the present invention relates to any of the aforementioned compounds, wherein $R^1$ is fluoroalkyl.

In certain embodiments, the present invention relates to any of the aforementioned compounds, wherein $R^1$ is methyl.

In certain embodiments, the present invention relates to any of the aforementioned compounds, wherein $R^1$ is halomethyl.

In certain embodiments, the present invention relates to any of the aforementioned compounds, wherein $R^1$ is fluoromethyl.

In certain embodiments, the present invention relates to any of the aforementioned compounds, wherein $R^1$ is ethyl.

In certain embodiments, the present invention relates to any of the aforementioned compounds, wherein $R^1$ is haloethyl.

In certain embodiments, the present invention relates to any of the aforementioned compounds, wherein $R^1$ is fluoroethyl.

In certain embodiments, the present invention relates to any of the aforementioned compounds, wherein $R^2$ is hydrogen.

In certain embodiments, the present invention relates to any of the aforementioned compounds, wherein $R^2$ is alkyl.

In certain embodiments, the present invention relates to any of the aforementioned compounds, wherein $R^2$ is methyl.

In certain embodiments, the present invention relates to any of the aforementioned compounds, wherein $R^2$ is ethyl.

In certain embodiments, the present invention relates to any of the aforementioned compounds, wherein $R^1$ is hydrogen; and $R^2$ is hydrogen.

In certain embodiments, the present invention relates to any of the aforementioned compounds, wherein $R^1$ is alkyl; and $R^2$ is alkyl.

In certain embodiments, the present invention relates to any of the aforementioned compounds, wherein $R^1$ is methyl; and $R^2$ is methyl.

In certain embodiments, the present invention relates to any of the aforementioned compounds, wherein $R^1$ is ethyl; and $R^2$ is ethyl.

In certain embodiments, the present invention relates to any of the aforementioned compounds, wherein Z is $=C(R^8)—$; and $R^8$ is hydrogen.

In certain embodiments, the present invention relates to any of the aforementioned compounds, wherein Z is $=C(R^8)—$; and $R^8$ is alkyl.

In certain embodiments, the present invention relates to any of the aforementioned compounds, wherein Z is $=N—$.

In certain embodiments, the present invention relates to any of the aforementioned compounds, wherein X is

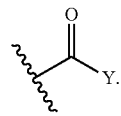

In certain embodiments, the present invention relates to any of the aforementioned compounds, wherein X is

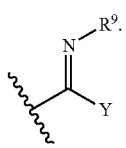

In certain embodiments, the present invention relates to any of the aforementioned compounds, wherein X is

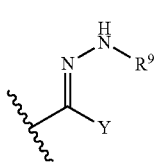 or 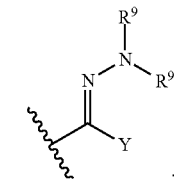.

In certain embodiments, the present invention relates to any of the aforementioned compounds, wherein X is heteroaryl.

In certain embodiments, the present invention relates to any of the aforementioned compounds, wherein X is pyrrolo[1,2-a]pyrazin-3-yl.

In certain embodiments, the present invention relates to any of the aforementioned compounds, wherein $R^9$ is alkyl.

In certain embodiments, the present invention relates to any of the aforementioned compounds, wherein $R^9$ is methyl.

In certain embodiments, the present invention relates to any of the aforementioned compounds, wherein Y is $—CH_2NR^3R^4$.

In certain embodiments, the present invention relates to any of the aforementioned compounds, wherein Y is $—CH_2NR^3R^4$; and $R^3$ is hydrogen.

In certain embodiments, the present invention relates to any of the aforementioned compounds, wherein Y is $—CH_2NR^3R^4$; and $R^3$ is alkyl. In certain embodiments, the present invention relates to any of the aforementioned compounds, wherein Y is $—CH_2NR^3R^4$; and $R^4$ is hydrogen.

In certain embodiments, the present invention relates to any of the aforementioned compounds, wherein Y is $—CH_2NR^3R^4$; and $R^4$ is alkyl.

In certain embodiments, the present invention relates to any of the aforementioned compounds, wherein Y is $—CH_2NR^3R^4$; and $R^4$ is alkoxyalkyl.

In certain embodiments, the present invention relates to any of the aforementioned compounds, wherein Y is $—CH_2NR^3R^4$; $R^3$ is hydrogen; and $R^4$ is alkyl.

In certain embodiments, the present invention relates to any of the aforementioned compounds, wherein Y is $—CH_2NR^3R^4$; $R^3$ is alkyl; and $R^4$ is alkyl.

In certain embodiments, the present invention relates to any of the aforementioned compounds, wherein Y is $—CH_2NR^3R^4$; $R^3$ is hydrogen; and $R^4$ is alkoxyalkyl.

In certain embodiments, the present invention relates to any of the aforementioned compounds, wherein Y is $—CH_2NR^3R^4$; $R^3$ is alkyl; and $R^4$ is alkoxyalkyl.

In certain embodiments, the present invention relates to any of the aforementioned compounds, wherein Y is

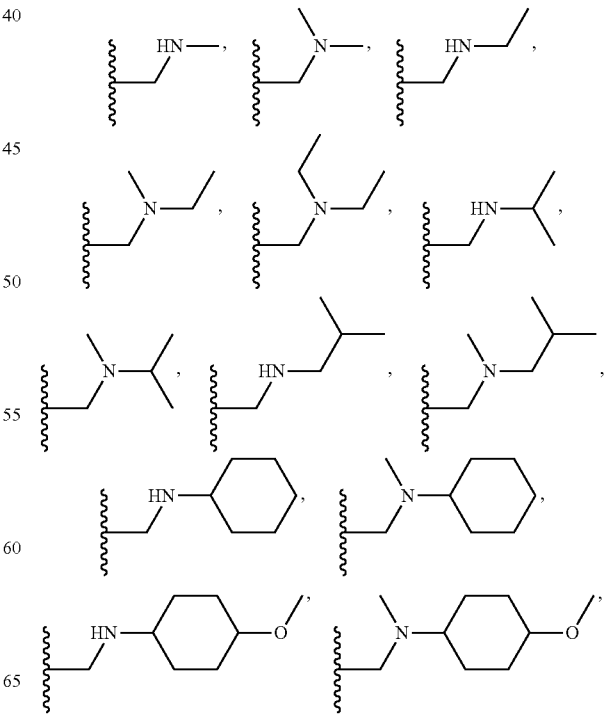

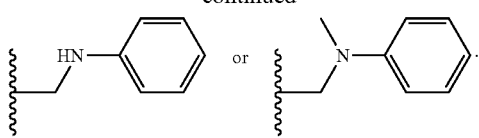

In certain embodiments, the present invention relates to any of the aforementioned compounds, wherein Y is —CH$_2$(N-heterocyclyl), which is optionally substituted with one, two, three, four or five substituents independently selected from the group consisting of alkyl, haloalkyl, fluoroalkyl, halo, hydroxyl, alkoxy, haloalkoxy, fluoroalkoxy, amino and nitro.

In certain embodiments, the present invention relates to any of the aforementioned compounds, wherein Y is —CH$_2$(piperidin-1-yl), —CH$_2$(piperazin-1-yl), —CH$_2$(hexahydropyrimidin-1-yl), —CH$_2$(morpholin-1-yl) or —CH$_2$(1,3-oxazinan-3-yl), which is optionally substituted with one, two, three, four or five substituents independently selected from the group consisting of alkyl, haloalkyl, fluoroalkyl, halo, hydroxyl, alkoxy, haloalkoxy, fluoroalkoxy, amino and nitro.

In certain embodiments, the present invention relates to any of the aforementioned compounds, wherein Y is —CH$_2$(piperidin-1-yl) or —CH$_2$(piperazin-1-yl), which is optionally substituted with one, two, three, four or five substituents independently selected from the group consisting of alkyl, haloalkyl, fluoroalkyl, halo, hydroxyl, alkoxy, haloalkoxy, fluoroalkoxy, amino and nitro.

In certain embodiments, the present invention relates to any of the aforementioned compounds, wherein Y is

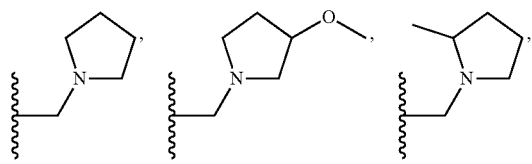

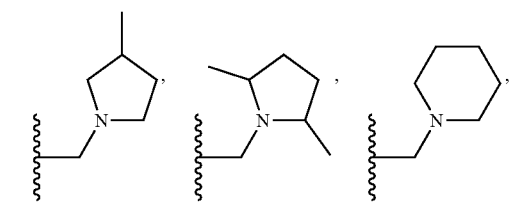

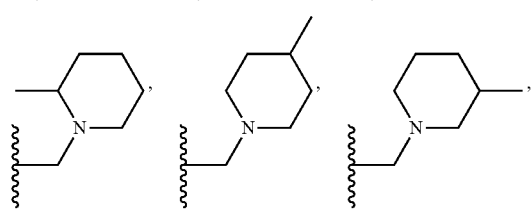

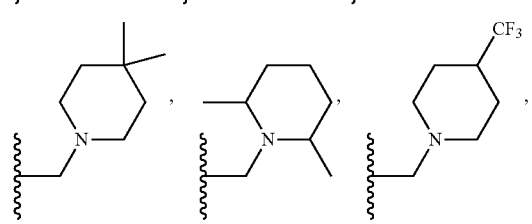

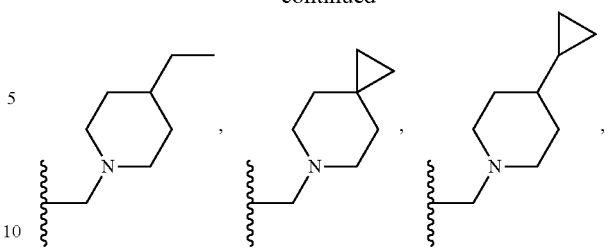

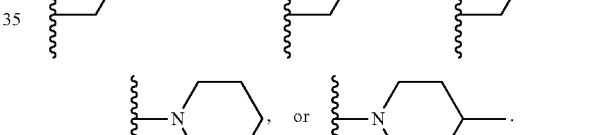

In certain embodiments, the present invention relates to any of the aforementioned compounds, wherein Y is —CH$_2$NH(CH$_2$)$_n$NH(alkyl), —CH$_2$NH(CH$_2$)$_n$N(alkyl)$_2$, —CH$_2$NH(CH$_2$)$_n$N(alkylene)), —CH$_2$N(alkyl)(CH$_2$)$_n$NH(alkyl), —CH$_2$N(alkyl)(CH$_2$)$_n$N(alkyl)$_2$ or —CH$_2$N(alkyl)(CH$_2$)$_n$N(alkylene)).

In certain embodiments, the present invention relates to any of the aforementioned compounds, wherein Y is —CH$_2$NH(CH$_2$)$_n$O(alkyl) or —CH$_2$N(alkyl)(CH$_2$)$_n$O(alkyl).

In certain embodiments, the present invention relates to any of the aforementioned compounds, wherein n is 1.

In certain embodiments, the present invention relates to any of the aforementioned compounds, wherein n is 2.

In certain embodiments, the present invention relates to any of the aforementioned compounds, wherein n is 3.

In certain embodiments, the present invention relates to any of the aforementioned compounds, wherein n is 4.

In certain embodiments, the present invention relates to any of the aforementioned compounds, wherein Y is

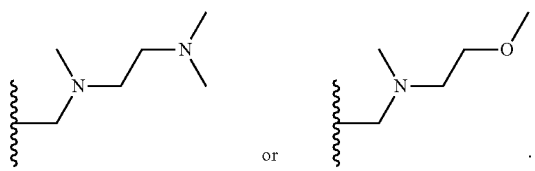

or

In certain embodiments, the present invention relates to any of the aforementioned compounds, wherein Y is —NR³R⁴.

In certain embodiments, the present invention relates to any of the aforementioned compounds, wherein Y is —NR³R⁴; and R³ is hydrogen.

In certain embodiments, the present invention relates to any of the aforementioned compounds, wherein Y is —NR³R⁴; and R³ is alkyl.

In certain embodiments, the present invention relates to any of the aforementioned compounds, wherein Y is —NR³R⁴; and R⁴ is hydrogen.

In certain embodiments, the present invention relates to any of the aforementioned compounds, wherein Y is —NR³R⁴; and R⁴ is alkyl.

In certain embodiments, the present invention relates to any of the aforementioned compounds, wherein Y is —NR³R⁴; R³ is hydrogen; and R⁴ is alkyl.

In certain embodiments, the present invention relates to any of the aforementioned compounds, wherein Y is —NR³R⁴; R³ is hydrogen; and R⁴ is hydrogen. In certain embodiments, the present invention relates to any of the aforementioned compounds, wherein Y is —NR³R⁴; R³ is alkyl; and R⁴ is alkyl.

In certain embodiments, the present invention relates to any of the aforementioned compounds, wherein Y is —NR⁵NR⁶R⁷ or —NR⁵(N-heterocyclyl).

In certain embodiments, the present invention relates to any of the aforementioned compounds, wherein Y is —NR⁵NR⁶R⁷; and R⁵ is hydrogen.

In certain embodiments, the present invention relates to any of the aforementioned compounds, wherein Y is —NR⁵NR⁶R⁷; and R⁵ is alkyl.

In certain embodiments, the present invention relates to any of the aforementioned compounds, wherein Y is —NR⁵NR⁶R⁷; and R⁵, R⁶ and R⁷ are, independently, hydrogen or alkyl.

In certain embodiments, the present invention relates to any of the aforementioned compounds, wherein Y is —NR⁵(N-heterocyclyl); and R⁵ is hydrogen.

In certain embodiments, the present invention relates to any of the aforementioned compounds, wherein Y is —NR⁵(N-heterocyclyl); and R⁵ is alkyl.

In certain embodiments, the present invention relates to any of the aforementioned compounds, wherein Y is

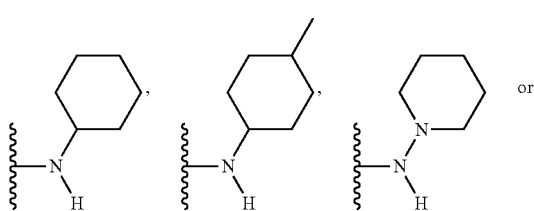

or

-continued

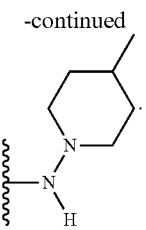

In certain embodiments, the present invention relates to any of the aforementioned compounds, wherein Z is =C(R²)—; and the two R² taken together are

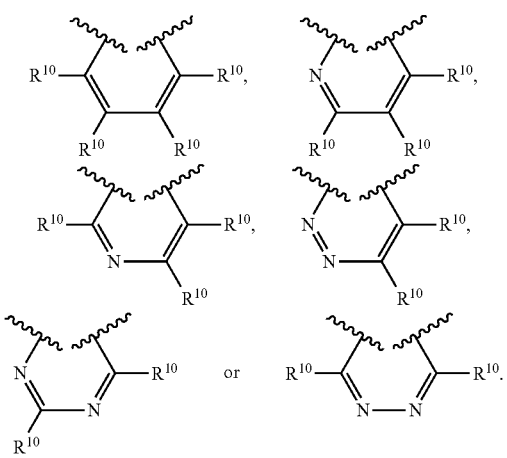

In certain embodiments, the present invention relates to any of the aforementioned compounds, wherein Z is =C(R²)—; and the two R² taken together are

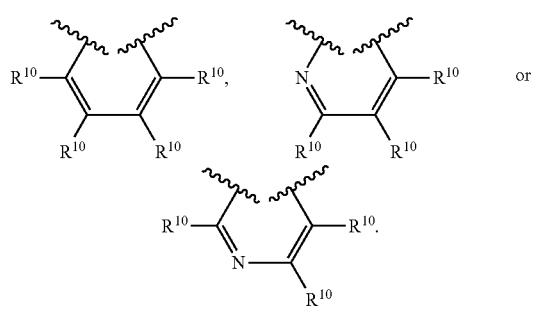

In certain embodiments, the present invention relates to any of the aforementioned compounds, wherein Z is =C(R²)—; and the two R² taken together are

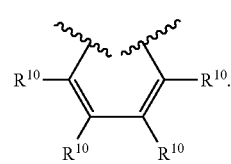

In certain embodiments, the present invention relates to any of the aforementioned compounds, wherein Z is =C(R²)—; and the two R² taken together are

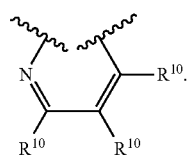

In certain embodiments, the present invention relates to any of the aforementioned compounds, wherein Z is =C(R$^2$)—; and the two R$^2$ taken together are

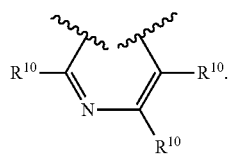

In certain embodiments, the present invention relates to any of the aforementioned compounds, wherein R$^{10}$ is hydrogen, alkyl, haloalkyl, fluoroalkyl, alkoxy, alkoxyalkyl, halo or trifluoromethyl.

In certain embodiments, the present invention relates to any of the aforementioned compounds, wherein R$^{10}$ is hydrogen, amino, amido, N-heterocyclyl, aminoalkyl, amidoalkyl, or N-heterocyclylalkyl.

In certain embodiments, the present invention relates to any of the aforementioned compounds, wherein R$^{10}$ is hydrogen, halo or N-heterocyclyl.

In certain embodiments, the present invention relates to any of the aforementioned compounds, wherein R$^{10}$ is hydrogen, chloro or piperidin-1-yl.

In certain embodiments, the present invention relates to any of the aforementioned compounds, wherein R$^{10}$ is hydrogen or N-heterocyclylalkyl.

In certain embodiments, the present invention relates to any of the aforementioned compounds, wherein R$^{10}$ is hydrogen or piperidin-1-ylmethyl.

In certain embodiments, the present invention relates to any of the aforementioned compounds, wherein R$^{10}$ is hydrogen or alkyl.

In certain embodiments, the present invention relates to any of the aforementioned compounds, wherein R$^{10}$ is hydrogen.

In certain embodiments, the present invention relates to any of the aforementioned compounds, wherein R$^{11}$ is hydrogen or alkyl.

In certain embodiments, the present invention relates to any of the aforementioned compounds, wherein R$^{11}$ is hydrogen.

In certain embodiments, the present invention relates to any of the aforementioned compounds, wherein R$^{11}$ is methyl.

In certain embodiments, the present invention relates to any of the aforementioned compounds, wherein R$^{12}$ is hydrogen.

In certain embodiments, the present invention relates to any of the aforementioned compounds, wherein R$^{12}$ is methyl. In certain embodiments, the present invention relates to any of the aforementioned compounds, wherein R$^{13}$ is hydrogen.

In certain embodiments, the present invention relates to any of the aforementioned compounds, wherein exactly one R$^{13}$, and the carbon to which it is bound, is —N=.

In certain embodiments, the present invention relates to any of the aforementioned compounds, wherein R$^{14}$ is hydrogen.

In certain embodiments, the present invention relates to any of the aforementioned compounds, wherein R$^{14}$ is X. In certain embodiments, the present invention relates to any of the aforementioned compounds, wherein Z is =C(R$^2$)—; the two R$^2$ taken together are

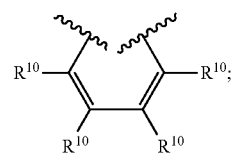

and R$^{10}$ is hydrogen, halo or N-heterocyclyl.

In certain embodiments, the present invention relates to any of the aforementioned compounds, wherein Z is =C(R$^2$)—; the two R$^2$ taken together are

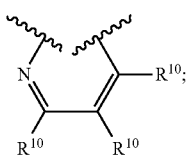

and R$^{10}$ is hydrogen or N-heterocyclylalkyl.

Another aspect of the invention relates to a compound, or a pharmaceutically acceptable salt, solvate, hydrate, prodrug, chemically-protected form, enantiomer or stereoisomer thereof, selected from the group consisting of

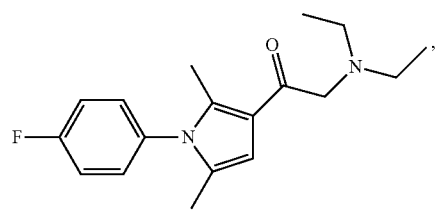

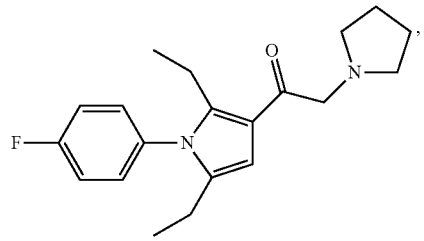

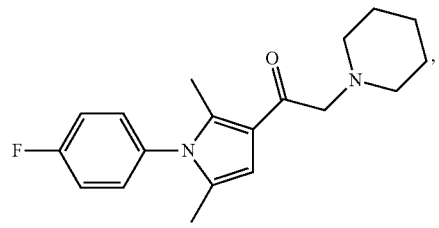

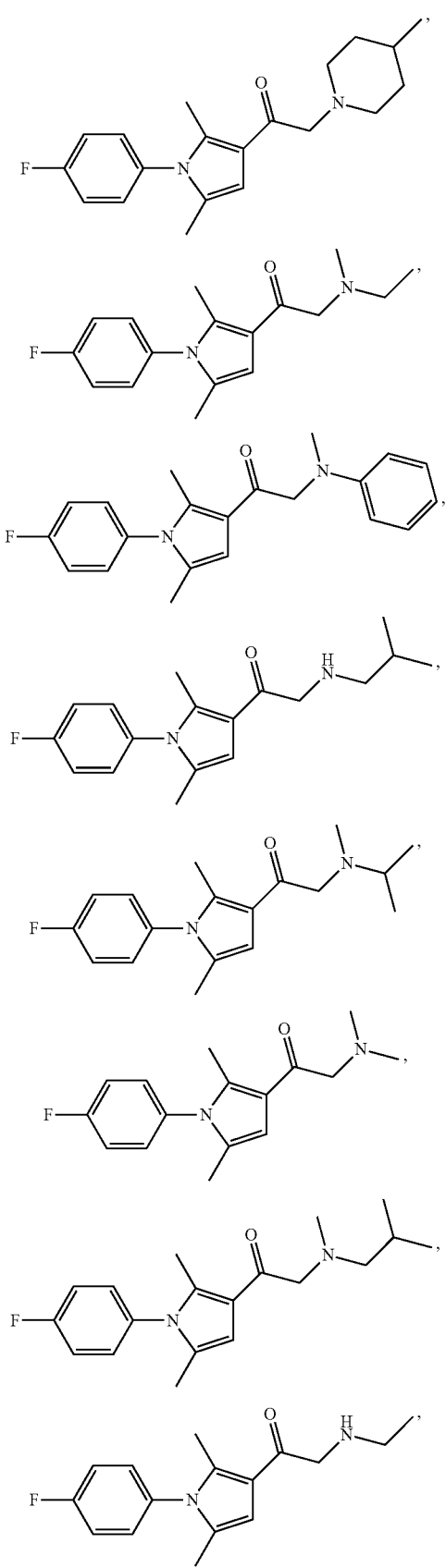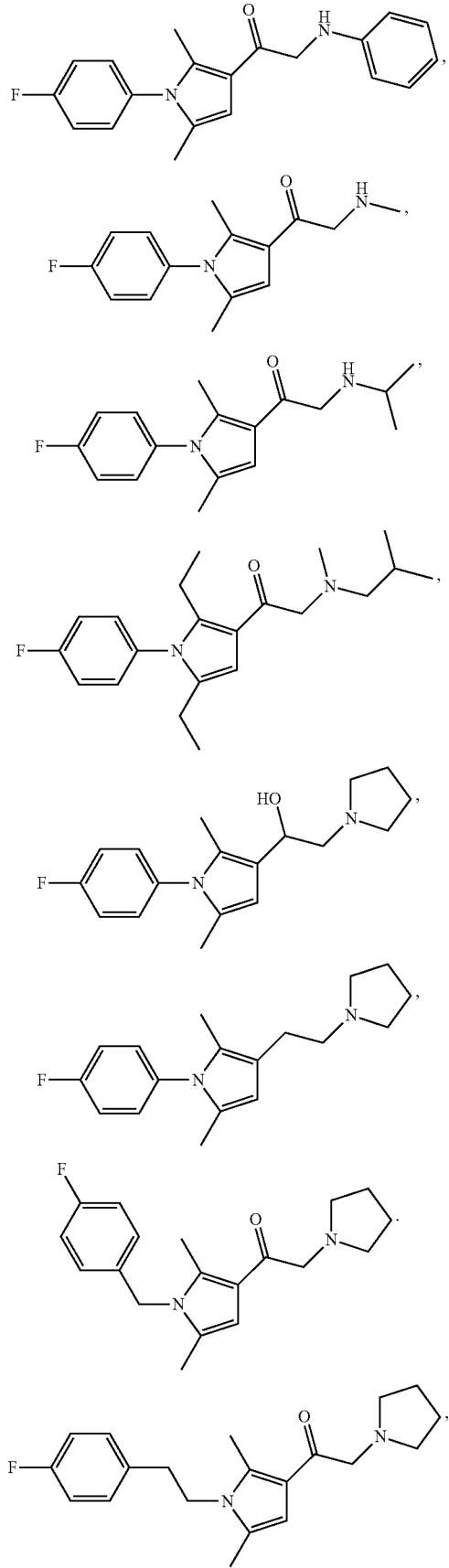

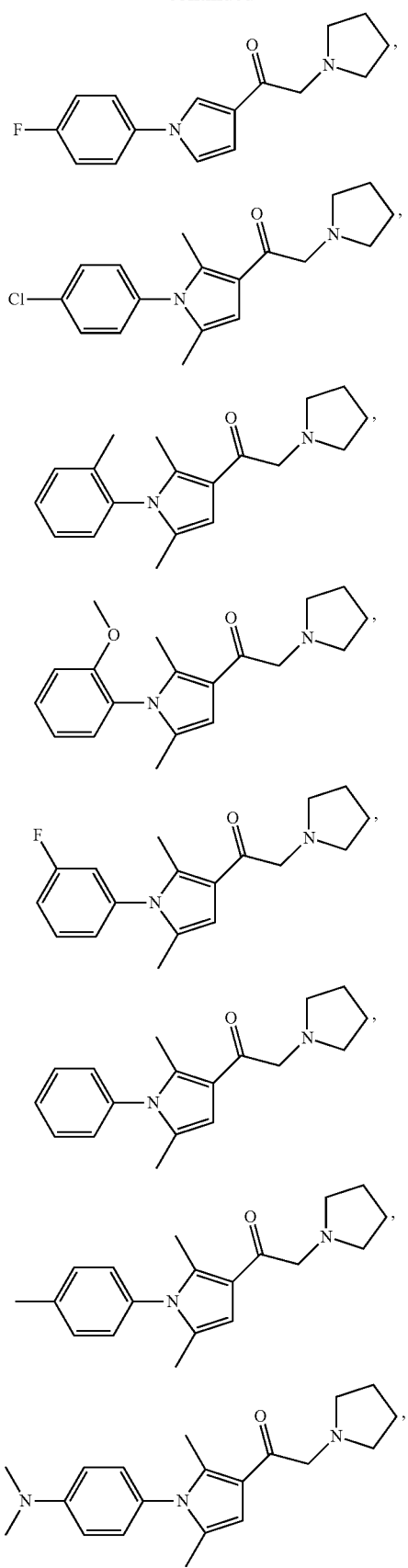
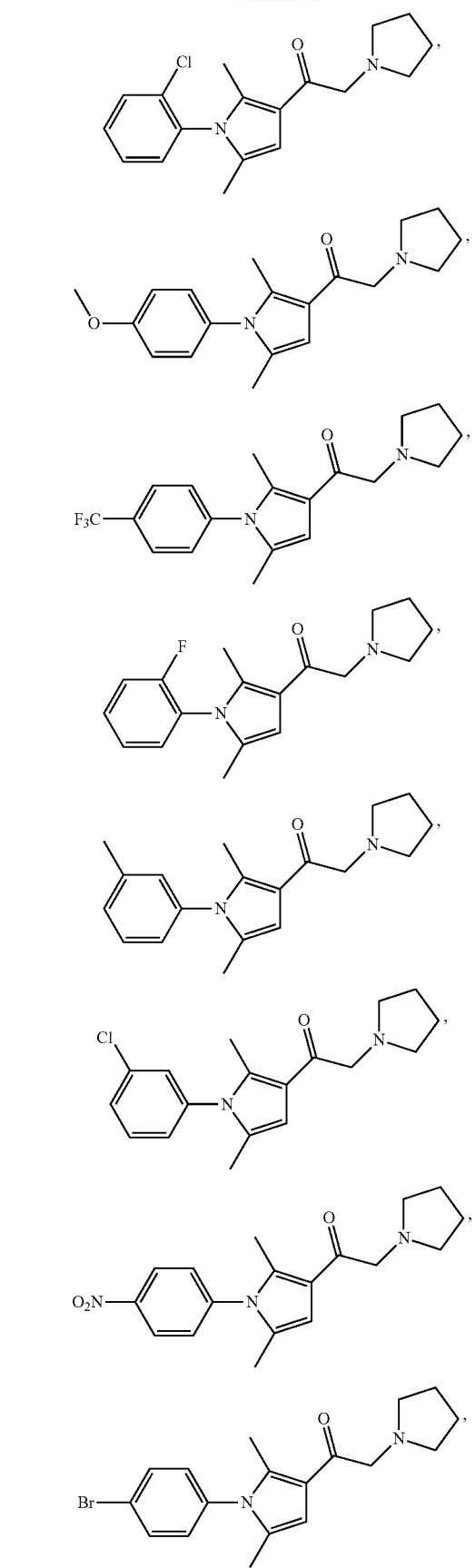

-continued

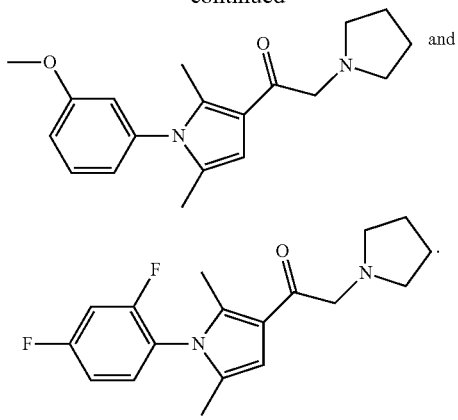

Another aspect of the invention relates to a compound, or a pharmaceutically acceptable salt, solvate, hydrate, prodrug, chemically-protected form, enantiomer or stereoisomer thereof, selected from the group consisting of

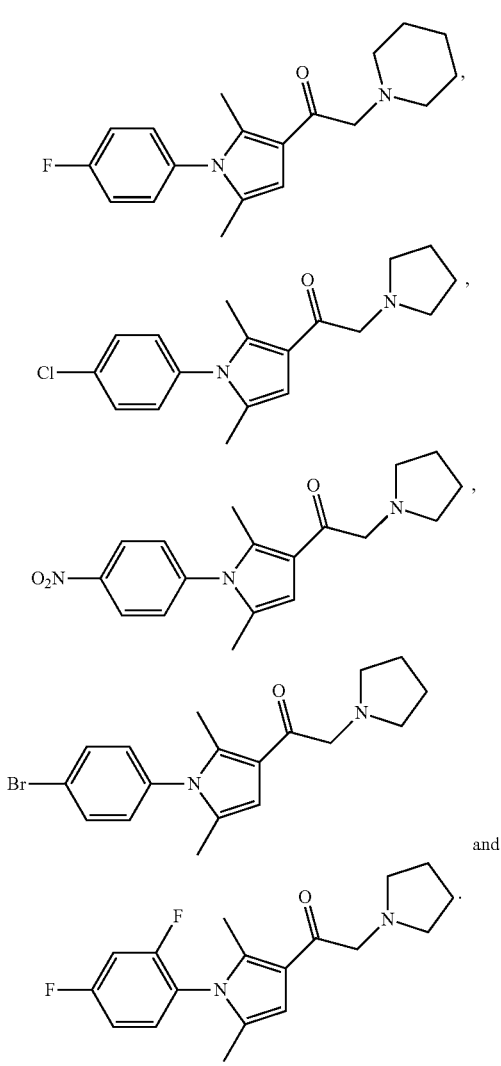

Another aspect of the invention relates to a compound, or a pharmaceutically acceptable salt, solvate, hydrate, prodrug, chemically-protected form, enantiomer or stereoisomer thereof, of the following formula

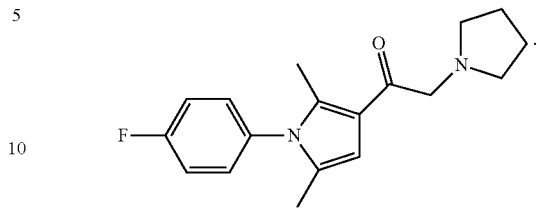

Another aspect of the invention relates to a compound, or a pharmaceutically acceptable salt, solvate, hydrate, prodrug, chemically-protected form, enantiomer or stereoisomer thereof, of the following formula

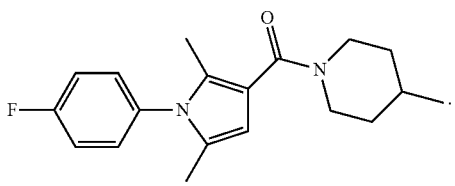 [SMILES: Cc1cc(C(=O)N2CCC(C)CC2)c(C)n1-c1ccc(F)cc1]

Another aspect of the invention relates to a compound, or a pharmaceutically acceptable salt, solvate, hydrate, prodrug, chemically-protected form, enantiomer or stereoisomer thereof, selected from the group consisting of

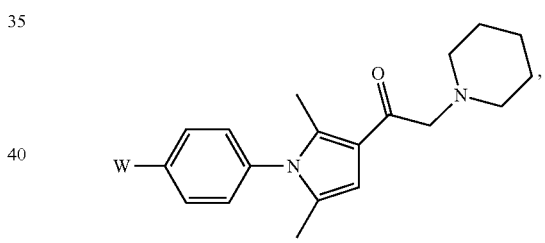

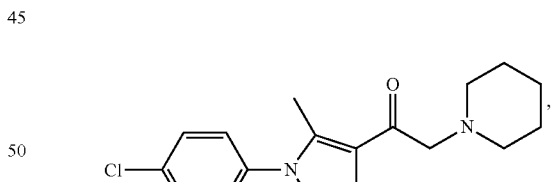

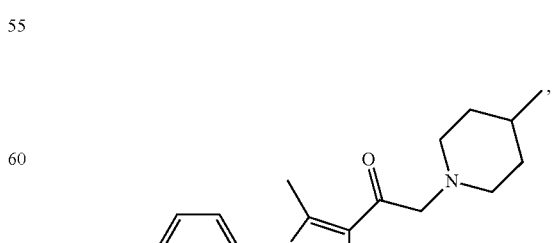

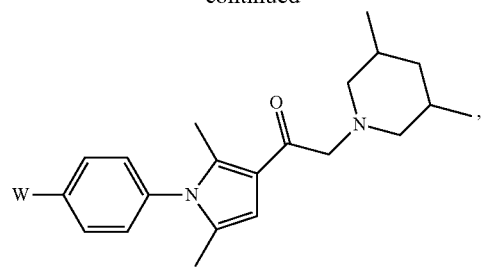
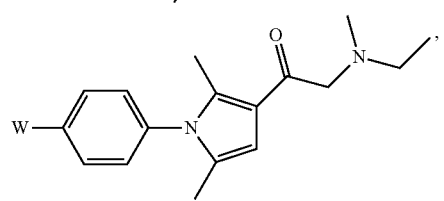
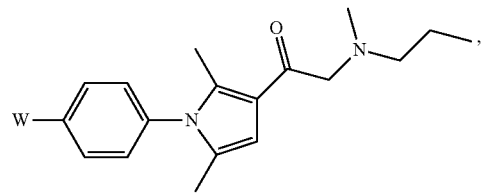
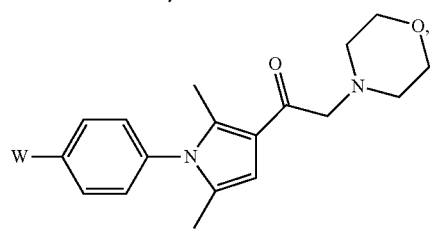
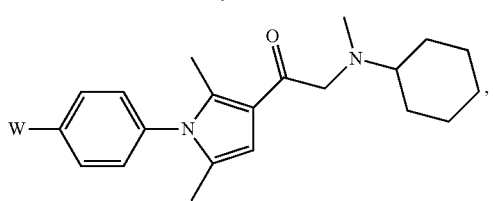
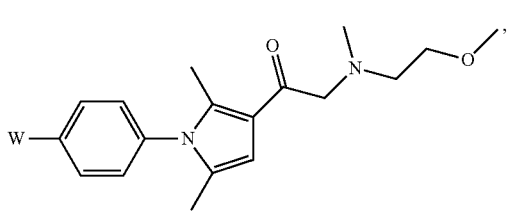
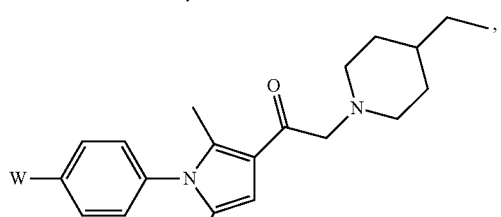
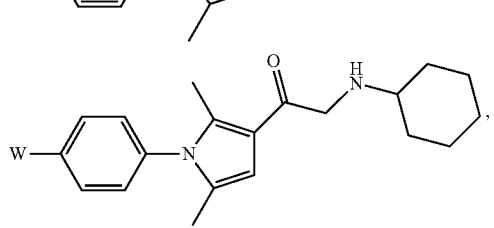
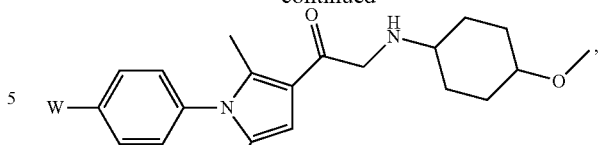
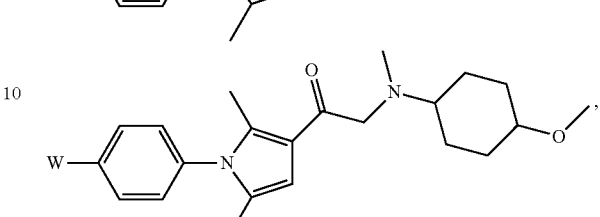
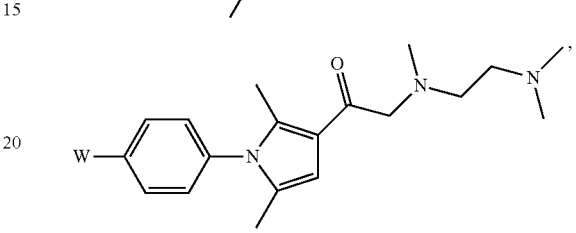
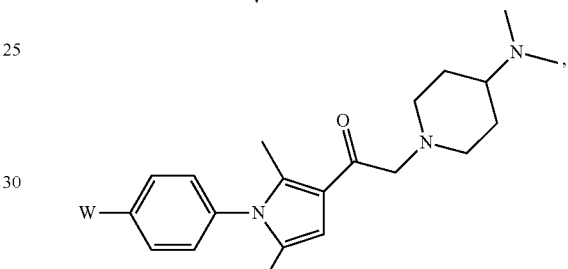
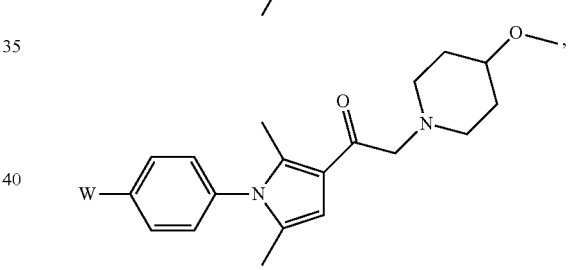
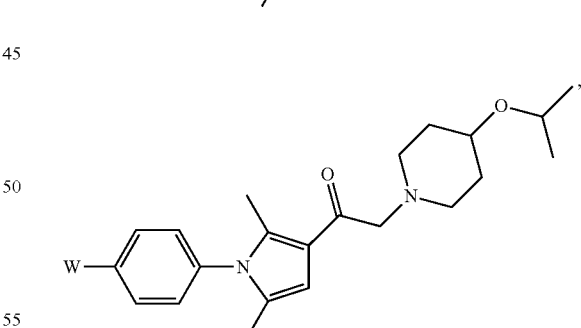
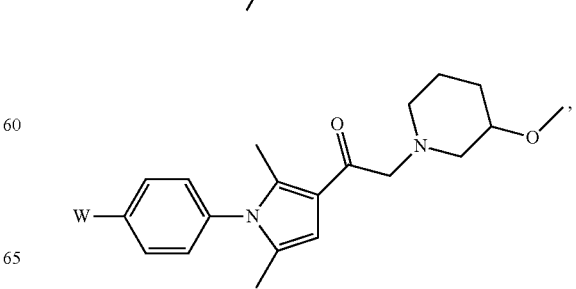

-continued

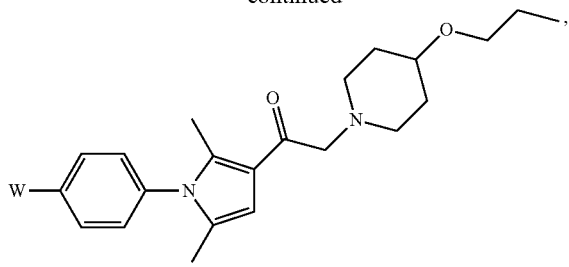

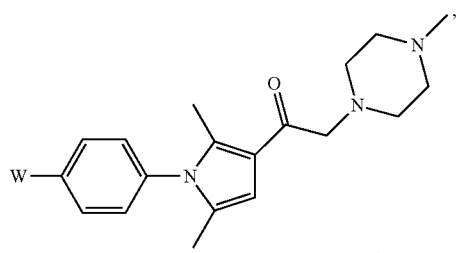

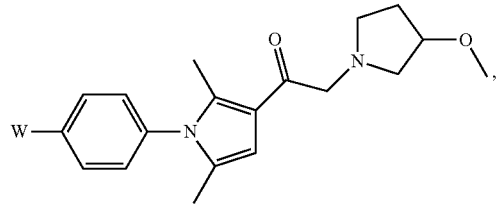

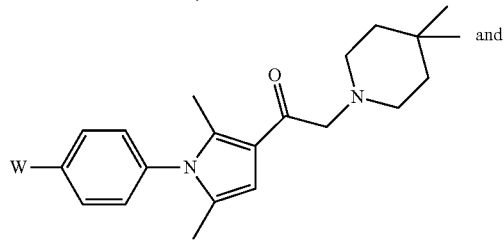 and

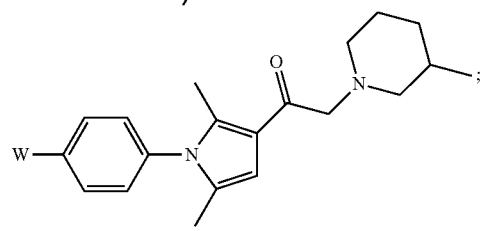

wherein W is methyl, fluoro, chloro, nitro, methoxy, ethoxy, —SO$_2$NH$_2$ or —C(=O)NH$_2$.

Another aspect of the invention relates to a compound, or a pharmaceutically acceptable salt, solvate, hydrate, prodrug, chemically-protected form, enantiomer or stereoisomer thereof, selected from the group consisting of

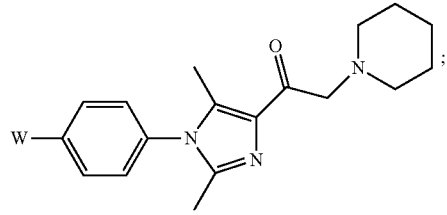

wherein W is alkyl, fluoro, chloro, nitro, methoxy, ethoxy, —SO$_2$NH$_2$ or —C(=O)NH$_2$.

In certain embodiments, the present invention relates to any of the aforementioned compounds, wherein W is methyl.

In certain embodiments, the present invention relates to any of the aforementioned compounds, wherein W is fluoro.

In certain embodiments, the present invention relates to any of the aforementioned compounds, wherein W is chloro.

In certain embodiments, the present invention relates to any of the aforementioned compounds, wherein W is nitro.

In certain embodiments, the present invention relates to any of the aforementioned compounds, wherein W is methoxy.

In certain embodiments, the present invention relates to any of the aforementioned compounds, wherein W is ethoxy.

In certain embodiments, the present invention relates to any of the aforementioned compounds, wherein W is —SO$_2$NH$_2$.

In certain embodiments, the present invention relates to any of the aforementioned compounds, wherein W is —C(=O)NH$_2$.

Another aspect of the invention relates to a compound, or a pharmaceutically acceptable salt, solvate, hydrate, prodrug, chemically-protected form, enantiomer or stereoisomer thereof, selected from the group consisting of

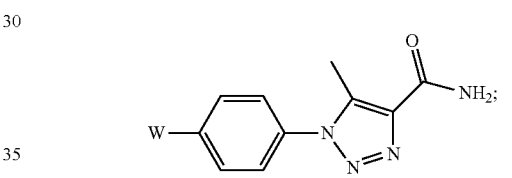

wherein W is alkyl, fluoro, chloro, nitro, methoxy, ethoxy, —SO$_2$NH$_2$ or —C(=O)NH$_2$.

In certain embodiments, the present invention relates to any of the aforementioned compounds, wherein W is chloro.

Another aspect of the invention relates to a compound, or a pharmaceutically acceptable salt, solvate, hydrate, prodrug, chemically-protected form, enantiomer or stereoisomer thereof, selected from the group consisting of

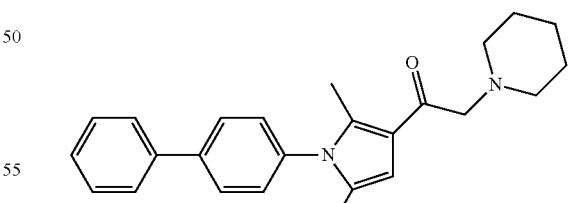

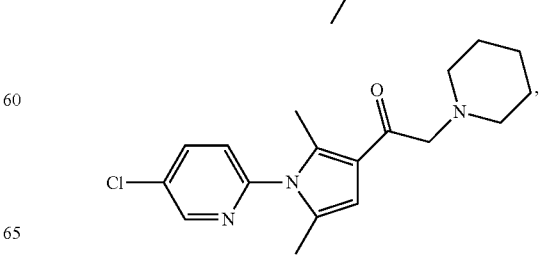

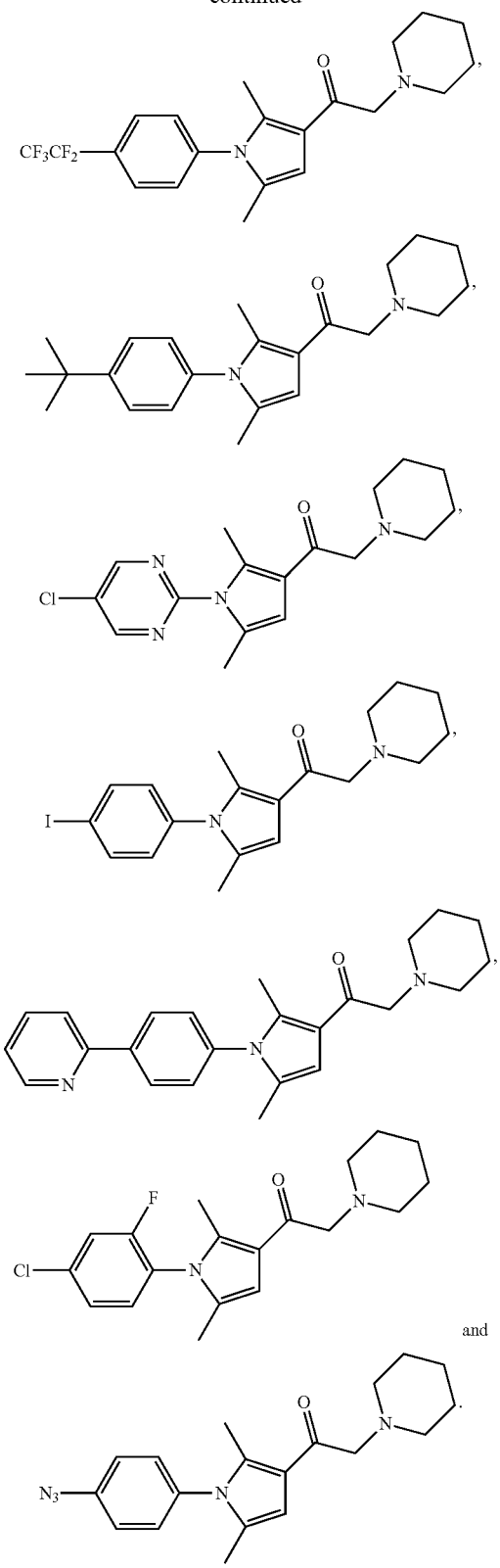

Another aspect of the invention relates to a compound, or a pharmaceutically acceptable salt, solvate, hydrate, prodrug, chemically-protected form, enantiomer or stereoisomer thereof, selected from the group consisting of Another aspect of the invention relates to a compound, or a pharmaceutically acceptable salt, solvate, hydrate, prodrug, chemically-protected form, enantiomer or stereoisomer thereof, selected from the group consisting of

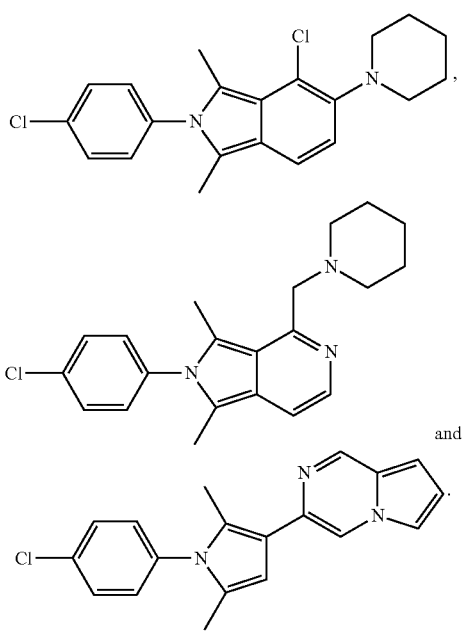

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Pharmaceutically acceptable acid addition salts include those formed with mineral acids such as hydrochloric acid and hydrobromic acid, and those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes pro-drugs. As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol or amine of a compound of the invention wherein the free hydrogen of a hydroxyl or amine substituent is replaced by ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$,—OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O) OCH$_2$C$_6$H$_5$NHCbz); as a t-butoxy amide (—NHC(=O)OC (CH$_3$)$_3$,-NHBoc); a 2-biphenyl-2-propoxy amide (—NHC (=O)OC(CH$_3$)$_2$C$_6$H$_4$C$_6$H$_5$NHBoc), as a 9-fluorenylmethoxy amide (-NHFmoc), as a 6-nitroveratryloxy amide (-NHNvoc), as a 2-trimethylsilylethyloxy amide (-NHTeoc), as a 2,2,2-trichloroethyloxy amide (-NHTroc), as an allyloxy amide (-NHAlloc), as a 2-(phenylsulfonyl) ethyloxy amide (-NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

Pharmaceutical Compositions

The invention provides pharmaceutical compositions comprising inhibitors of Usp14. In one aspect, the present invention provides pharmaceutically acceptable compositions which comprise a therapeutically-effective amount of one or more of the compounds described above, formulated together with one or more pharmaceutically acceptable carriers (additives) and/or diluents. In another aspect, the agents of the invention can be administered as such, or administered in mixtures with pharmaceutically acceptable carriers and can also be administered in conjunction with other agents. Conjunctive therapy thus includes sequential, simultaneous and separate, or co-administration of one or more compound of the invention, wherein the therapeutic effects of the first administered has not entirely disappeared when the subsequent compound is administered.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, in certain embodiments, agents of the invention may be compounds containing a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or through a separate reaction of a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may be compounds containing one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds of the invention may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation of the present invention comprises an excipient, including, but not limited to, cyclodextrins, liposomes, micelle forming agents, e.g., bile acids, and polymeric carriers, e.g., polyesters and polyanhydrides; and an agent of the present invention. In certain embodiments, an aforementioned formulation renders orally bioavailable an agent of the present invention.

Methods of preparing these formulations or compositions may include the step of bringing into association a compound of the present invention with the carrier and, optionally, one or more accessory ingredients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions of the invention may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Exemplary formulations comprising agents of the invention are determined based on various properties including, but not limited to, chemical stability at body temperature, functional efficiency time of release, toxicity and optimal dose.

The preparations of the present invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Therapeutic Methods of the Invention

The present invention further provides novel therapeutic methods of treating proteinopathies and other diseases for which enhanced protein breakdown may be therapeutic, including neurodegenerative diseases, comprising administering to a subject, (e.g., a subject in need thereof), an effective amount of a compound of the invention.

A subject in need thereof may include, for example, a subject who has been diagnosed with a proteinopathy or a subject who has been treated for a proteinopathy, including subjects that have been refractory to the previous treatment.

The methods of the present invention may be used to treat any proteinopathy. Examples of such proteinopathies include, but are not limited to, Alzheimer's disease, cerebral β-amyloid angiopathy, retinal ganglion cell degeneration, prion diseases (e.g. bovine spongiform encephalopathy, kuru, Creutzfeldt-Jakob disease, variant Creutzfeldt-Jakob disease, Gerstmann-Straussler-Scheinker syndrome, fatal familial insomnia) tauopathies (e.g. frontotemporal dementia, Alzheimer's disease, progressive supranuclear palsy, corticobasal degeneration, frontotemporal lobar degeneration), frontotemporal lobar degeneration, amyotrophic lateral sclerosis, Huntington's disease, familial British dementia, Familial Danish dementia, hereditary cerebral hemorrhage with amyloidosis (Icelandic), CADASIL, Alexander disease, Seipinopathies, familial amyloidotic neuropathy, senile systemic amyloidosis, serpinopathies, AL amyloidosis, AA amyloidosis, type II diabetes, aortic medial amyloidosis, ApoAI amyloidosis, ApoAII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, cystic fibrosis, sickle cell disease, critical illness myopathy, von Hippel-Lindau disease, spinocerebellar ataxia 1, Angelman syndrome, giant axon neuropathy, inclusion body myopathy with Paget disease of bone and frontotemporal dementia (IBMPFD).

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the subject agent may be determined by reference to the plasma concentrations of the agent. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent which is the lowest dose effective to produce a therapeutic effect. Such an effective dose will generally depend upon the factors described above.

If desired, the effective daily dose of the agent may be administered as two, three, four, five, six or more sub-doses administered separately at appropriate intervals throughout the day, optionally, in unit dosage forms.

The precise time of administration and amount of any particular agent that will yield the most effective treatment in a given patient will depend upon the activity, pharmacokinetics, and bioavailability of a particular agent, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use an agent that modulates an autotrophy-associated gene product and a second agent, e.g. another agent useful for the treatment of the autophagy-related disease, may reduce the required dosage for any individual agent because the onset and duration of effect of the different compounds and/or agents may be complimentary.

One aspect of the invention relates method of inhibiting the deubiquitination activity of a Usp14 protein comprising contacting the Usp14 protein with any one of the aforementioned compounds (including IU1), or a pharmaceutically acceptable salt, solvate, hydrate, prodrug, chemically-protected form, enantiomer or stereoisomer thereof.

Another aspect of the invention relates to a method of enhancing protein degradation by a proteasome in a cell comprising contacting the cell with any one of the aforementioned compounds (including IU1), or a pharmaceutically acceptable salt, solvate, hydrate, prodrug, chemically-protected form, enantiomer or stereoisomer thereof.

Another aspect of the invention relates to a method of treating or preventing a proteinopathy in a subject comprising administering to the subject any one of the aforementioned compounds (including IU1), or a pharmaceutically acceptable salt, solvate, hydrate, prodrug, chemically-protected form, enantiomer or stereoisomer thereof.

In certain embodiments, the present invention relates to any of the aforementioned methods, wherein the proteinopathy is selected from the group consisting of Alzheimer's disease, cerebral β-amyloid angiopathy, retinal ganglion cell degeneration, bovine spongiform encephalopathy, kuru, Creutzfeldt-Jakob disease, variant Creutzfeldt-Jakob disease, Gerstmann-Straussler-Scheinker syndrome, fatal familial insomnia, frontotemporal dementia, Alzheimer's disease, progressive supranuclear palsy, corticobasal degeneration, frontotemporal lobar degeneration, frontotemporal lobar degeneration, amyotrophic lateral sclerosis, Huntington's disease, familial British dementia, Familial Danish dementia, hereditary cerebral hemorrhage with amyloidosis (Icelandic), CADASIL, Alexander disease, familial amyloidotic neuropathy, senile systemic amyloidosis, serpinopathies, AL amyloidosis, AA amyloidosis, type II diabetes, aortic medial amyloidosis, ApoAI amyloidosis, ApoAII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, cystic fibrosis, sickle cell disease and critical illness myopathy.

In certain embodiments, the present invention relates to any of the aforementioned methods, wherein the proteinopathy is Alzheimer's disease, frontotemporal lobar degeneration, amyotrophic lateral sclerosis or Machado-Joseph disease.

Another aspect of the invention relates to a method of treating or preventing a disease, for which enhanced protein breakdown may be therapeutic, in a subject comprising administering to the subject any one of the aforementioned compounds (including IU1), or a pharmaceutically acceptable salt, solvate, hydrate, prodrug, chemically-protected form, enantiomer or stereoisomer thereof, or a pharmaceutical composition thereof.

In certain embodiments, the present invention relates to any of the aforementioned methods, wherein the disease is selected from the group consisting of von Hippel-Lindau disease, spinocerebellar ataxia 1, Angelman syndrome, giant axon neuropathy, inclusion body myopathy with Paget disease of bone and frontotemporal dementia (IBMPFD).

Another aspect of the invention relates to a method of enhancing proteasome function in a subject comprising administering to the subject any one of the aforementioned compounds (including IU1), or a pharmaceutically acceptable salt, solvate, hydrate, prodrug, chemically-protected form, enantiomer or stereoisomer thereof, or a pharmaceutical composition thereof.

Another aspect of the invention relates to a method of increasing degradation of Tau, TDP-43 or ataxin-3 in a subject comprising administering to the subject any one of the aforementioned compounds (including IU1), or a pharmaceutically acceptable salt, solvate, hydrate, prodrug, chemically-protected form, enantiomer or stereoisomer thereof, or a pharmaceutical composition thereof.

In certain embodiments, the present invention relates to any of the aforementioned methods, wherein said subject is human.

Isolated Reconstituted Proteasomes

Certain aspects of the invention relate to isolated proteasomes that lack enzymatically active Uch37 but comprise enzymatically active Usp14. Such proteasomes can be from any suitable organism. In certain embodiments the proteasomes of the invention are mammalian proteasomes, such as human or murine proteasomes. Such proteasomes may contain enzymatically inactive Uch37 or may lack Uch37 altogether. The proteasomes of the invention are useful, for example, in methods of screening for specific inhibitors of Usp14. See, for example, International Patent Application Publication WO 2008/147536 A1, hereby incorporated by reference in its entirety.

In certain embodiments, the proteasomes of the invention include enzymatically inactive Uch37. Uch37 can be rendered inactive through any method known in the art, including, for example, through mutation of its enzymatic site, through treatment with a Uch37 specific inhibitor, or through treatment with a non-specific deubiquitinase inhibitor (e.g., through treatment with ubiquitin-vinylsulfone).

Treatment of Uch37 with ubiquitin-vinylsulfone results in the generation of vinylsulfone-Uch37 adducts, which are inactive for deubiquitinase activity.

Another aspect of the invention relates to methods of generating proteasomes of the invention. Such methods may include steps of purifying a proteasome lacking Usp14 but comprising Uch37, treating the purified proteasome with a deubiquitinase inhibitor, and/or reconstituting the purified proteasome with enzymatically active Usp14.

Purification of the proteasome lacking Usp14 but comprising Uch37 can be done using any suitable method known in the art. For example, human proteasomes can be affinity-purified from a HEK293 cell line that expresses HTBH-tagged hRpn11. The cells can be lysed and the proteasomes affinity purified with NeutrAvidin agarose resin to produce proteasomes lacking Usp14 but containing Uch37.

Any suitable Uch37 inhibitor can be used in the methods of the invention, including Uch37 specific inhibitors and non-specific deubiquitinase inhibitor (e.g., ubiquitin-vinylsulfone).

The active Usp14 that is used to reconstitute the proteasomes of the invention can be from any suitable source, including, for example, Usp14 purified from a mammalian cell or recombinantly produced Usp14.

Another aspect of the invention relates to methods of screening for inhibitors of Usp14 comprising providing a proteasome of the invention, contacting the proteasome with a test compound and a Usp14 substrate, and determining whether the test compound inhibits the deubiquitination of the substrate.

Deubiquitination of the substrate can be detected either directly or indirectly using any suitable method. For example, in certain embodiments, the substrate is coupled to a reporter that is detectable after cleavage by a deubiquitinase and/or is an ubiquitin-dependent proteasome substrate (e.g, Ub-AMC). In other certain embodiments, deubiquitination of the substrate is demonstrated by inhibition of substrate degradation.

Another aspect of the invention relates to a kit comprising the isolated proteasome of the invention, instructions of use, and/or a Usp14 substrate. In some embodiments the Usp14 substrate is Ub-AMC and/or polyubiquitinated cyclin B.

EXAMPLES

The invention now being generally described, it will be more readily understood by reference to the following, which is included merely for purposes of illustration of certain aspects and embodiments of the present invention, and is not intended to limit the invention.

Example 1

Synthesis of Inhibitors

FIG. 29 depicts one approach to the preparation of pyrroles of the invention. By forming a 1,3-diazole, instead of a pyrrole, similar diazole compounds may be prepared. By varying the ring substitution on aryl amine 1a, or substituting an alkyl amine, heteroaryl amine, aralkyl amine, etc., a wide variety of compounds may be prepared. Likewise, compound 1e may be reacted with a number of nucleophiles to provide a wide variety of compounds. Experimental procedures corresponding to the compounds shown in FIG. 29 are provided below.

Synthesis of 1-(4-chlorophenyl)-2,5-dimethylpyrrole (1c). A mixture of 1a (7.65 g, 60.0 mmol) and 1b (34.2 g, 300.0 mmol) in acetic acid (40 mL) was heated to 100° C. for 1 hour, the solvent was then evaporated and the residue was purified by silica column chromatography to give 1c (11.07 g, yield: 89.8%).

Synthesis of 2-chloro-1-[1-(4-chlorophenyl)-2,5-dimethylpyrrol-3-yl]ethan-1-one (1e). To a solution of $AlCl_3$ (7.98 g, 60.0 mmol) in 1, 2-dichloroethane (50 mL) was added 1d (6.78 g, 60.0 mmol) at 0° C. The resulting mixture was stirred for 30 min and added to a solution of 1c (6.17 g, 30.0 mmoL) in 1,2-dichloroethane (50 mL) at 0° C. The reaction mixture was then warmed to room temperature for 2 hour and poured into ice-water (20 mL). The mixture was extracted with dichloromethane (15 mL×3), dried over $MgSO_4$ and purified by silica column chromatography to give 1e, 3.37 g, yield: 39.9%

Synthesis of 1-[1-(4-chlorophenyl)-2,5-dimethylpyrrol-3-yl]-2-piperidylethan-1-one (1). To a solution of 1e (85 mg, 0.3 mmol) and triethylamine (61 mg, 0.6 mmol) in acetonitrile (10 mL) was added if (28 mg, 0.33 mmol). After being heated to reflux for 1 hour, the mixture was concentrated and the residue was dissolved in dichloromethane (30 mL), washed with sat. $NaHCO_3$ (10 mL), dried over $MgSO_4$ and purified by silica column chromatography to give 1 (83 mg, yield: 83.8%). LC/MS: 331.1 $(M+1)^+$. 1H NMR ($CDCl_3$, 300 MHz): 7.45-7.49 (2H, dd), 7.10-7.13 (2H, dd), 6.39 (2H, ds), 3.56 (2H, s), 2.53-2.56 (4H, m), 2.30 (3H, s), 1.98 (3H, s), 1.62-1.70 (4H, m), 1.44-1.49 (2H, m).

Example 2

Usp14 Mediates Substrate Deubiquitination

To test whether Usp14 is a potent inhibitor of human proteasomes, a purification procedure was developed to generate proteasomes that lack detectable levels of deubiquitinase Usp14 (modified from Wang et al., (2007), Biochemistry, 46, 3553-3565). Briefly, human proteasomes were affinity-purified on a large scale from a stable HEK293 cell line harboring HTBH-tagged hRpn11. The cells were Dounce-homogenized in lysis buffer (50 mM $NaH_2PO_4$ [pH 7.5], 100 mM NaCl, 10% glycerol, 5 mM $MgCl_2$, 0.5% NP-40, 5 mM ATP, and 1 mM DTT) containing protease inhibitors. Lysates were cleared, then incubated with NeutrAvidin agarose resin (Thermo Scientific) overnight at 4° C. The beads were then washed with excess lysis buffer followed by the wash buffer (50 mM Tris-HCl [pH 7.5], 1 mM $MgCl_2$ and 1 mM ATP). For VS-proteasomes, 1 to 1.5 µM of Ub-VS (Boston Biochem) was added to the resin and incubated at 30° C. for 2 h. Residual Ub-VS was removed by washing the beads with at least 20 bed vol of wash buffer. 26S proteasomes were eluted from the beads by cleavage, using TEV protease (Invitrogen).

Figure 1A:
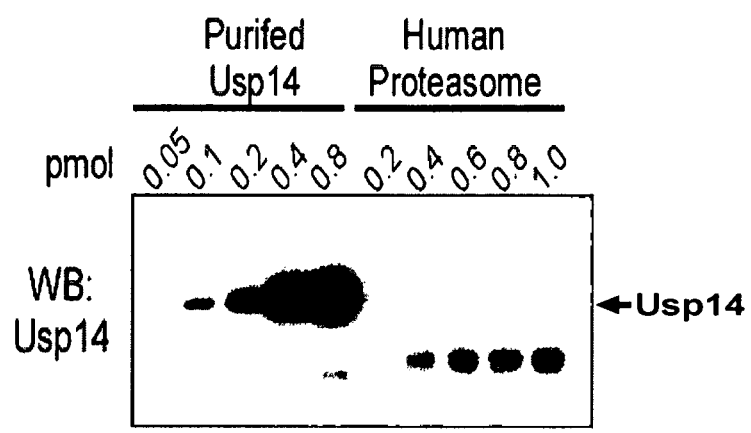
FIG. 1A shows an immunoblot that was performed using either recombinant Usp14 protein (Purified Usp14) or affinity-purified Usp14 deficient human proteasomes (Human Proteasome) and anti-Usp14 antibody. The band corresponding to Usp14 is indicated.
Figure 1B:
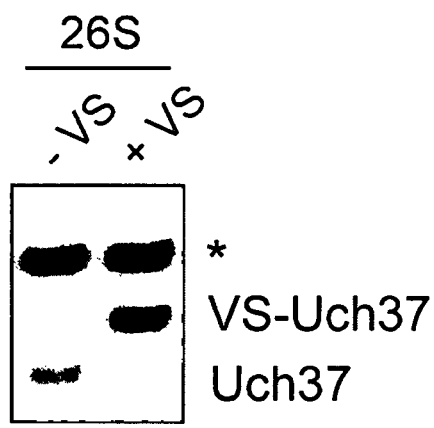
FIG. 1B shows an immunoblot that was performed using anti-Uch37 antibody and Usp14-deficient purified human proteasomes (26S) either untreated (−VS) or treated with Ub-VS (+VS). The band corresponding to Uch37 is indicated. Nonspecific bands are indicated with an asterisk.

Using this proteasome purification procedure, Human proteasomes were affinity-purified from a hRpn11-tagged line of HEK293 cells. Purification of proteasomes lacking Usp14 but containing related deubiquitinase Uch37 was confirmed by western blot using an anti-Usp14 and anti-Uch37 antibodies (FIGS. 1A and 1B, respectively). The purified Usp14-free proteasome (also described as 26S proteasomes) retained high levels of deubiquitinating activity that could be irreversibly inhibited by treating the proteasome with ubiquitin-vinylsulfone (Ub-VS, Yao et al., (2006) Nat. Cell Biol., 8, 994-1002). Ub-VS inhibits deubiquitination of substrates by forming adducts with the Cys amino acid located in the active site of thiol protease class deubiquitinating enzymes. As demonstrated in FIG. 1B, addition of Ub-VS to 26S proteasomes resulted in enzymatically inactive VS-Uch37 adducts forming with all detectable Uch37.

In order to generate pure, recombinant Usp14 enzyme, GST-Usp14 (WT and C114A variants) was expressed in *E. coli* strain Rosetta 2 (DE3) cells (Novagen). Cultures were grown at 37° C. until $OD_{600}$ reached 0.6 to 0.8, and expression was induced overnight with 1 mM IPTG at room temperature. Cells were then harvested in PBS containing protease inhibitors and lysed by French press. The cleared lysates were incubated with GST Sepharose 4B resin (GE Healthcare) at 4° C. for 1 h, and subsequently washed with excess PBS, followed by PBS containing 100 mM NaCl. The GST moiety was removed by thrombin in the cleavage buffer (50 mM Tris-HCl [pH 8.0], 150 mM NaCl, 2.5 mM $CaCl_2$, and 0.1% 2-mercaptoethanol) for 3 h at room temperature. GST-tagged Usp14 proteins for proteasome binding assays were eluted before thrombin cleavage using elution buffer (10 mM reduced glutathione in 50 mM Tris-HCl [pH 8.0]).

Figure 2A:
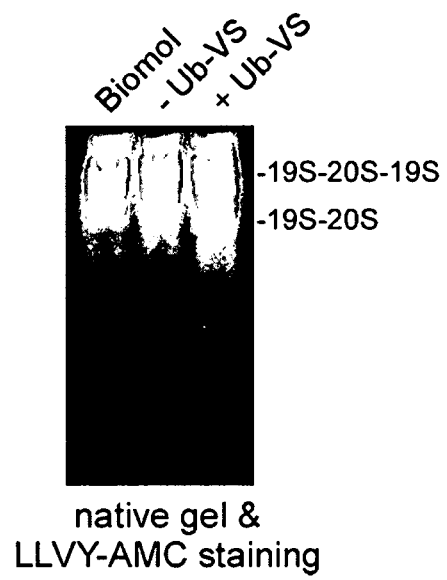
FIG. 2A shows a nondenaturing gel analysis that had undergone in-gel suc-LLVY-AMC staining (indicating presence of proteasomes) that was performed using commercially available human proteasomes (Biomol), untreated, purified Usp14 deficient human proteasomes (+Ub-VS) or Ub-VS treated purified Usp14 deficient human proteasomes (+Ub-VS).
Figure 2B:
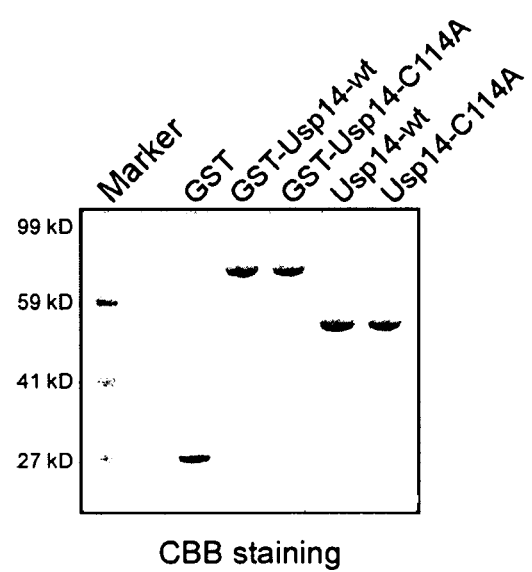
FIG. 2B shows a Coomassie Brilliant Blue (CBB) staining of purified, recombinant wild-type Usp14 (Usp14-wt) or catalytically inactive mutant Usp14 (Usp14-C114A) either with or without a GST tag, along with a GST control (GST) and a protein size marker (Marker).
Figure 2C:
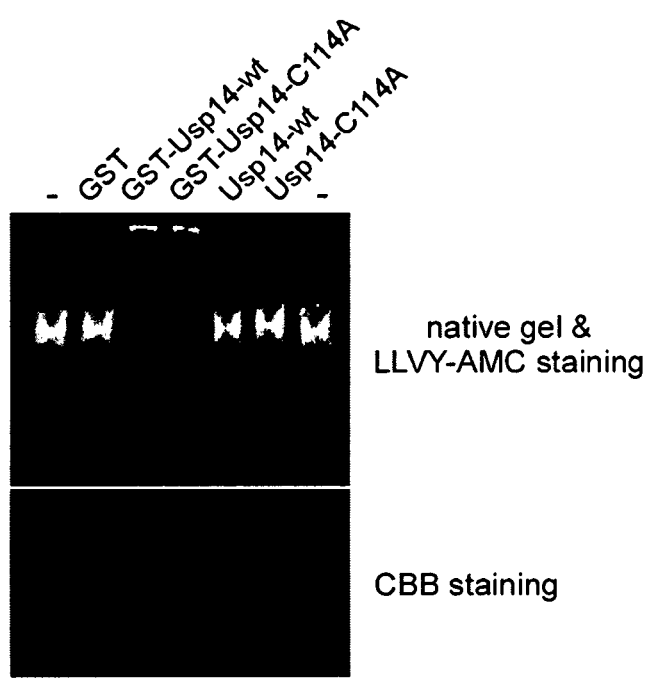
FIG. 2C shows the results of a gel-shift assay of proteasomes alone (−), GST and proteasomes (GST), GST tagged wild-type Usp14 and proteasomes (GST-Usp14-wt), GST tagged catalytically inactive mutant Usp14 and proteasomes (GST-Usp14-C114A), untagged wild-type Usp14 and proteasomes (Usp14-wt) or untagged catalytically inactive mutant Usp14 and proteasomes (Usp14-C114A) that had either been stained with in gel suc-LLVY-AMC staining (top, to show the presence of proteasomes) or Coomassie Brilliant Blue (CBB) staining.
Figure 3:
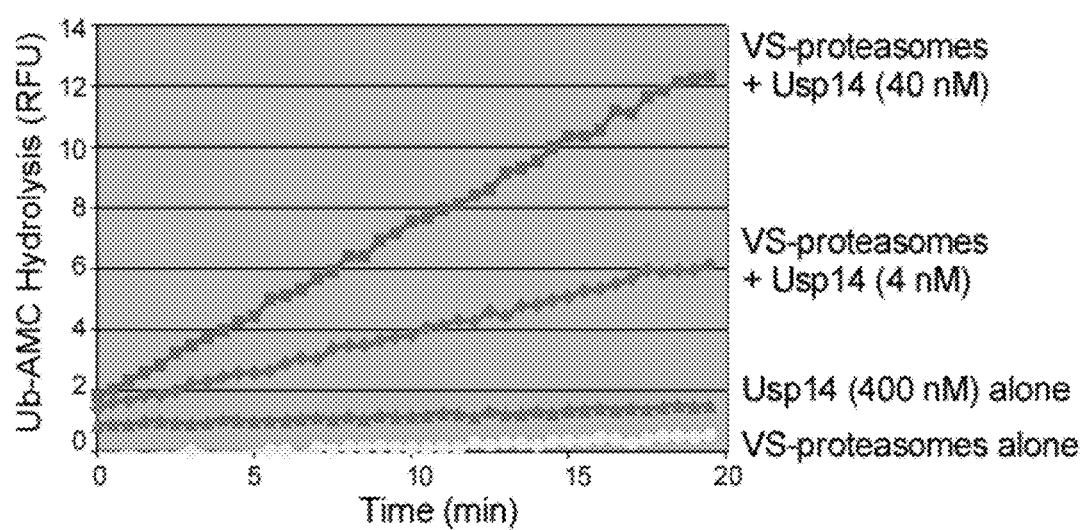
FIG. 3 shows the results of a Ub-AMC hydrolysis assay for Usp14 activity in the presence or Ub-VS treated human proteasomes.
Figure 4A:
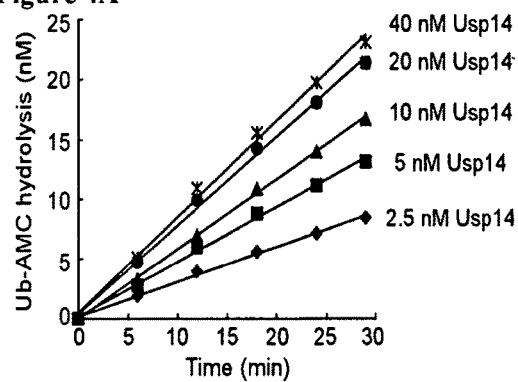
FIG. 4A shows a plot of the linear kinetics ($R^2>0.99$) of the initial rates of Ub-AMC hydrolysis by Usp14 and proteasome at 1 µM Ub-AMC, 1 nM proteasome, and the indicated concentration of Usp14.
Figure 4B:
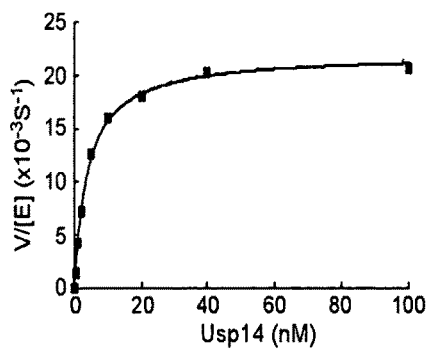
FIG. 4B shows a Michaelis-Menten plot of Usp14-dependent Ub-AMC hydrolysis in the presence of human proteasome for 25 minutes at 1 µM Ub-AMC, 1 nM proteasome, and the indicated concentration of Usp14.
Figure 4C:
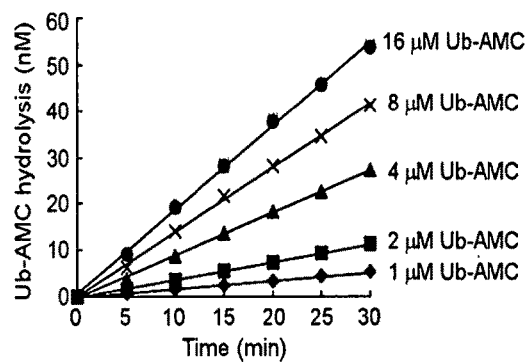
FIG. 4C shows a plot of the linear kinetics ($R^2>0.99$) of the initial rates of Ub-AMC hydrolysis by Usp14 and proteasome at 4 nM Usp14, 1 nM proteasome and the indicated concentration of Ub-AMC.
Figure 4D:
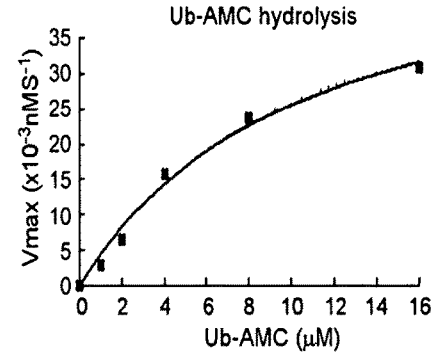
FIG. 4D shows a Michaelis-Menten plot of concentration-dependent Ub-AMC hydrolysis in the presence of Usp14 and human proteasome for 30 minutes at 4 nM Usp14, 1 nM proteasome and the indicated concentration of Ub-AMC.

The inhibited "VS-proteasomes" described above, which lack endogenous deubiquitination activity due to Ub-VS treatment, were successfully reconstituted with recombinant Usp14 (FIG. 2). An Ub-AMC hydrolysis assay was performed with 1 nM of Ub-VS treated human proteasome (VS-Proteasome) alone, 400 nM of Usp14 alone, or VS-proteasome that had been reconstituted with 4 or 40 nM of recombinant Usp14 protein. As has been described above, the deubiquitination activity of the VS-proteasome was almost completely inhibited (FIG. 3). In contrast, the reconstituted Usp14/VS proteasome demonstrated substantial deubiquitination activity (FIG. 3). In fact, the Usp14/VS proteasome demonstrated an 800-fold increase in Ub-AMC hydrolyzing activity over that of isolated Usp14 alone (FIG. 3). Thus, the enzymatic activity of Usp14 is increased by its complexing with the proteasome. Therefore, the Ub-AMC assay allows the success of reconstitution to be followed.

The Ub-AMC assay was also used to examine the kinetics of Ub-AMC hydrolysis by the reconstituted Usp14-proteasome complexes. Ub-AMC hydrolysis by Usp14/VS proteasomes that had been reconstituted with various amounts of Usp14 was monitored over a period of 30 minutes (FIG. 4). Analysis of the results of this assay demonstrated the affinity of Usp14 for the proteasome is approximately 4 nM.

Example 3

Usp14 Inhibits Proteasomal Degradation

Figure 5:
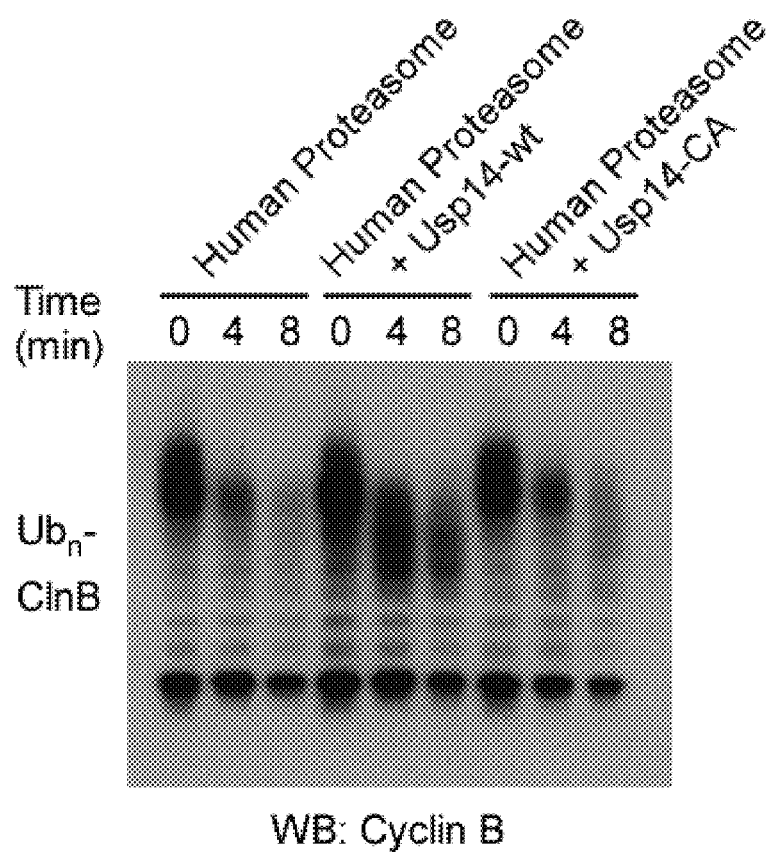
FIG. 5 shows an immunoblot that was performed using an antibody specific for Cyclin B, which also detects polyubiquitinated Cyclin B ($Ub_n$-ClbB). In this experiment, $Ub_n$-ClbB was treated with 26S human proteasome alone, human proteasome and wild-type Usp14 (Usp14-wt) or human proteasome and catalytically inactive Usp14 (Usp14-CA), and subsequently analyzed by immunoblotting.

The effect of Usp14 on the degradation of ubiquitinated substrates was examined using an in vitro degradation assay using the ubiquitin-dependent proteasome substrate polyubiquitinated cyclin B ($Ub_n$-ClnB). In these experiments, $Ub_n$-ClnB was incubated with human proteasomes (4 nM), containing either wild-type or catalytically inactive Usp14 (60 nM). The catalytically inactive Usp used in these assays was Usp14-C114A, which contains a mutation in Usp14's active site for deubiquitination. Notably, both wild-type Usp and Usp14-C114A are able to bind to 26S mammalian proteasomes (FIG. 2). As demonstrated in FIG. 5, Usp14 strongly inhibits the degradation of cyclin B, while the active site mutant of Usp14 showed little inhibitory effect. The lack of inhibition of $Ub_n$-ClnB degradation by the active site mutant indicates that the ubiquitin chain trimming activity of wild-type Usp14 is required for Usp14's inhibition of proteasome degradation. Indeed, extensive trimming of the ubiquitin groups from cyclin B was evident by immunoblot analysis in the samples containing wild-type Usp14, but was nearly eliminated when catalytically inactive Usp14 was used (FIG. 5).

Figure 6A:
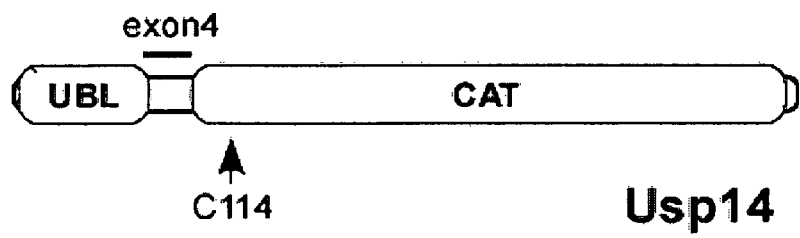
FIG. 6A shows a diagram of human Usp14, depicting the ubiquitin-like domain (UBL), the catalytic domain (CAT), the location of exon 4 and the position of Cys114.
Figure 6B:
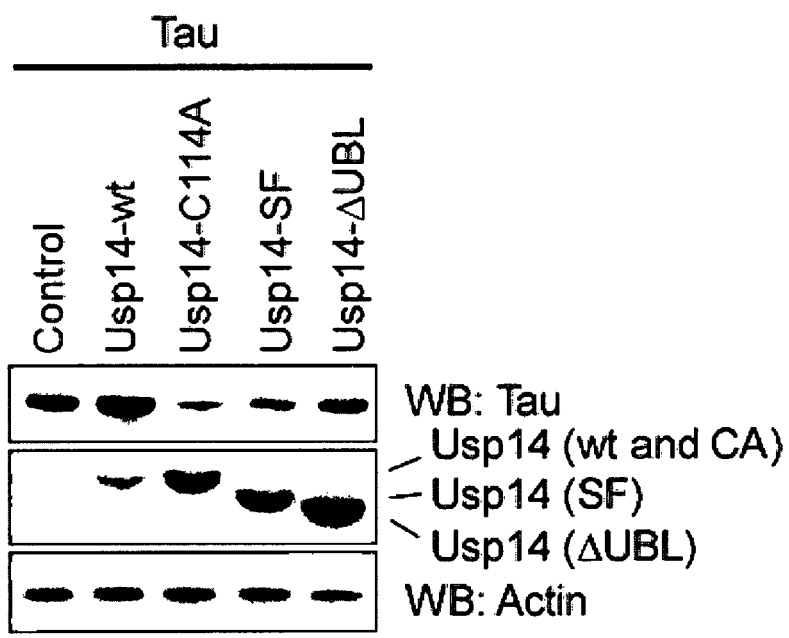
FIG. 6B shows immunoblots that were performed on cellular lysates from human 293 cells that co-expressed Tau along with either wild-type Usp14 (Usp14-wt), catalytically inactive Usp14 (Usp14-CA), short form Usp14 (Usp14-SF)

An effect of Usp14 on Tau degradation in human cells was observed in the human cell line, HEK293. Tau was coexpressed with exogenous wild-type or catalytically inactive Usp14 and Tau protein levels were determined by western blot. Expression of wild-type Usp14, but not enzymatically inactive Usp14, stabilized Tau in the human cell line (FIG. 6). In fact, expression of enzymatically inactive Usp14 in HEK293 cells resulted in accelerated Tau degradation (FIG. 6B). This dominant negative effect likely reflects the displacement of endogenous, wild-type Usp14 from the proteasome. This hypothesis was confirmed using a mutant form of Usp14 that lacks the N-terminal UBL domain (Usp14-ΔUBL). The N-terminal UBL domain (FIG. 6A) is the principal proteasome-binding site on Usp14. Deletion of the UBL attenuated the dominant negative effect (FIG. 7), indicating that proteasome binding is required for the mediation of this effect.

The short form (SF) of Usp14 is an endogenous Usp14 splice variant that is expressed from mRNA that lacks a junctional exon (exon 4) between the N-terminal ubiquitin-like domain of Usp14 and its catalytic domain (Wilson et al., (2002), Nat. Genet., 32, 420-425; FIG. 6A). Like the catalytically inactive mutant of Usp14, Usp14-SF exhibited a dominant negative effect on Tau stability in HEK293 cells (FIG. 6A). This suggests that Usp14-SF may be an endogenous inhibitor of Usp14. Consistent with this possibility, Usp14-SF is able to bind proteasome, but unlike the wild-type enzyme, it is not activated enzymatically by proteasome binding (FIG. 7).

Example 4

Specific Inhibitors of Usp14

As demonstrated above, chain trimming at the proteasome by Usp14 is a key regulatory step in the ubiquitin-dependent proteolytic pathway. Therefore, in order to identify enhancers of proteasome function, a high-throughput screen for small molecule Usp14 inhibitors was performed using VS-proteasomes reconstituted with recombinant Usp14 and assayed with Ub-AMC (FIG. 8).

Compounds were screened for Usp14/26S inhibition in 384-well low-volume plates in duplicate. Data processing was done by a robust Z-score method and each compound was plotted using Spotfire software. Compounds over the cut-off of Z>5 were mostly autofluorescent and were therefore not counted. To exclude quenching compounds that only affect AMC fluorescence, 312 primary hits were tested for quenching of AMC amine, and pure quenchers were scored as false-positives and excluded from further analysis (FIG. 8B). Of the 63,052 compounds analyzed in the high-throughput screen, 215 were identified as true inhibitors of Usp14.

In order to identify compounds that specifically inhibited Usp14 but were not general deubiquitinase inhibitors, the 215 hit compounds were counterscreened against a panel of deubiquitinating enzymes. Among the hit compounds that inhibited the activity of Usp14 but not any other tested deubiquitinase, 1-[1-(4-fluorophenyl)-2,5-dimethlypyrrol-3-yl]-2-pyrrolidin-1-ylethanone (IU1, FIG. 9) was selected for further analysis.

Example 5

Specific Inhibition of Usp14 by IU1

Additional studies were performed on the specific Usp14 inhibitor IU1. To serve as a negative control, a compound that is structurally similar to IU1, termed "IU1C" (FIG. 10A) which does not inhibit Usp14 deubiquitinase (FIG. 10B) or enhance proteasome function (FIG. 10C) was also identified.

The specificity of IU1 for Usp14 was determined by testing its ability to inhibit the activity of eight deubiquitinating enzymes of human origin. As seen in FIGS. 11 and 9C, despite being a potent inhibitor of proteasome-bound Usp14, IU1 failed to significantly inhibit the other tested deubiquitinating enzymes, including Uch37. Note that FIG. 9E shows that IU1 does not inhibit the proteasome-bound form of Uch37. Furthermore, IU1 also failed to inhibit the activity of Usp14 that had not been loaded onto a proteasome (FIG. 9D), indicating that IU1 specifically inhibits the proteasome-bound, activated form of Usp14.

As the binding of Usp14 to the proteasome enhances Usp14 activity, it was possible that IU1 inhibited Usp14 activity by interfering with the Usp14/proteasome interaction. Therefore, ability of IU1 to interfere with the ability of Usp14 to bind to the proteasome was examined. Purified human proteasomes were incubated with recombinant Usp14 either in the presence or the absence of various concentrations of IU1. As seen in FIG. 12, IU1 did not antagonize Usp14 complexing with the proteasome, indicating that the inhibitory activity of IU1 is not the result of an inhibition of the formation of Usp14/proteasome complexes.

The reversibility of IU1 inhibition of Usp14 was next assayed. Usp14/proteasome complexes were treated with IU1, followed by centrifugation with a Micron-YM3 filter up to three times. After each spin, the protein complex was tested for deubiquitinase activity. As demonstrated in FIG. 13, the activity of Usp14 returned following centrifugation, thereby indicating that inhibition of Usp14 by IU1 is rapidly reversible. Consistent with this observation, mass spectrometry analysis of IU1 inhibited Usp14 failed to detect any covalent IU1-Usp14 adducts.

The Usp14 inhibitory activity of IU1 was further quantified by generating two independent $IC_{50}$ curves for Usp14/26S proteasome complexes treated with various concentrations of IU1 for either 45 minutes (FIG. 14A) or 30 minutes (FIG. 14B). The data plot of each experiment was fit into a four parameter logistic model (the Hill-slope model) based on guidelines from the NIH Chemical Genomics Center. The results of these experiments indicated that the $IC_{50}$ value of IU1 is 2-5 µM (FIG. 14).

Using methods similar to those described in Example 3, Cyclin B was used as a substrate to test whether IU1 influenced the trimming of ubiquitin chains by proteasome complexes. To separate chain trimming from substrate degradation, these assays were done in the presence of proteasome inhibitors. The effectiveness of the proteasome inhibitors is evidenced by the accumulation of unmodified cyclin B in the assay (FIG. 15). When proteasomes that lack Usp14 were tested, IU1 had little or no effect on the release of ubiquitin chains from cyclin B (FIG. 15), which is likely mediated by another deubiquitinating enzyme on the proteasome, Rpn11. Upon the addition of Usp14, however, chain trimming by the proteasome complexes was strongly enhanced, as apparent from the increased electrophoretic mobility of the ubiquitinated forms of cyclin B. The further addition of IU1 to the Usp14/proteasome complexes reversed this effect, and reduced the chain trimming to a level similar to that of the proteasome complexes that lacked Usp14 (FIG. 15).

It was next tested whether IU1 could serve as an enhancer of substrate degradation by the proteasome. Using the methods described in Example 3, an in vitro $Ub_n$-ClnB degradation assay was performed, but this time in the absence or presence of 34 µM IU1. The addition of IU1 to proteasomes that lack Usp14 had no effect on substrate degradation or chain trimming. Confirming the results described above, addition of Usp14 to the proteasome complex enhanced chain trimming and dramatically inhibited substrate degradation. The addition of IU1 stimulated the activity of Usp14-containing proteasomes in degrading Ub-cyclin B and inhibited ubiquitin chain trimming (FIG. 16).

Example 6

Cellular Entry of IU1

The IU1 experiments described above were performed in vitro. In order for IU1 to enhance proteasome degradation in vivo, it is necessary the IU1 be able to enter cells. In order to examine this, entry of IU1 into cells was assayed by electrospray mass spectrometry using an Agilent series 1200 LC/6130 system with a reversed-phase $C_{18}$ column. IU1 was added to MEFs at 50 µM for various periods of time. Cell lysates were collected and ethyl acetate extraction was used to prepare mass spectrometer samples. Ion count of LC/MS traces (m/z at 301) at 0 hr, 1 hr and 24 hr are shown (FIG. 17). This assay revealed that, when added to the medium at 50 µM, IU1 reached a steady-state concentration of ~19 µM within cells by 1 hour, and maintained approximately the same level over the time course of the experiment (FIGS. 17 and 18). Similar results, extending through two days, were obtained using a separate UV absorption assay (FIG. 19). Additionally, IU1 concentrations were maintained in the medium as for at least two days. These results indicate that IU1 is stable compound within both cells and standard media.

Example 7

Enhancement of In Vivo Proteasomal Degradation by IU1

To determine whether IU1 could enhance proteasome function in living cells, Tau was expressed in MEF cells, which were then treated with IU1 at concentrations from 25 to 100 µM. Specifically, after 36 hours of Tau and $LacZ^{V5}$ expression, MEF cells were incubated with 0, 25, 50, 75 or 100 µM of IU1 for 6 hours. As seen in FIG. 21A, IU1 reduced Tau levels at all concentrations tested. No effect was seen on Tau mRNA levels (FIG. 21B).

Other proteins that have been implicated in proteotoxic mechanisms were also tested. Using similar methods to those described above, it was demonstrated that TDP-43 (implicated in frontotemporal lobar degeneration and amyotrophic lateral sclerosis), ataxin-3 (implicated in Machado-Joseph disease) and glial fibrillary acidic protein (GFAP, implicated in Alexander disease) were similarly depleted from cells upon IU1 treatment (FIG. 22A-C). On the other hand, IU1 had little or no effect upon the in vivo degradation of the ubiquitin-independent proteasome substrate, GFP-ODC. Together, these results indicate that IU1 is a general enhancer of the ubiquitin-mediated proteasome degradation.

Oxidized proteins form another class of proteasome substrates that play an important role in human health. Harmful oxidized proteins accumulate upon ageing and are implicated in a variety of age-related diseases and disorders (Stadtman (2006) Protein oxidation and aging. Free Radic. Res. 40, 1250-1258; Ahmed et al. (2007) Protein oxidative modifications and replicative senescence of WI-38 human embryonic fibroblasts. Ann. NY Acad. Sci., 1119, 88-96; Moskovitz et al. (2001). Methionine sulfoxide reductase (MsrA) is a regulator of antioxidant defense and lifespan in mammals. Proc. Nat. Acad. Sci. USA, 1981, 12920-12925.). Protein oxidation was induced by treating cells with menadione, and oxidized species were visualized using an antibody specific for protein carbonyls. Specifically, MEFs were preincubated with vehicle or 75 µM IU1 for 4 hours and then treated with 63 µM menadione for 45 minutes. The cells were lysed and lysates were incubated with DNPH and immunoblotted with anti-DNPH antibody to assay for oxidized proteins. Accumulation of oxidized proteins was reduced in cells treated with IU1 than in untreated cells (FIG. 23). When proteasome inhibitor PS-341 was added together with IU1, the effect of IU1 was eliminated, indicating that IU1 does not prevent oxidation reaction, but rather it enhances the proteasomal degradation of the oxidized proteins. These data indicate that there is a Usp14-inhibited ubiquitin-dependent mechanism for the degradation of proteins damaged by reactive oxygen species. Menadione is toxic to cells, and IU1 treatment reduced this toxicity substantially in HEK293 cells (FIG. 30), strongly supporting the hypothesis that proteins are critical targets of oxidative damage in cells. IU1 also reduced the toxicity of an unrelated oxidizing agent, hydrogen peroxide (data not shown). IU1C, the IU1 variant that is inactive against Usp14, failed to reduce menadione cytotoxicity (data not shown). Importantly, these experiments indicate that IU1 can promote cell survival during proteotoxic stress.

Example 8

The Effects of IU1 on Cellular Proliferation and Viability

The effect of IU1 on cell viability was next examined by MTT assay. IU1 was added to MEF, HEK293 and HeLa cells at various concentrations, followed by addition of MTT solution after 6, 12, 24 or 48 hours of IU1 incubation. Effects on cell viability became apparent at concentrations over 100 µM, well above the doses required to enhance the degradation of Tau, TDP-43, ataxin-3, and oxidized proteins (FIGS. 21-23). Moreover, IU1 did not noticeably induce apoptosis in MEF cells, as assessed by TUNEL assay (FIG. 31).

Cell proliferation of MEFs (FIG. 28) and 293 cells that had been exposed to various concentrations of IU1 was measured by microscopy in real time. The results of this assay revealed only a slight inhibition in cellular proliferation at 120 µM, but no apparent inhibition at lower concentrations (FIG. 28). Taken together with the results of the cell viability assays presented above, this indicates that IU1's inhibition of ubiquitin chain trimming by Usp14 does not grossly compromise cell function.

EQUIVALENTS

The present invention provides, in part, methods for the enhancement of protein turnover by the proteasome and the treatment of diseases involving either proteasome substrates, upstream components of the ubiquitin-proteasome pathway, or the proteasome itself. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

All publications and patents mentioned herein are hereby incorporated by reference in their entirety as if each individual publication or patent was specifically and individually indicated to be incorporated by reference. In case of conflict, the present application, including any definitions herein, will control.

We claim:
1. A compound represented by formula II:

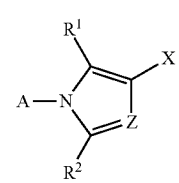

or a pharmaceutically acceptable salt thereof; wherein, A is

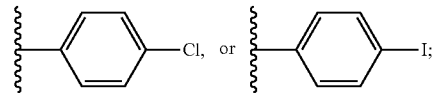

$R^1$ and $R^2$ are the same and are selected from the group consisting of H, methyl, and ethyl;
Z is $=C(R^8)-$;
X is

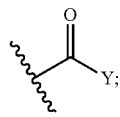

Y is —CH$_2$(N-heterocyclyl), wherein N-heterocyclyl is a saturated monocycle comprising at least one nitrogen atom through which the N-heterocyclyl moiety is bound to the —CH$_2$—, wherein N-heterocyclyl is optionally substituted with one, two, three, four or five substituents independently selected from the group consisting of alkyl, alkoxy, and amino; and
$R^8$ is hydrogen.
2. The compound of claim 1, wherein $R^1$ is methyl; and $R^2$ is methyl.
3. The compound of claim 1, wherein Y is —CH$_2$(piperidin-1-yl), —CH$_2$(piperazin-1-yl), —CH$_2$(hexahydropyrimidin-1-yl), —CH$_2$(morpholin-1-yl) or —CH$_2$(1,3-oxazinan-3-yl), which is optionally substituted with one, two, three, four or five substituents independently selected from the group consisting of alkyl, alkoxy, and amino.

4. The compound of claim 1, wherein Y is
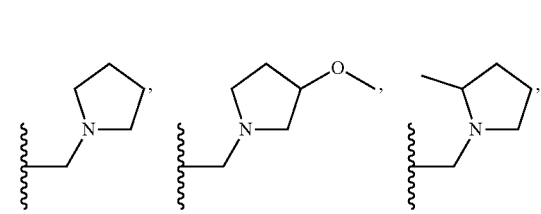
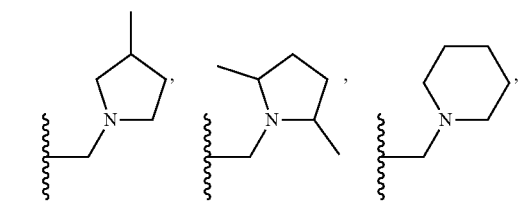
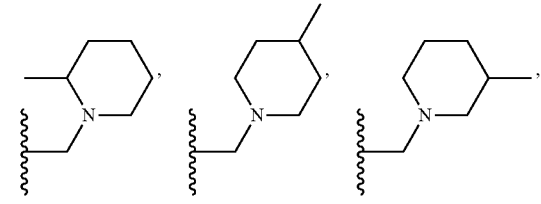
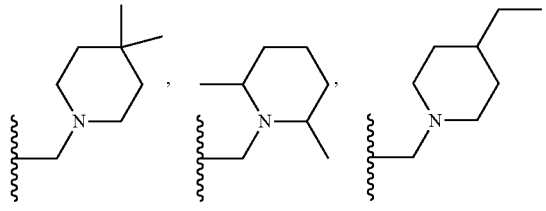
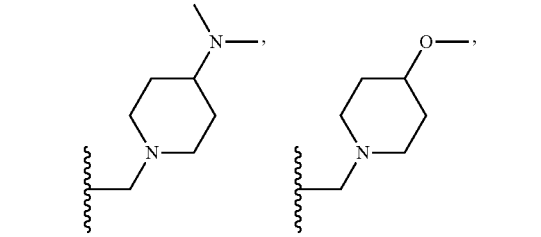
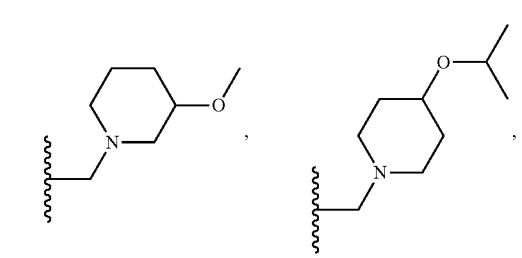
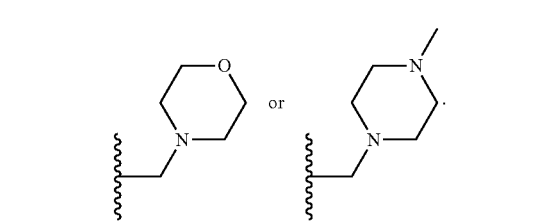
5. A compound or a pharmaceutically acceptable salt thereof selected from the group consisting of
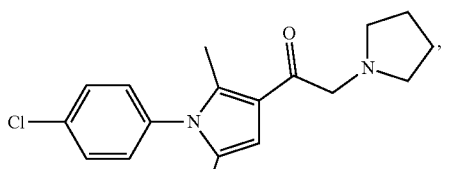
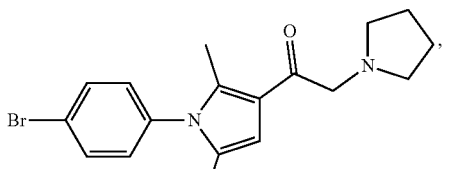
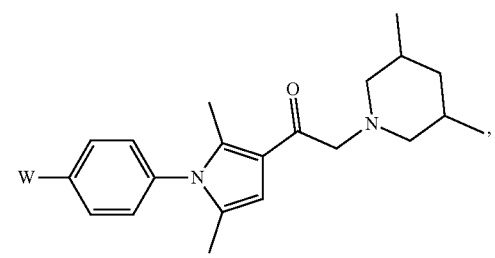
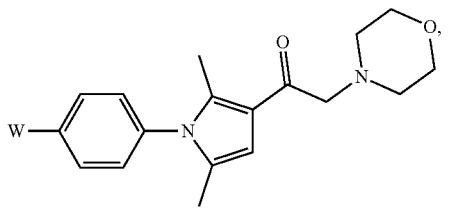
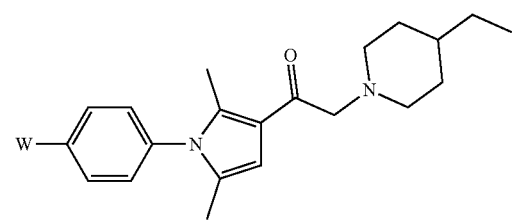
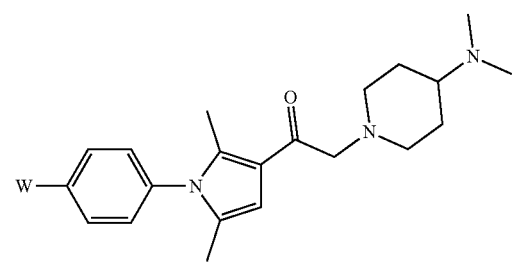
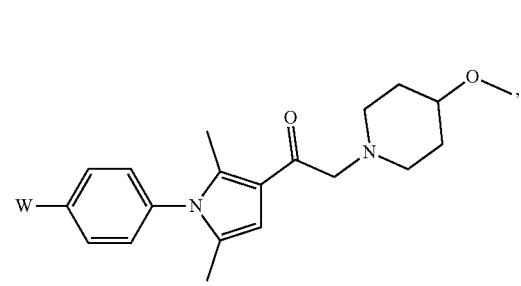

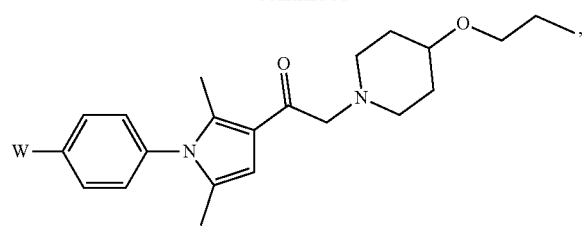
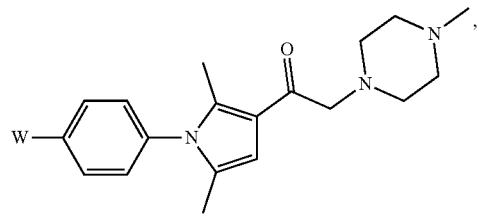
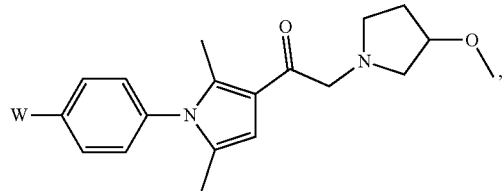
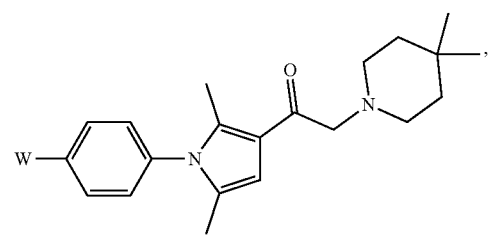
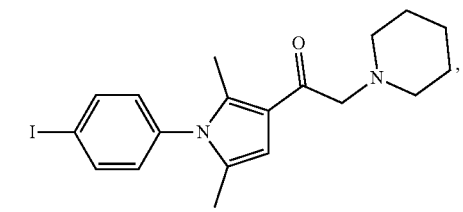
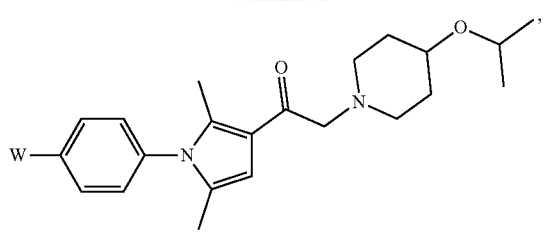
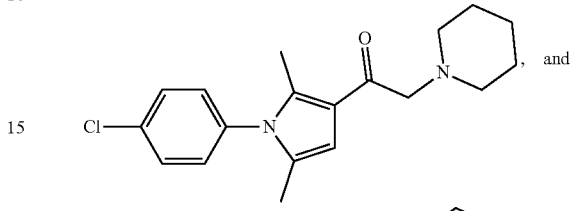
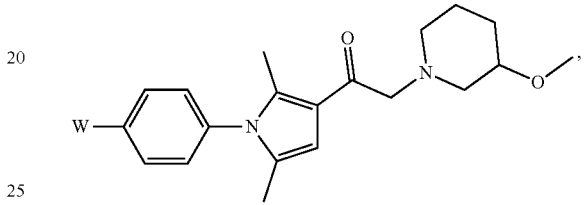
wherein W is chloro.
6. The compound of claim 1, wherein $R^1$ is ethyl; and $R^2$ is ethyl.
7. The compound of claim 1, wherein $R^1$ is hydrogen; and $R^2$ is hydrogen.
8. The compound of claim 1, wherein the compound is
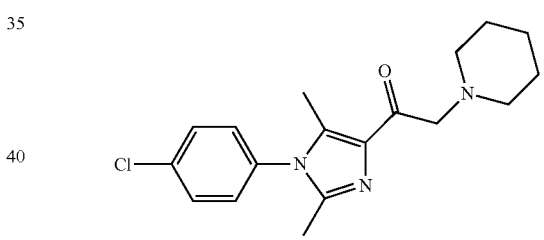
or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 10,351,568 B2 |
| APPLICATION NO. | : 14/933671 |
| DATED | : July 16, 2019 |
| INVENTOR(S) | : Daniel J. Finley et al. |

It is certified that error appears in the above-identified patent and that said Letters Patent is hereby corrected as shown below:

In the Specification

At Column 1, Lines 17-20, under the heading GOVERNMENT SUPPORT, please replace:
"This invention was made with U.S. Government support under National Institutes of Health Grant Nos. GM065592, GM66492, and DK082906. The government has certain rights in the invention."

With:
-- This invention was made with government support under GM065592 and GM066492 and DK082906 awarded by National Institutes of Health (NIH). The government has certain rights in this invention. --

Signed and Sealed this
Twenty-fifth Day of October, 2022

Katherine Kelly Vidal
*Director of the United States Patent and Trademark Office*